(12) United States Patent
Holland et al.

(10) Patent No.: US 10,501,706 B2
(45) Date of Patent: Dec. 10, 2019

(54) FRAGRANCE COMPOSITIONS AND USES THEREOF

(71) Applicant: The Procter & Gamble Company, Cincinnati, OH (US)

(72) Inventors: Lynette Anne Makins Holland, Abbots Langley (GB); Christelle Marie Sandrine Bonnet, Caillouet-Orgeville (FR); Fabienne Pastor, Meriel (FR); Jose Maria Velazquez Mendoza, Ascot (GB); Jonathan Richard Stonehouse, Windlesham (GB); William Eoghan Staite, Egham (GB); David Thomas Stanton, Hamilton, OH (US); Oreste Todini, Brussels (BE); Stephen Robert Schofield, London (GB); Sarah Kyakyo Kanyunyuzi Nyakana, Windsor (GB)

(73) Assignee: The Procter & Gamble Company, Cincinnati, OH (US)

( * ) Notice: Subject to any disclaimer, the term of this patent is extended or adjusted under 35 U.S.C. 154(b) by 107 days.

(21) Appl. No.: 15/175,781

(22) Filed: Jun. 7, 2016

(65) Prior Publication Data

US 2016/0362629 A1    Dec. 15, 2016

Related U.S. Application Data

(60) Provisional application No. 62/174,532, filed on Jun. 12, 2015.

(51) Int. Cl.
| | | |
|---|---|---|
| *C11D 3/50* | (2006.01) | |
| *C11B 9/00* | (2006.01) | |
| *A61Q 13/00* | (2006.01) | |
| *A61Q 19/00* | (2006.01) | |
| *A61K 8/37* | (2006.01) | |
| *A61K 8/34* | (2006.01) | |
| *A61K 8/49* | (2006.01) | |
| *A61K 8/35* | (2006.01) | |
| *A61K 8/60* | (2006.01) | |
| *C11D 1/66* | (2006.01) | |
| *C11D 3/20* | (2006.01) | |
| *C11D 3/22* | (2006.01) | |

(52) U.S. Cl.
CPC .............. *C11B 9/0015* (2013.01); *A61K 8/34* (2013.01); *A61K 8/342* (2013.01); *A61K 8/35* (2013.01); *A61K 8/37* (2013.01); *A61K 8/492* (2013.01); *A61K 8/60* (2013.01); *A61K 8/604* (2013.01); *A61Q 13/00* (2013.01); *A61Q 19/007* (2013.01); *C11B 9/0019* (2013.01); *C11B 9/0034* (2013.01); *C11B 9/0061* (2013.01); *C11B 9/0092* (2013.01); *C11D 1/662* (2013.01); *C11D 1/667* (2013.01); *C11D 3/2068* (2013.01); *C11D 3/2072* (2013.01); *C11D 3/221* (2013.01); *C11D 3/225* (2013.01); *C11D 3/50* (2013.01); *A61K 2800/52* (2013.01)

(58) Field of Classification Search
CPC ........................................................ C11D 3/50
See application file for complete search history.

(56) References Cited

U.S. PATENT DOCUMENTS

| | | | |
|---|---|---|---|
| 4,110,626 | A | 8/1978 | Katada et al. |
| 4,145,184 | A | 3/1979 | Brain |
| 4,152,272 | A | 5/1979 | Young |
| 4,209,417 | A | 1/1980 | Whyte |
| 4,264,478 | A | 4/1981 | Seldner |
| 4,313,855 | A | 2/1982 | Erich et al. |
| 4,324,703 | A | 4/1982 | Seldner |
| 4,515,705 | A | 5/1985 | Moeddel |
| 6,147,049 | A | 11/2000 | Gygax et al. |
| 6,440,400 | B1 | 8/2002 | Aida et al. |
| 6,737,396 | B2 | 5/2004 | Margot et al. |
| 7,196,052 | B2 | 3/2007 | Ishida et al. |
| 7,538,081 | B2 | 5/2009 | Ishida et al. |
| 8,822,404 | B2 | 9/2014 | Wong et al. |
| 9,050,261 | B2 | 6/2015 | Wohrle et al. |
| 9,296,978 | B2 | 3/2016 | Wong et al. |
| 2002/0054893 | A1 | 5/2002 | Ishida et al. |
| 2003/0228334 | A1 | 12/2003 | Mercier et al. |

(Continued)

FOREIGN PATENT DOCUMENTS

| | | |
|---|---|---|
| EP | 616800 | 2/1994 |
| EP | 0875239 A2 | 11/1998 |

(Continued)

OTHER PUBLICATIONS

Dave, H., et al. "Phase behavior and SANS investigations of edible sugar-limonene microemulsions." Colloids and Surfaces A: Physiochem. Eng. Aspects. (2007), vol. 296, pp. 45-50.*

(Continued)

*Primary Examiner* — Andrew D Kosar
*Assistant Examiner* — John S Kenyon

(57) ABSTRACT

The present invention relates to a composition having improved or enhanced fidelilty and/or longevity of the fragrance profile, comprising from about 10 wt % to about 30 wt % of low volatile fragrance materials having a vapor pressure less than 0.001 Torr (0.000133 kPa) at 25° C., wherein the wt % is relative to the total weight of the fragrance component, and at least one substantially non-odorous fragrance modulator. The invention also relates to methods of use of the compositions for perfuming suitable substrates, including hard surfaces and body parts, particularly skin and hair.

5 Claims, 6 Drawing Sheets

(56) References Cited

U.S. PATENT DOCUMENTS

| | | |
|---|---|---|
| 2007/0190014 A1 | 8/2007 | Ide et al. |
| 2011/0091404 A1 | 4/2011 | Wohrle et al. |
| 2011/0104089 A1 | 5/2011 | Wohrle et al. |
| 2013/0079270 A1 | 3/2013 | Wong et al. |
| 2014/0287982 A1 | 9/2014 | Wong et al. |
| 2015/0322374 A1 | 11/2015 | Tchakalova et al. |
| 2016/0015616 A1 | 1/2016 | Harichian et al. |

FOREIGN PATENT DOCUMENTS

| | | | |
|---|---|---|---|
| EP | 1186289 A2 * | 3/2002 | ............... A23L 2/56 |
| JP | 61-063612 | 4/1986 | |
| JP | 61-083114 | 4/1986 | |
| JP | 62-084010 | 4/1987 | |
| WO | WO 85/04803 | 11/1985 | |
| WO | WO 2014/155019 | 10/2014 | |

OTHER PUBLICATIONS

"Limonene." © Apr. 14, 2013. Available from: < https://web.archive.org/web/20140414022748/http://www.cosmeticsinfo.org/ingredient/limonene >.*

Parsons, L. "Limonene: Multipurpose Citrus Product." University of Florida IFAS Extension. © Nov. 2007. Available from: < http://www.crec.ifas.ufl.edu/extension/trade_journals/2007/2007_Nov_limonene.pdf >.*

Dave, H., et al. "Phase behavior and SANS investigations of edible sugar-limonene microemulsions." Colloids and Surfaces A: Physiochem. Eng. Aspects. (2007), vol. 296, pp. 45-50. (Year: 2007).*

"Sucrose oleate." Chemical Book. (Dec. 19, 2014). Accessed Nov. 23, 2018. Available from: < https://www.chemicalbook.com/ChemicalProductProperty_EN_CB8886600.htm> . (Year: 2014).*

"Limonene." (Apr. 14, 2013). Available from: < https://web.archive.org/web/20140414022748/http://www.cosmeticsinfo.org/ingredient/limonene>, (Year: 2013).*

Parsons, L. "Limonene: Multipurpose Citrus Product." University of Florida IFAS Extension. (Nov. 2007). Available from: < http://www.crec.ifas.ufl.edu/extension/trade_journals/2007/2007_Nov_limonene.pdf>. (Year: 2007).*

U.S. Appl. No. 14/567,192, filed Dec. 11, 2014, Oreste Todini, et al.

U.S. Appl. No. 15/175,836, filed Jun. 7, 2016, Lynette Anne Makins Holland, et al.

U.S. Appl. No. 15/183,363, filed Jun. 15, 2016, Isabelle Guimet.

U.S. Appl. No. 15/175,862, filed Jun. 7, 2016, Lynette Anne Makins Holland, et al.

U.S. Appl. No. 14/705,373, filed May 6, 2015, Lynette Anne Makins Holland, et al.

U.S. Appl. No. 14/105,230, filed Dec. 13, 2013, Jonathan Robert Cetti, et al.

15171784.0, Jun. 12, 2015, Lynette Anne Makins Holland, et al.

All Office Actions U.S. Appl. No. 14/567,192.

All Office Actions U.S. Appl. No. 15/175,836.

All Office Actions U.S. Appl. No. 15/183,363.

All Office Actions U.S. Appl. No. 15/175,865.

All Office Actions U.S. Appl. No. 14/705,373.

All Office Actions U.S. Appl. No. 14/105,230.

All Office Actions Applications Serial No. 15171784.0.

Moshel, et al., "Demonstrating Perfume Fixation", Perfumer & Flavorist, vol. 7, pp. 41-47, 1982.

PCT International Search Report dated Aug. 12, 2016—6 pages.

* cited by examiner

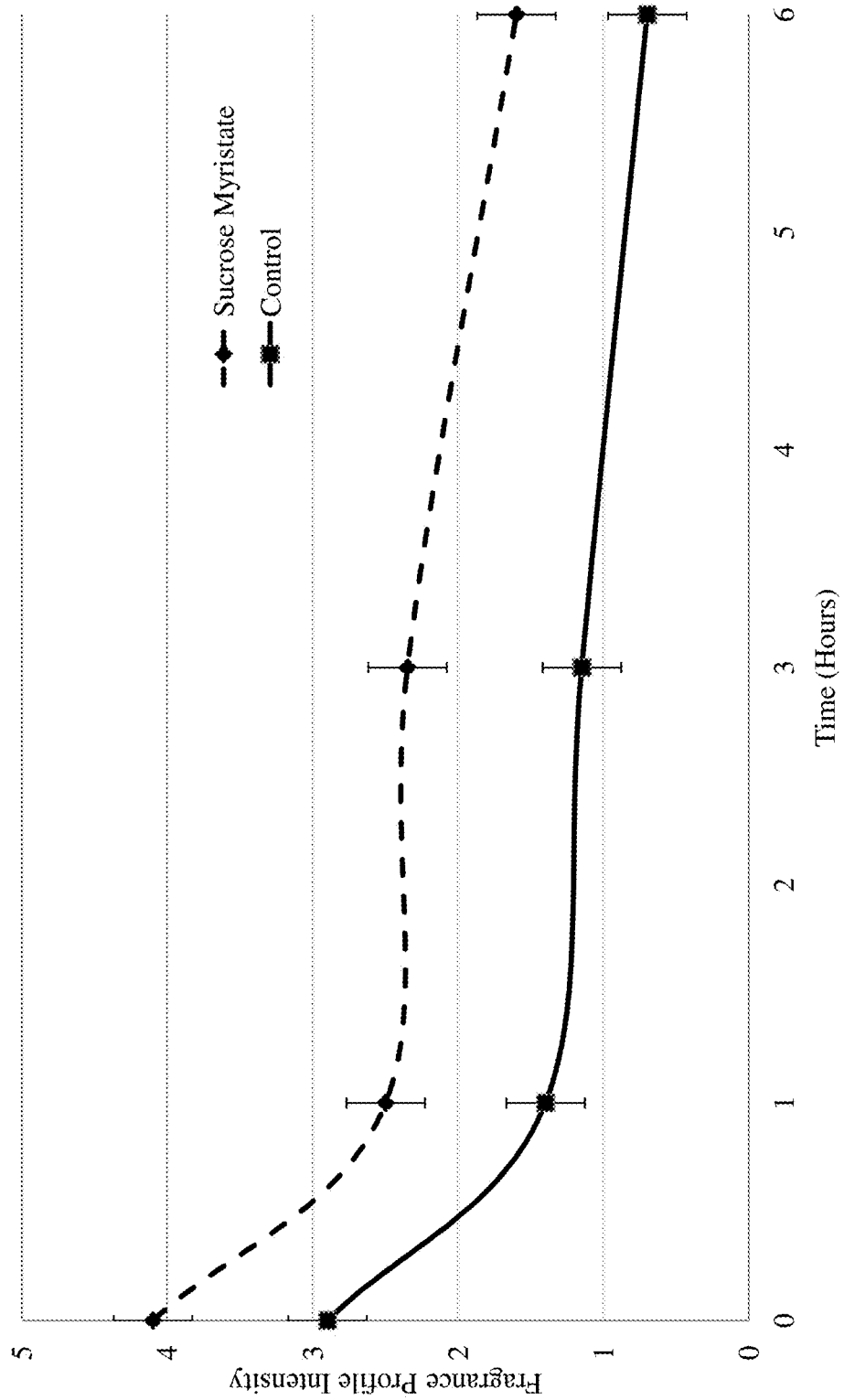

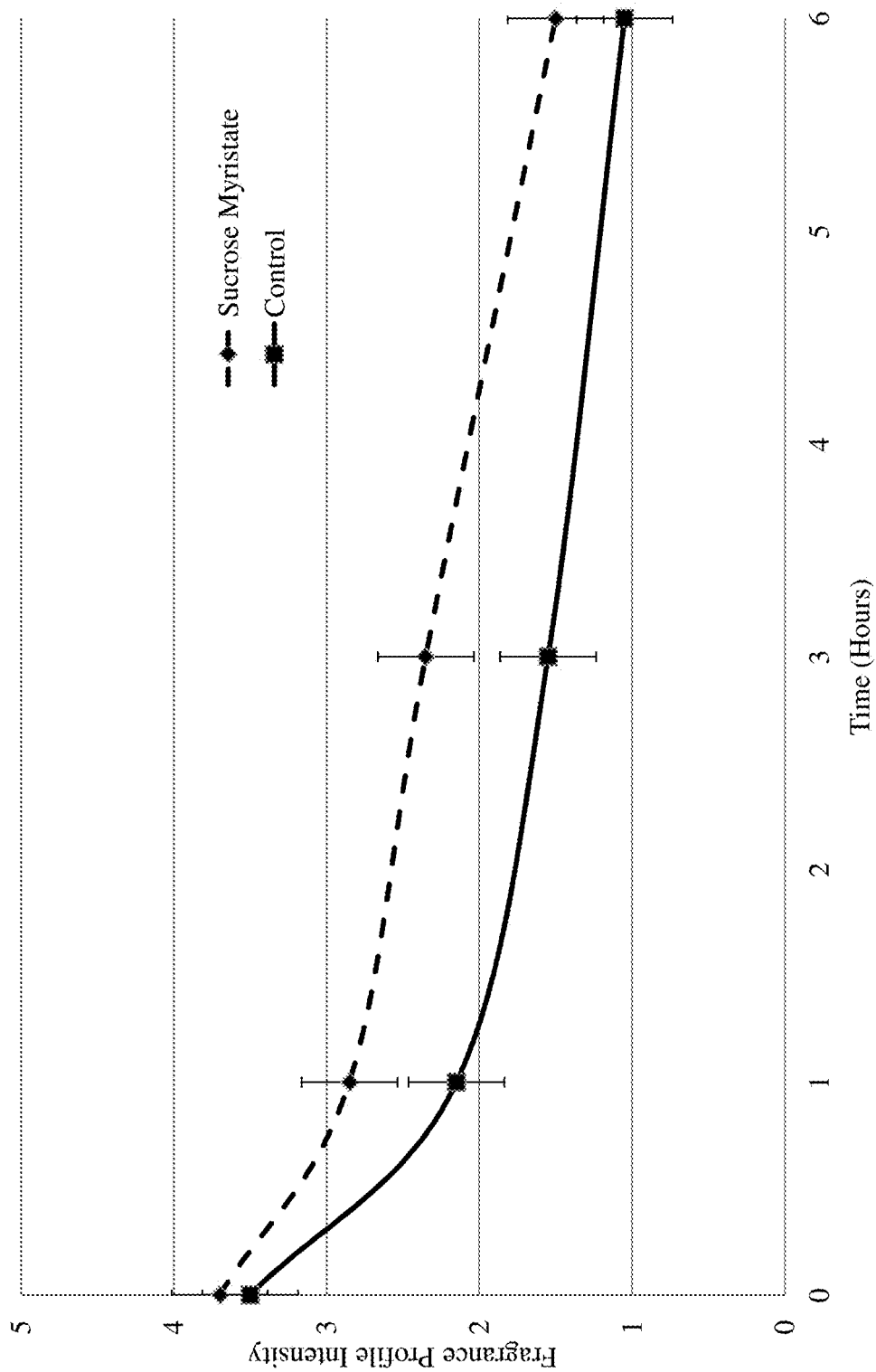

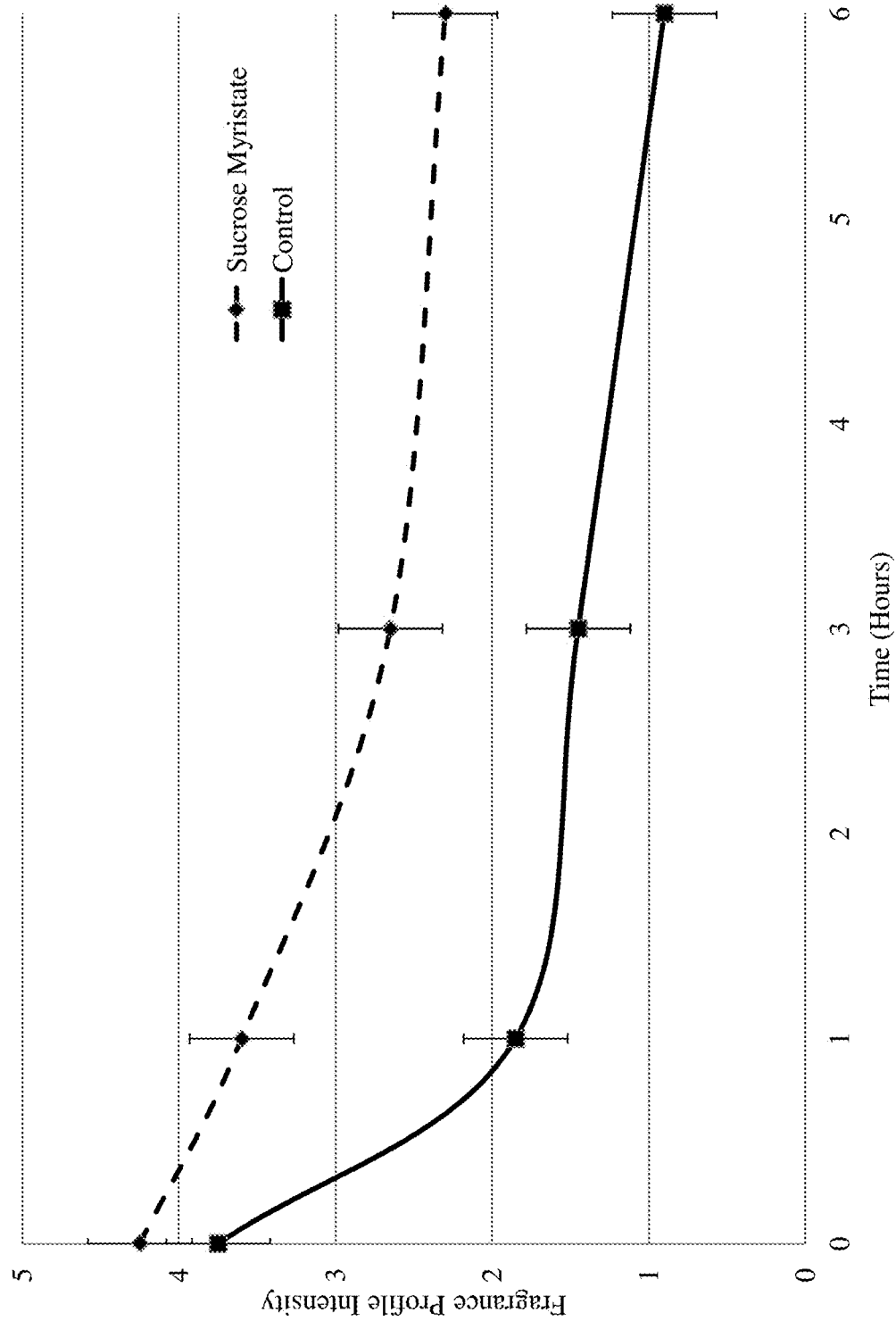

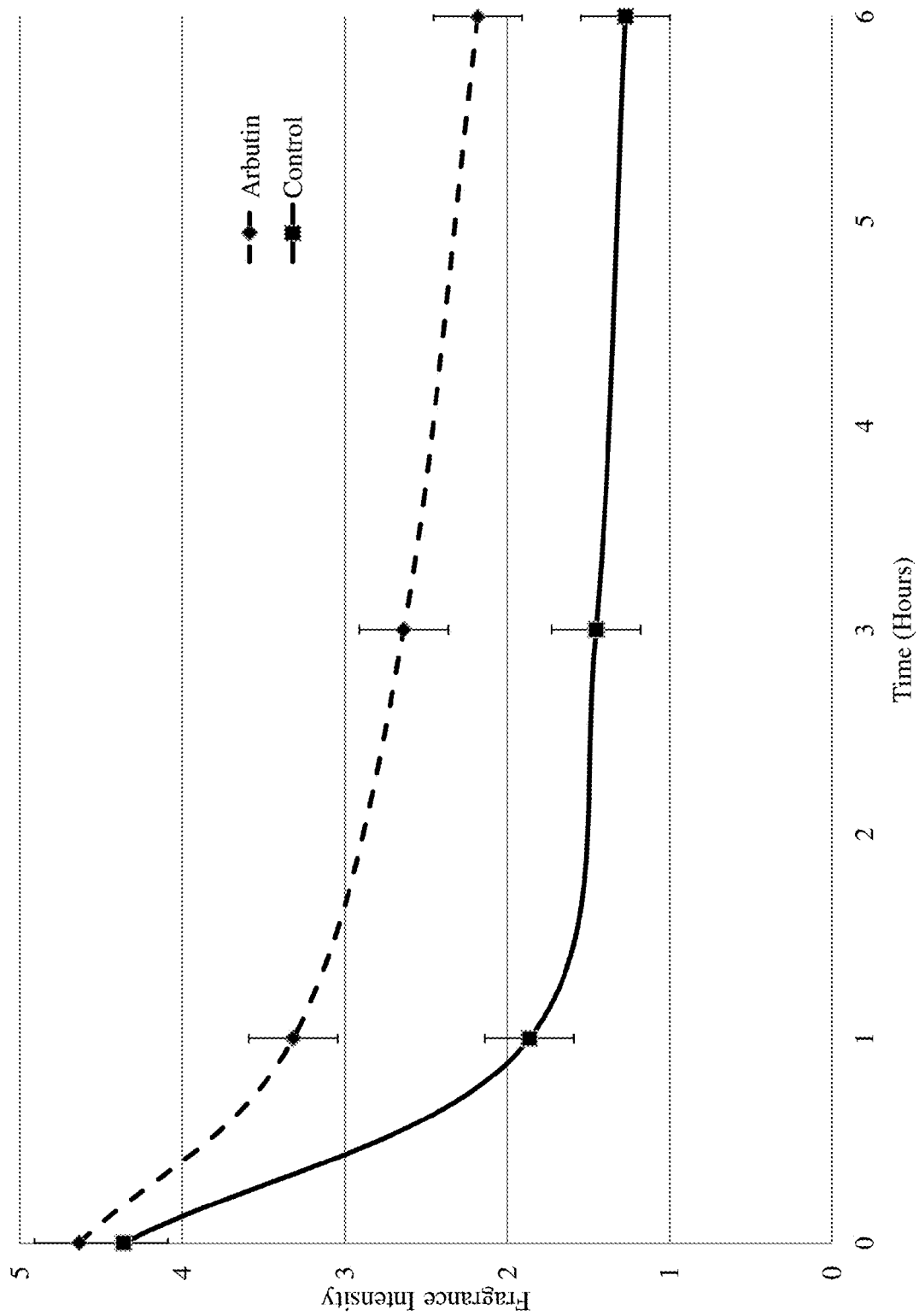

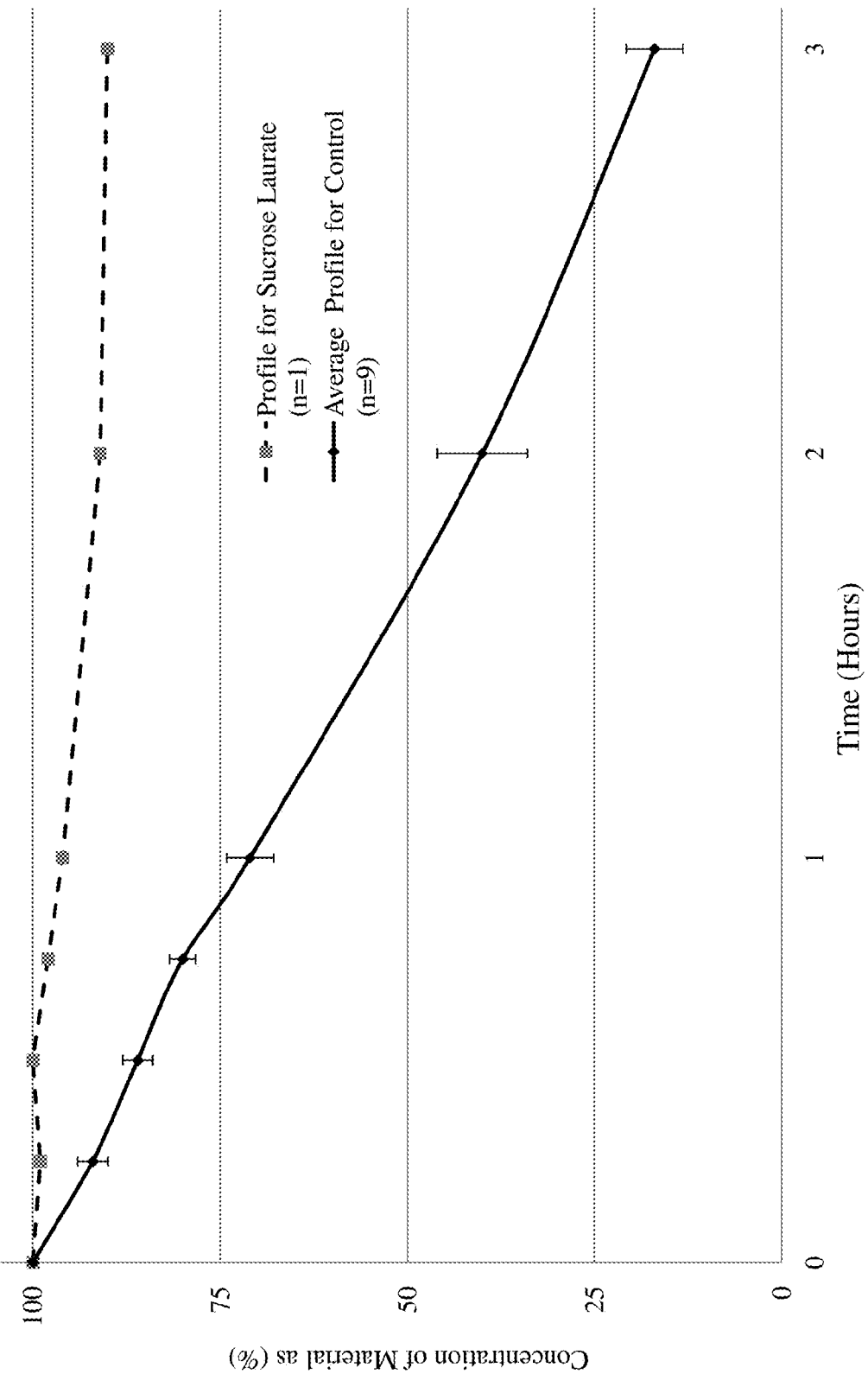

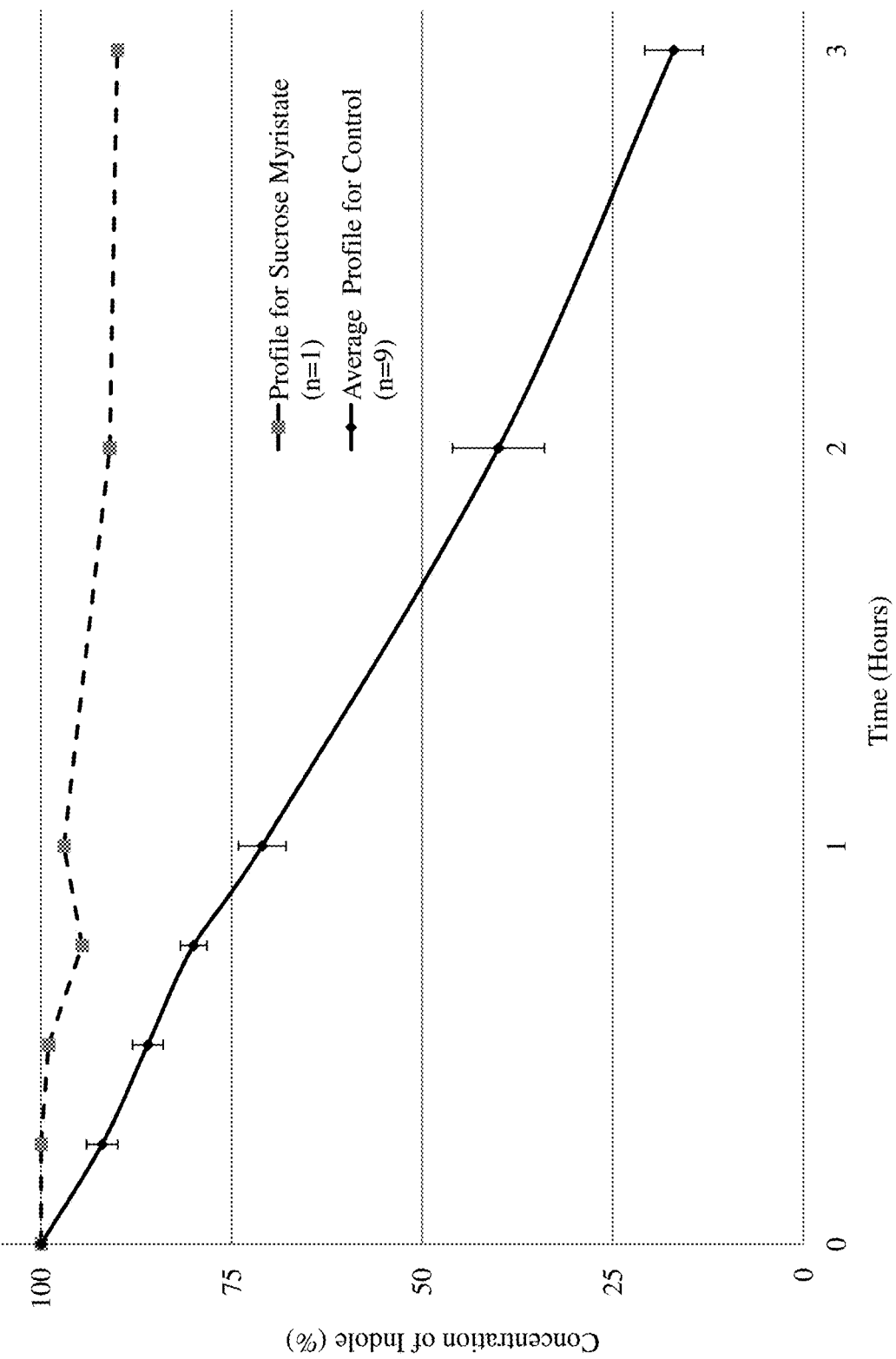

FRAGRANCE COMPOSITIONS AND USES THEREOF

FIELD OF THE INVENTION

The present invention relates to the field of perfumery. In particular, the compositions of the present invention have improved or enhanced fidelity and/or longevity of the fragrance profile.

BACKGROUND OF THE INVENTION

It has been a long tradition that highly skilled perfumers carefully select fragrance materials to blend into a composition with the goal of achieving an overall specific fragrance profile of strength and character. In so doing, they need to bear in mind differences in the individual character and volatility of the fragrance materials that are the components of the full fragrance. Conventional perfuming compositions have fragrance profile characterized by a high amount of the low volatile fragrance materials and lower amounts of the volatile fragrance materials. The low volatile fragrance materials are known as "base notes", while the volatile fragrance materials can be further divided into high volatile fragrance materials, identified as "top or head notes", and medium or moderate volatile fragrance materials, identified as "middle or heart notes". Perfumers typically classify fragrance materials as a base, heart or top note according to their specific characters. Unfortunately, there is no universal convention because this type of classification scheme tends to be subjective.

The top notes tend to smell citrusy, green, light, fresh, and comprise typically from about 0.1 wt % to 40 wt % relative to the total weight of the perfume formulation. Typically, perfumers use top notes to deliver the initial impression of the composition but do not rely on them to contribute much to its overall fragrance profile over time after application.

Middle or heart notes are associated with floral characters (e.g., jasmin, rose), fruity, marine, aromatic or spicy characters and make up from about 0.1 wt % to about 60 wt % relative to the total weight of the perfume formulation. Generally, they become dominant to the untrained nose from several minutes after application and can last up to a few hours afterwards.

Base or bottom notes are characterized as animalic, woody, sweet, amber or musky and can exist at greater than 30 wt % relative to the total weight of the perfume formulation. Typically, they are not perceived as dominant until several hours after the application of the perfume or during "dry-down". Base notes are relied upon at high levels to improve the strength of the overall fragrance profile over time and replace the heart notes when these are declining. The consequence of using base notes at high levels is that they impart particular odour characters, such as for example, musky, woody, ambery, warm and sweet, which overpower and dominate the fragrance character over time. Some of these base notes have become such common materials (e.g., ethylene brassylate, Galaxolide®, etc.) that many fragrance dry-downs appear repetitive, boring, non-memorable and un-interesting to consumers. However, if base notes are reduced or excluded then the fragrance strength weakens over time and does not last for a sufficient duration.

One problem with the above classification approach is that due to the somewhat subjective nature of characters, there is inconsistency with the construction of fragrance compositions. Another problem is that consumers tend to complain that middle notes tend to fade too quickly after application of the composition and that the character of the middle notes are undesirably altered by the presence of large amounts of the base notes during the period known as the "dry-down" phase.

Thus, it is desirable to provide new rules for objectively classifying fragrance materials according to their volatility using their vapor pressures defined at a suitable temperature, instead of their characters. The new rules operate irrespective of the perfumers performing the classification. In particular, the new rules classify the fragrance materials into low volatile fragrance materials or volatile fragrance materials for formulating into fragrance mixtures. It is further desirable to have a composition which retains a significant portion of its initial fragrance profile over time, hence, the floral, fruity, aromatic or spicy characters attributable to the volatile fragrance materials are perceived for many hours after application. It is also desirable that the fragrance profile of the composition remains noticeable to the consumer over longer periods of time. It is further desirable to be able to create new to the world fragrance profiles wherein one, or several, well-recognized volatile fragrance materials characters, are maintained over time.

It is therefore a challenge to formulate a composition having improved longevity of the fragrance profile, preferably characters attributable to the volatile fragrance materials, without having the fragrance profile substantially altered over time by the presence of the low volatile fragrance materials in the composition. One approach for addressing the challenge has been to formulate with higher proportions of perfume raw materials with a low volatility and which are therefore more substantive on the substrate. However, as discussed above, this restricts the type of fragrance profile that can be achieved over time.

Previous attempts to overcome these problems have been through the use of various "fixatives" or "modulators" to retard the evaporation of the more volatile fragrance ingredients present in fragrance compositions. For instance, U.S. Pat. No. 4,313,855 (Dragoco) describes the use in cosmetic compositions of 1-(2,6,6-trimethylcyclohexyl)-hexane-3-ol as an odourless fixative for increasing the perfume's intensity. U.S. Pat. No. 6,147,049 (Givaudan) discloses a perfume fixative derived from tera-hydronaphthalenese for use in a wide range of fragrance compositions. U.S. Pat. No. 6,440,400B1 (Takasago Perfumery) describes a composition using trimethylcyclohexane derivatives as perfuming-holding agents and melanin-formation inhibitors. U.S. Pat. No. 6,737,396B2 (Firmenich) describes a perfume composition formed by mixing 2-30%, relative to the weight of the composition, of a fixative, (1-ethoxyethoxy)cyclododecane, to fix or exalt the musky or aromatic-type notes. U.S. Pat. No. 7,538,081 (Takasago Perfumery) approaches the same problem of fixing a perfume and/or extending the perfume release from a fragrance composition. More particularly, said document describes the use of L-menthoxy ether derivatives as fixatives in fragrance compositions comprising at least one note selected from: floral, citrus, fruity, green, mint, herb and marine. JP Patent No. 61-083114 (Kanebo) describes ether derivatives as aroma-preserving agent for fine perfume composition. JP Patent No. 61-063612 (Kanebo) discloses diethylene glycol ether derivatives as fragrance adjusting agent showing effects as a fixative and a solubilizer. JP Patent No. 62-084010 (Shiseido) describes hydroquinone glycoside as perfume fixatives applicable for all kinds of perfume and blended perfume. On the other hand, PCT Publication No. WO85/04803 (Diagnostica) describes the use of hyaluronic acid/ hyaluronate as fixatives (via molecular encapsulation) in fragrance products to improve persistence of the fragrance.

There are at least one of several drawbacks to the above described use of fixatives or modulators in fragrance compositions. Firstly, these attempts, while disclosing compositions that retain the perfume by way of fixatives or modulators, do not teach the substantive reduction in the levels of low volatile fragrance materials in the fragrance compositions or the particular type of fragrance materials to include for delivering the benefits of improved fidelity and.or longevity of the fragrance profile, preferably the characters attributable from the volatile fragrance materials. Secondly, the use of fixatives or modulators in these attempts mostly shows effects on single perfume raw materials ("PRMs"), which are often not observed in a fragrance composition of a mixture of fragrance materials where a number of such fragrance materials are competing with each other to interact with said fixative or modulator. They do not teach how to formulate with fixatives or modulators in mixtures, which is not trivial. On the other hand, for other attempts that do describe mixtures, they have different fragrance design criteria and are directed to specific preferred fixative materials or modulators.

As such the previous attempts still have limitations, and do not adequately teach how to provide a composition wherein the prolonged fragrance profile, preferably the characters attributable to the volatile fragrance materials, are noticeable over time, preferably very long durations of time. Therefore, there remains a need for a composition that is perceived by the consumer over long, preferably very long, duration after application. There is also a need for a composition wherein the characters attributable to the volatile fragrance materials remains significantly consistent from its initial impression to the end. It is desirable that the compositions are relevant to fragrances derived from volatile fragrance materials having a vapor pressure greater than 0.001 Torr (0.000133 kPa) at 25° C.

SUMMARY OF THE INVENTION

The inventors have discovered new rules for objectively classifying fragrance materials according to their volatility, using their vapor pressures defined at a suitable temperature, into low volatile fragrance materials and volatile fragrance materials for formulating into fragrance mixtures. In a first aspect, the present invention is directed to a composition comprising a fragrance component present in an amount of from about 0.04 wt % to about 30 wt %, relative to the total weight of the composition, and wherein the fragrance component comprises at least one low volatile fragrance material having a vapor pressure less than 0.001 Torr (0.000133 kPa) at 25° C. and the low volatile fragrance material is present in an amount of from about 10 wt % to about 30 wt %, relative to the total weight of the fragrance component, and at least one substantially non-odorous fragrance modulator, as described herein below, present in an amount of from about 0.1 wt % to about 20 wt %, relative to the total weight of the composition.

In another aspect, the present invention is directed to a composition wherein the fragrance component further comprising one or more volatile fragrance materials having a vapor pressure greater than or equal to 0.001 Torr (0.000133 kPa) at 25° C. and present in the amount of from about 70 wt % to about 99.9 wt %, relative to the total weight of the fragrance component.

In yet another aspect, the present invention is further directed to a method of modifying or enhancing the odour properties of a body surface with a composition of the present invention, by contacting or treating the body surface with the composition.

These and other features of the present invention will become apparent to one skilled in the art upon review of the following detailed description when taken in conjunction with the appended claims.

BRIEF DESCRIPTION OF THE DRAWINGS

While the specification concludes with claims particularly pointing out and distinctly claiming the invention, it is believed that the invention will be better understood from the following description of the accompanying figures wherein:

FIG. 1 provides the panel test results of perceived fragrance profile, particularly improved fragrance profile longevity of Composition R comprising ethyl safranate fragrance material and sucrose myristate substantially non-odorous fragrance modulator as compared to Composition S, a control absent of a substantially non-odorous fragrance modulator (sucrose myristate), and as a function of time elapsed since application of the composition.

FIG. 2 provides the panel test results of perceived fragrance profile, particularly improved fragrance profile longevity of Composition P comprising dimethyl benzyl carbinol fragrance material and sucrose myristate substantially non-odorous fragrance modulator as compared to Composition Q, a control absent of a substantially non-odorous fragrance modulator (sucrose myristate), and as a function of time elapsed since application of the composition.

FIG. 3 provides the panel test results of perceived fragrance profile, particularly improved fragrance profile longevity of Composition T comprising phenethyl alcohol (PEA) and sucrose myristate substantially non-odorous fragrance modulator as compared to Composition U, a control absent of a substantially non-odorous fragrance modulator (sucrose myristate), and as a function of time elapsed since application of the composition.

FIG. 4 provides the panel test results of perceived fragrance profile, particularly improved fragrance profile longevity of Composition ZZ comprising eugenol and Hydroquinone beta-D-glycoside (Arbutin) substantially non-odorous fragrance modulator as compared to Composition ZZZ, a control absent of a substantially non-odorous fragrance modulator Hydroquinone beta-D-glycoside (Arbutin), and as a function of time elapsed since application of the composition.

FIG. 5 provides the evaporation profile results for a representative component (i.e., indole) of test composition (MOD1) comprising a volatile fragrance mixture and a sucrose laurate substantially non-odorous fragrance modulator as compared to a control composition (REF), and as a function of time elapsed since application of the composition.

FIG. 6 provides the evaporation profile results for a representative component (i.e., indole) of test composition (MOD2) comprising a volatile fragrance mixture and a sucrose myristate substantially non-odorous fragrance modulator as compared to a control composition (REF), and as a function of time elapsed since application of the composition.

DETAILED DESCRIPTION OF THE INVENTION

Definitions

As used herein, articles such as "a" and "an" when used in a claim, are understood to mean one or more of what is claimed or described.

As used herein, the terms "include", "includes" and "including" are meant to be non-limiting.

As used herein, the term "body splash" means a body care formulation that is applied to the body. Typically, the body splash is applied to the body after bathing and provides a subtle hint of scent to the body. Body splashes are commonly used by consumers who prefer less strong fragrance compositions. A body splash may comprise an ethanol-free composition according to the present invention which comprises from 0.2-8 wt %, relative to the total weight of the composition, of a fragrance component. The body splash may further comprise alkyl polyglucosides as non-ionic surfactants.

As used herein, the term "body spray" means a formulation comprising fragrance materials intended to be applied to the body to prevent or mask body odor caused by the bacterial breakdown of perspiration on the body (e.g., armpits, feet, and other areas of the body). The body spray may also provide a fragrance expression to the consumers. Typically, body spray compositions are applied as an aerosol spray in an effective amount on the skin of a consumer.

As used herein, the term "composition" includes a fine fragrance composition intended for application to a body surface, such as for example, skin or hair, i.e., to impart a pleasant odour thereto, or cover a malodour thereof. They are generally in the form of perfume concentrates, perfumes, parfums, eau de parfums, eau de toilettes, aftershaves, colognes, body splashes, or body sprays. The fine fragrance compositions may be an ethanol-based composition. The term "composition" may also include a cosmetic composition, which comprises a fragrance material for the purposes of delivering a pleasant smell to drive consumer acceptance of the cosmetic composition. The term "composition" may also include cleaning compositions, such as fabric care composition or home care compositions, including air care compositions (e.g., air fresheners), for use on clothing or other substrates such as hard surfaces (e.g., dishes, floors, countertops). Additional non-limiting examples of "composition" may also include facial or body powder, foundation, deodorant, body/facial oil, mousse, creams (e.g., cold creams), waxes, sunscreens and blocks, bath and shower gels, lip balms, self-tanning compositions, masks and patches.

As used herein, the term "consumer" means both the user of the composition and the observer nearby or around the user.

As used herein, the terms "fragrance" and "perfume" are used interchangeably to designate the component in the composition that is formed of fragrance materials, i.e., ingredients capable of imparting or modifying the odour of skin or hair or other substrate.

As used herein, the term "fragrance material" and "fragrance materials" relates to a perfume raw material, or a mixture of perfume raw materials, that are used to impart an overall pleasant odour or fragrance profile to a composition. "Fragrance materials" can encompass any suitable perfume raw materials for fragrance uses, including materials such as, for example, alcohols, aldehydes, ketones, esters, ethers, acetates, nitriles, terpene hydrocarbons, nitrogenous or sulfurous heterocyclic compounds and essential oils. However, naturally occurring plant and animal oils and exudates comprising complex mixtures of various chemical components are also know for use as "fragrance materials". The individual perfume raw materials which comprise a known natural oil can be found by reference to Journals commonly used by those skilled in the art such as "Perfume and Flavourist" or "Journal of Essential Oil Research", or listed in reference texts such as the book by S. Arctander, *Perfume and Flavor Chemicals,* 1969, Montclair, N.J., USA and more recently re-published by Allured Publishing Corporation Illinois (1994). Additionally, some perfume raw materials are supplied by the fragrance houses (Firmenich, International Flavors & Fragrances, Givaudan, Symrise) as mixtures in the form of proprietary specialty accords. Non-limiting examples of the fragrance materials useful herein include pro-fragrances such as acetal pro-fragrances, ketal pro-fragrances, ester pro-fragrances, hydrolyzable inorganic-organic pro-fragrances, and mixtures thereof. The fragrance materials may be released from the pro-fragrances in a number of ways. For example, the fragrance may be released as a result of simple hydrolysis, or by a shift in an equilibrium reaction, or by a pH-change, or by enzymatic release.

As used herein, the term "fragrance profile" means the description of how the fragrance is perceived by the human nose at any moment in time. The fragrance profile may change over time. It is a result of the combination of the low volatile fragrance materials and the volatile fragrance materials, if present, of a fragrance. A fragrance profile is composed of 2 characteristics: 'intensity' and 'character'. The 'intensity' relates to the perceived strength whilst 'character' refers to the odour impression or quality of the perfume, i.e., fruity, floral, woody, etc.

As used herein, the terms "modulator" and "fragrance modulator" are used interchangeably to designate an agent having the capacity to affect the fragrance profile, such as for example, by impacting the fragrance materials' evaporation rate. The modulator may mediate its effect by lowering the vapor pressure of the fragrance materials and increasing their adherence to the substrate (skin and/or hair) thus ensuring a longer-lasting impression of the fragrance. By incorporating the modulator, it is desired that the fragrance profile, preferably the fragrance characters attributable to the volatile fragrance materials, of the composition can be perceived by a consumer, over a longer period of time, as compared to the same perception in the absence of the modulator. Suitable examples of the modulator are provided herein below. However, as discovered by the inventors, simply adding modulators to a traditionally constructed fragrance composition will not ensure an improved or enhanced fidelity and/or longevity of the fragrance profile over time. Instead, it is only when the modulators are added in the presence of reduced levels of low volatile fragrance materials can the improved or enhanced fidelity and/or longevity of the fragrance profile, preferably attributable to the volatile fragrance materials, be perceived as compared to control composition absent the modulators and low levels of low volatile fragrance materials.

As used herein, the term "substantially non-odorous" means an agent that does not impart an odour of its own when added into a composition of the present invention. For example, a "substantially non-odorous fragrance modulator" does not impart a new odour that alters the character of the fragrance profile of the composition to which it is added. The term "substantially non-odorous" also encompasses an agent that may impart a minimal or slight odour of its own when added into a composition of the present invention. However, the odour imparted by the "substantially non-odorous fragrance modulator" is generally undetectable or tends to not substantively alter the character of the fragrance profile of the composition to which it is added initially or preferably over time. Furthermore, the term "substantially non-odorous" also includes materials that are perceivable only by a minority of people or those materials deemed anosmic to the majority of people. Furthermore, the term "substantially non-odorous" also includes materials that may, from particular suppliers, contain an odour due to impurities, such as when the materials contain the impurities at not more than about 5 wt %, preferably not more than 1 wt %, often even not more than 1 part per million (ppm). These impurities maybe removed by purification techniques known in the art as required to make them suitable for use in fragrance compositions of the present invention.

As used herein, the term "vapor pressure" means the partial pressure in air at a defined temperature (e.g., 25° C.) and standard atmospheric pressure (760 mmHg) for a given chemical species. It defines a chemical species' desire to be in the gas phase rather than the liquid or solid state. The higher the vapor pressure the greater the proportion of the material that will, at equilibrium, be found in a closed headspace. It is also related to the rate of evaporation of a fragrance material which is defined in an open environment where material is leaving the system. The vapor pressure is determined according to the reference program Advanced Chemistry Development (ACD/Labs) Software Version 14.02, or preferably the latest version update).

It is understood that the test methods that are disclosed in the Test Methods Section of the present application must be used to determine the respective values of the parameters of Applicants' inventions as described and claimed herein.

In all embodiments of the present invention, all percentages are by weight of the total composition, as evident by the context, unless specifically stated otherwise. All ratios are weight ratios, unless specifically stated otherwise, and all measurements are made at 25° C., unless otherwise designated.

Compositions

The inventors have surprisingly discovered a revolutionary new way of objectively classifying fragrance materials and then formulating those fragrance materials into complex fragrance mixtures having improved fragrance profile fidelity and longevity. Essentially, the solution is to formulate the fragrance materials having low levels (10 to 30 wt % relative to the total weight of the fragrance component) of the low volatile fragrance materials in the presence of a substantially non-odorous fragrance modulator to provide for improved or enhanced longevity and/or fidelity of the fragrance profile, particularly amongst characters attributable to volatile fragrance materials. In fact, the inventors have discovered that in the complete absence of the low volatile fragrance materials or at very low levels of the low volatile fragrance materials (less than 10 wt % relative to the total weight of the fragrance component), there is insufficient character complexity and roundness of the fragrance profile for consumer acceptance of the composition. Therefore the level of low volatile fragrance materials needs to be carefully chosen between 10 and 30 wt % to balance consumer acceptance and the desired improved or enhanced longevity and/or fidelity of the fragrance profile, particularly amongst characters attributable to volatile fragrance materials.

Specifically, in one aspect, the present invention provides for a composition comprising a fragrance component present in an amount of from about 0.04 wt % to 30 wt %, preferably 1 wt % to about 30 wt %, more preferably less than about 25 wt %, yet more preferably less than about 20 wt %, yet even more preferably less than about 15 wt %, yet even more preferably less than about 10 wt % or most preferably less than about 8 wt %, relative to the total weight of the composition. Alternatively, the fragrance component is present in an amount of from about 0.04 wt %, 0.3 wt %, 1 wt %, 2 wt %, 5 wt %, 8 wt % or 10 wt %, to about 15 wt %, 20 wt %, 25 wt % or 30 wt %, relative to the total weight of the composition.

(i) Low Volatile Fragrance Materials

Further, the fragrance component comprises at least one low volatile fragrance material having a vapor pressure less than 0.001 Torr (0.000133 kPa) at 25° C. Unlike previous proposed classification of fragrance materials according to their characters, which tends to be subjective, the inventors have established new rules to objectively classifying fragrance materials into low volatile fragrance materials or volatile fragrance materials according to their vapor pressure. For example, methyl dihydrojasmonate which has been typically classified as a heart note under the traditional approach is now classified as a low volatile fragrance material because it has a vapor pressure of 0.00071000 Torr (0.000095 kPa) at 25° C. This new classification better reflects methyl dihydrojasmonate's technical properties of slow evaporation and long lasting properties.

Preferably the composition according to the present invention comprises at least 3 low volatile fragrance materials, or least 5 low volatile fragrance materials. It is preferred that the composition of the present invention comprises low, preferably very low levels of the low volatile fragrance materials, lower than would traditionally be present in a composition. As such, compositions of the present invention can comprise low levels of the low volatile fragrance material present in an amount of from about 10 wt % to about 30 wt %, preferably less than about 30 wt %, or preferably less than about 29 wt %, or preferably less than about 28 wt %, or preferably less than about 27 wt %, or preferably less than about 26 wt %, or preferably less than about 25 wt %, relative to the total weight of the fragrance component. Alternatively, the low volatile fragrance material is present in an amount of from about 10 wt %, 12 wt %, 15 wt %, 20 wt %, 25 wt %, 28 wt % or 30 wt %, relative to the total weight of the fragrance component. If there is more than one low volatile fragrance materials, then the ranges provided hereinabove cover the total of all of the low volatile fragrance materials. Preferable examples of low volatile fragrances materials are provided in Table 1 below.

(ii) Fragrance Modulators

The composition further comprises at least one substantially non-odorous fragrance modulator as described herein below. Preferable examples of the substantially non-odorous fragrance modulators are provided in Table 3 below.

Preferably, the substantially non-odorous fragrance modulator is present in an amount of from about 0.1 wt % to about 20 wt %, preferably from about 0.5 wt % to about 18 wt % or more preferably from about 2.5 wt % to about 15 wt % or combinations thereof, relative to the total weight of the composition. Alternatively, the substantially non-odorous fragrance modulator is present in an amount of from about 0.1 wt %, 0.5 wt % or 2.5 wt % to about 15 wt %, 18 wt % or 20 wt %, relative to the total weight of the composition. If there is more than one substantially non-odorous fragrance modulators, then the ranges provided hereinabove cover the total of all of the substantially non-odorous fragrance modulators.

The substantially non-odorous modulator of the present invention may be a liquid at temperatures lower than 100° C., preferably at ambient temperature. The substantially non-odorous modulators may be fully miscible with the PRMs to form a single phase liquid. However, if the PRMs are not entirely miscible, or are immiscible, then co-solvents (e.g., dipropylene glycol (DPG), triethyl citrate, or others as well known to those skilled in the art) can be added to aid in the solubility of the PRMs.

Preferably, the composition according to the present invention, wherein the substantially non-odorous fragrance modulator does not comprise: (i) isocetyl alcohol, PPG-3 myristyl ether, neopentyl glycol diethylhexanoate or their mixtures; and (ii) n-hexadecyl n-nonanoate, n-octadecyl n-nonanoate or their mixtures.

Preferably, the composition according to the present invention, wherein the substantially non-odorous fragrance modulator and fragrance component are present in a weight ratio from about 3:1 to about 1:3.

The inventors have surprisingly discovered that by reducing the levels of the low volatile fragrance materials, and preferably increasing the levels of the volatile fragrance materials, in a composition, the effect of the substantially non-odorous modulator on the fragrance profile, particularly the portion of the fragrance profile attributable to the volatile fragrance materials, can be improved. By "improved" it is meant that the fragrance profile of the composition, particular the components contributed by the volatile fragrance materials, can be pereceived by the consumer at later time points such as for example, 2 hours, 3 hours, 4 hours, 5 hours, 6 hours, 7 hours, 8 hours, 10 hours, and possibly all the way up to 24 hrs after application as compared to controls, i.e., compositions containing normal or high levels of the low volatile fragrance materials (i.e., at least greater than 30 wt % relative to the total weight of the fragrance component) and the substantially non-odorous modulator or compositions containing reduced levels of low volatile fragrance materials and no substantially non-odorous modulator.

Alternatively, by "improved" it can mean that the olfactive perception, by the consumer, of the fidelity of the fragrance profile contributed by the volatile fragrance materials is markedly increased or enhanced as compared to the controls. "Increased" or "enhanced" means that the consumer perceives the fragrance profile, preferably the characters attributable to the volatile fragrance materials, of a composition as not changing from its initial impression or the changes are minimal from when the composition was first applied to when it dissipates. In other words, the fidelity of the perceived fragrance profile of the composition is maintained over time.

Typically, it has been very difficult to formulate fragrance profile, particularly a floral or an aromatic or a spicy character of the volatile fragrance materials, which can last for very long periods, especially throughout the life of the composition after its application, without giving way to the stronger characters of the low volatile fragrance materials. The present invention of reducing levels of the low volatile fragrance materials with the substantially non-odorous modulators will allow perfumers to increase the perception of the volatile perfume materials, to create new characters, and to address a re-occurring consumer issue that particular fragrance profiles, particularly those having floral or aromatic or spicy characters, do not last long enough.

Such a solution as presented herein provides enhanced or improved fidelity and/or longevity of the fragrance profile, particularly amongst those composition formulated from volatile fragrance materials having medium to high vapor pressure ranges (greater than or equal to 0.001 Torr (0.000133 kPa) at 25° C.), without having to rely on the presence or significant amounts of the low volatile fragrance materials, which has a tendency to overpower and alter the overall character of a fragrance, particularly over time. As a result, the present invention provides the perfumer options to formulate compositions having new fragrance profiles not possible before.

(iii) Volatile Fragrance Materials

In another aspect, the present invention also provides a composition, wherein the fragrance component further comprising one or more volatile fragrance materials having a vapor pressure greater than or equal to 0.001 Torr (0.000133 kPa) at 25° C. The volatile fragrance material is present in an amount of from about 70 wt % to about 99.9 wt %, preferably greater than about 80 wt %, or more preferably greater than 88 wt %, or combinations thereof, relative to the total weight of the fragrance component. Alternatively, the volatile fragrance material is present in an amount of from about 70 wt %, 73 wt %, 75 wt %, 80 wt %, 85 wt %, 88 wt %, or 90 wt %, relative to the total weight of the fragrance component. If there is more than one volatile fragrance materials, then the ranges provided hereinabove cover the total weight of all of the volatile fragrance materials. Preferable examples of volatile fragrances materials are provided in Table 2 below.

Preferably, the volatile fragrance materials can be divided into: (i) a high volatile fragrance material having a vapor pressure greater than 0.1 Torr (0.0133 kPa) at 25° C., present in an amount of from about 1 wt % to about 30 wt %, relative to the total weight of the fragrance component, and (ii) a moderate volatile fragrance material having a vapor pressure in the range of from 0.1 Torr to 0.001 Torr (0.0133 kPa to 0.000133 kPa) at 25° C., present in an amount of from about 40 wt % to about 80 wt %, relative to the total weight of the fragrance component. While the further classification of the volatile fragrance materials into high and moderate volatile fragrance materials is provided to help illustrate the fragrance characters of the perfume raw materials and is useful for when it comes to formulating new fragrance profiles, it should not be construed as limiting on what qualifies as a volatile fragrance material.

Entrapment Materials

In yet another aspect, compositions of the present invention may comprise an entrapment material at a level such that the weight ratio of the entrapment material to the fragrance materials is in the range of from about 1:20 to about 20:1. Preferably, the composition may comprise an entrapment material present in the amount of from about 0.001 wt % to about 40 wt %, from about 0.1 wt % to about 25 wt %, from about 0.3 wt % to about 20 wt %, from about 0.5 wt % to about 10 wt %, or from about 0.75 wt % to about 5 wt %, relative to the total weight of the composition. The compositions disclosed herein may comprise from 0.001 wt % to 40%, from 0.1 wt % to 25 wt %, from 0.3 wt % to 20 wt %, from 0.5 wt % to 10 wt % or from 0.75 wt % to 5 wt %, relative to the total weight of the composition, of a cyclic oligosaccharide.

Suitable entrapment materials for use herein are selected from polymers; capsules, microcapsules and nanocapsules; liposomes, absorbents; cyclic oligosaccharides and mixtures thereof. Preferred are absorbents and cyclic oligosaccharides and mixtures thereof. Highly preferred are cyclic oligosaccharides (see PCT Publication Nos. WO2000/67721 (Procter & Gamble); and WO2000/67720 (Procter & Gamble); and U.S. Pat. No. 6,893,647 (Procter & Gamble)).

As used herein, the term "cyclic oligosaccharide" means a cyclic structure comprising six or more saccharide units. Preferred for use herein are cyclic oligosaccharides having six, seven or eight saccharide units and mixtures thereof, more preferably six or seven saccharide units and even more preferably seven saccharide units. It is common in the art to abbreviate six, seven and eight membered cyclic oligosaccharides to α, β and γ respectively.

The cyclic oligosaccharide of the compositions used for the present invention may comprise any suitable saccharide or mixtures of saccharides. Examples of suitable saccharides include, but are not limited to, glucose, fructose, mannose, galactose, maltose and mixtures thereof. However, preferred for use herein are cyclic oligosaccharides of glucose. The preferred cyclic oligosaccharides for use herein are α-cyclodextrins or β-cyclodextrins, or mixtures thereof, and the most preferred cyclic oligosaccharides for use herein are β-cyclodextrins.

The cyclic oligosaccharide, or mixture of cyclic oligosaccharides, for use herein may be substituted by any suitable substituent or mixture of substituents. Herein the use of the term "mixture of substituents" means that two or more different suitable substituents can be substituted onto one cyclic oligosaccharide. The derivatives of cyclodextrins consist mainly of molecules wherein some of the OH groups have been substituted. Suitable substituents include, but are not limited to, alkyl groups; hydroxyalkyl groups; dihydroxyalkyl groups; (hydroxyalkyl)alkylenyl bridging groups such as cyclodextrin glycerol ethers; aryl groups; maltosyl groups; allyl groups; benzyl groups; alkanoyl groups; cationic cyclodextrins such as those containing 2-hydroxy-3-(dimethylamino) propyl ether; quaternary ammonium groups; anionic cyclodextrins such as carboxyalkyl groups, sulphobutylether groups, sulphate groups, and succinylates; amphoteric cyclodextrins; and mixtures thereof.

The substituents may be saturated or unsaturated, straight or branched chain. Preferred substituents include saturated and straight chain alkyl groups, hydroxyalkyl groups and mixtures thereof. Preferred alkyl and hydroxyalkyl substituents are selected from $C_1$-$C_8$ alkyl or hydroxyalkyl groups or mixtures thereof, more preferred alkyl and hydroxyalkyl substituents are selected from $C_1$-$C_6$ alkyl or hydroxyalkyl groups or mixtures thereof, even more preferred alkyl and hydroxyalkyl substituents are selected from $C_1$-$C_4$ alkyl or hydroxyalkyl groups and mixtures thereof. Especially preferred alkyl and hydroxyalkyl substituents are propyl, ethyl and methyl, more especially hydroxypropyl and methyl and even more preferably methyl.

Preferred cyclic oligosaccharides for use in the present invention are unsubstituted, or are substituted by only saturated straight chain alkyl, or hydroxyalkyl substituents. Therefore, preferred examples of cyclic oligosaccharides for use herein are α-cyclodextrin, β-cyclodextrin, methyl-α-cyclodextrin, methyl-β-cyclodextrin, hydroxypropyl-α-cyclodextrin and hydroxypropyl-β-cyclodextrin. Most preferred examples of cyclic oligosaccharides for use herein are methyl-α-cyclodextrin and methyl-β-cyclodextrin. These are available from Wacker-Chemie GmbH Hanns-Seidel-Platz 4, Munchen, D E under the tradename Alpha W6 M and Beta W7 M respectively. Especially preferred is methyl-β-cyclodextrin.

The cyclic oligosaccharides of the compositions used for the present invention are preferably soluble in water, ethanol, or both water and ethanol. As used herein "soluble" means at least about 0.1 g of solute dissolves in 100 mL of solvent, at 25° C. and standard atmospheric pressure (760 mmHg). Preferably the cyclic oligosaccharides for use herein have a solubility of at least about 1 g/100 mL, at 25° C. and 1 atm of pressure. Preferred is that cyclic oligosaccharides are only present at levels up to their solubility limits in a given composition at room temperature. A person skilled in the art will recognise that the levels of cyclic oligosaccharides used in the present invention will also be dependent on the components of the composition and their levels, for example the solvents used or the exact fragrance oils, or combination of fragrance oils, present in the composition. Therefore, although the limits stated for the entrapment material are preferred, they are not exhaustive.

Volatile Solvents

In yet another aspect, the present invention provides the solution to the problem of extending the longevity of the fragrance profile of compositions, particularly fine fragrance and cosmetic compositions, preferably fine fragrance compositions, which commonly contain high levels of a volatile solvent. Preferably, the composition according to the present invention, further comprising a volatile solvent present in the amount of from about 50 wt % to about 80 wt %, or preferably from about 55 wt % to about 75 wt %, relative to the total weight of the composition, and wherein the solvent is a branch or unbranched $C_1$ to $C_{10}$ alkyl, akenyl or alkynyl group having at least one alcohol moiety, preferably ethanol, or isopropanol, or other alcohols (e.g., methanol, propanol, isopropanol, butanol, and mixtures thereof) commonly found in commercial fine fragrance products.

Accordingly, ethanol may be present in any of the compositions of the present invention, and more specifically, it will form from about 10 wt % to about 80 wt %, or even from about 25 wt % to about 75 wt % of the composition, or combinations thereof, relative to the total weight of the composition. Alternatively, ethanol may be present in an amount of from about 10 wt % or 25 wt % to about 75 wt % or 80 wt %, relative to the total weight of the composition. The ethanol useful in the present invention may be any acceptable quality of ethanol, compatible and safe for the specific intended use of the composition such as, for example, topical applications of fine fragrance or cosmetic compositions.

Non-Volatile Solvents

The composition may comprise a non-volatile solvent or a mixture of non-volatile solvents. Non-limiting examples of non-volatile solvents include benzyl benzoate, diethyl phthalate, isopropyl myristate, propylene glycol, dipropylene glycol, triethyl citrate, and mixtures thereof. These solvents often are introduced to the product via the perfume oil as many perfume raw materials may be purchased as a dilution in one of these solvents. Where non-volatile solvents are present, introduced either with the perfume materials or separately, then for the purposes of calculating the proportion of fragrance component having a vapor pressure of less than 0.001 Torr (0.000133 kPa) at 25° C. the total fragrance components does not include non-volatile solvents. Where non-volatile solvents are present, introduced either with the perfume materials or separately, then for the purposes of calculating the total level of fragrance component this does not include such non-volatile solvents. In addition if present with cyclic oligosacchrides, the non-volatile solvent may be included at a weight ratio of the non-volatile solvent to the cyclic oligosaccharide of less than 1:1, less than 1:2, less than 1:10, or less than 1:100.

Water

In yet another aspect, water may be present in any of the compositions of the present invention, and more specifically, it shall not exceed about 40 wt %, preferably about 20 wt % or less, or more preferably about 10 wt % or less, relative to the total weight of the composition. Alternatively, water may be present in an amount of from about 10 wt % or about 20 wt % to about 40 wt %, relative to the total weight of the composition. When the composition is a cosmetic composition the level of water should not be so high that the product becomes cloudy thus negatively impacting the product aesthetics. It is understood that the amount of water present in the composition may be from the water present in the volatile solvent (e.g., ethanol) used in the composition, as the case may be.

Propellants

The compositions described herein may include a propellant. Some examples of propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutane and n-butane), AP30 (a mixture of propane, isobutane and n-butane), and 152A (1,1 diflouroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42% by weight of the total fill of materials stored within the container.

Antiperspirant Active

The compositions described herein may be free of, substantially free of, or may include an antiperspirant active (i.e., any substance, mixture, or other material having antiperspirant activity). Examples of antiperspirant actives include astringent metallic salts, like the inorganic and organic salts of aluminum, zirconium and zinc, as well as mixtures thereof. Such antiperspirant actives include, for example, the aluminum and zirconium salts, such as aluminum halides, aluminum hydroxyhalides, zirconyl oxyhalides, zirconyl hydroxyhalides, and mixtures thereof.

Other Ingredients

In yet another aspect, the composition consists essentially of the recited ingredients but may contain small amounts (not more than about 10 wt %, preferably no more than 5 wt %, or preferably no more than 2 wt % thereof, relative to the total weight of the composition) of other ingredients that do not impact on the fragrance profile, particularly the evaporation rate and release of the fragrance materials. For example, a fine fragrance composition may comprise stabilizing or anti-oxidant agents, UV filters or quenchers, or colouring agents, commonly used in perfumery. There are a number of other examples of additional ingredients that are suitable for inclusion in the present compositions, particularly in compositions for cosmetic use. These include, but are not limited to, alcohol denaturants such as denatonium benzoate; UV stabilisers such as benzophenone-2; antioxidants such as tocopheryl acetate; preservatives such as phenoxyethanol, benzyl alcohol, methyl paraben, and propyl paraben; dyes; pH adjusting agents such as lactic acid, citric acid, sodium citrate, succinic acid, phosphoric acid, sodium hydroxide, and sodium carbonate; deodorants and antimicrobials such as farnesol and zinc phenolsulphonate; humectants such as glycerine; oils; skin conditioning agents such as allantoin; cooling agents such as trimethyl isopropyl butanamide and menthol; silicones; solvents such as hexylene glycol; hair-hold polymers such as those described in PCT Publication No. WO94/08557 (Procter & Gamble); salts in general, such as potassium acetate and sodium chloride and mixtures thereof.

In yet another aspect, the composition of the present invention, depending on its intended use, is a mixture of fragrance materials possibly together with other ingredients such as, for example, perfume carriers. By the term "perfume carrier", it is meant to include materials which are practically neutral from a perfumery point of view, i.e., which does not significantly alter the organoleptic properties of perfuming components. The perfume carrier may be a compatible liquid or solid fillers, diluents, and the like. The term "compatible", as used herein, means that the components of the compositions of this invention are capable of being combined with the primary actives of the present invention, and with each other, in a manner such that there is no interaction which would substantially reduce the efficacy of the composition under ordinary use situations. The type of carrier utilized in the present invention depends on the type of product desired and may comprise, but are not limited to, solutions, aerosols, emulsions (including oil-in-water or water-in-oil), gels, and liposomes. Preferably, the carrier is a liquid and will be a solvent such as, for example, dipropyleneglycol, diethyl phthalate, isopropyl myristate, benzyl benzoate, 2-(2-ethoxyethoxy)-1-ethanol, or ethyl citrate (triethyl citrate).

In yet another aspect, the compositions for use in the present invention may take any form suitable for use, more preferably for perfumery or cosmetic use. These include, but are not limited to, vapor sprays, aerosols, emulsions, lotions, liquids, creams, gels, sticks, ointments, pastes, mousses, powders, granular products, substrates, cosmetics (e.g., semi-solid or liquid makeup, including foundations) and the like. Preferably the compositions for use in the present invention take the form of a vapor spray. Compositions of the present invention can be further added as an ingredient to other compositions, preferably fine fragrance or cosmetic compositions, in which they are compatible. As such they can be used within solid composition or applied substrates etc.

Preferably, the compositions of the present invention comprise:
  (i) a fragrance component present in an amount of from about 0.04 wt % to about 30 wt %, relative to the total weight of the composition, and wherein the fragrance component comprises:
    (a) at least one low volatile fragrance material having a vapor pressure less than 0.001 Torr (0.000133 kPa) at 25° C., present in the amount of from about 10 wt % to about 30 wt %, relative to the total weight of the fragrance component; and
    (b) at least one volatile fragrance material having a vapor pressure greater than or equal to 0.001 Torr (0.000133 kPa) at 25° C., present in the amount of from about 70 wt % to about 99.9 wt %, relative to the total weight of the fragrance component; and
  (ii) at least one substantially non-odorous fragrance modulator present in the amount of from about 0.1 wt % to about 20 wt %, relative to the total weight of the composition; and wherein the substantially non-odorous fragrance modulator is as described herein.

It has been ascertained that, amongst such compositions of the present invention, the preferred compositions are those comprising of:

(i) a fragrance component present in an amount of from about 0.04 wt % to about 30 wt %, relative to the total weight of the composition, and wherein the fragrance component comprises;
  (a) at least one low volatile fragrance material having a vapor pressure less than 0.001 Torr (0.000133 kPa) at 25° C.; and
  (b) at least one volatile fragrance material having a vapor pressure greater than or equal to 0.001 Torr (0.000133 kPa) at 25° C.; wherein the weight ratio of the low volatile fragrance material versus the volatile fragrance material are present in the range of from 30:70 to 10:90;
(ii) at least one substantially non-odorous fragrance modulator present in the amount of from about 0.1 wt % to about 20 wt %, relative to the weight of the composition;
(iii) a volatile solvent present in an amount of from about 50 wt % to about 80 wt % relative to the total weight of the composition; and
(iv) optionally water.

Preferably, the present invention relates to a fine fragrance composition, preferably in the form of a perfume concentrate, a perfume, a parfum, an eau de toilette, an eau de parfum, or a cologne.

Preferably, the present invention relates to a composition, wherein the composition is in the form of a body splash or a body spray.

Therefore, it goes without saying that the compositions of the present invention encompasses any composition comprising any of the ingredients cited herein, in any embodiment wherein each such ingredient is independently present in any appropriate amount as defined herein. Many such compositions, than what is specifically set out herein, can be encompassed.

Article of Manufacture

The composition may be included in an article of manufacture comprising a spray dispenser. The spray dispenser may comprise a vessel for containing the composition to be dispensed. The spray dispenser may comprise an aerosolized composition (i.e., a composition comprising a propellant) within the vessel as well. Other non-limiting examples of spray dispensers include non-aerosol dispensers (e.g., vapor sprays), manually activated dispensers, pump-spray dispensers, or any other suitable spray dispenser available in the art.

Methods of Using the Compositions

The composition of the present invention according to any embodiments described herein is a useful perfuming composition, which can be advantageously used as consumer products intended to perfume any suitable substrate. As used herein, the term "substrate" means any surface to which the composition of the present invention may be applied to without causing any undue adverse effect. For example, this can include a wide range of surfaces including human or animal skin or hair, paper (fragranced paper), air in a room (air freshener or aromatherapy composition), fabric, furnishings, dishes, hard surfaces and related materials. Preferred substrates include body surfaces such as, for example, hair and skin, most preferably skin.

The composition of the present invention may be used in a conventional manner for fragrancing a substrate. An effective amount of the composition, typically from about 1 µL to about 10,000 µL, preferably from about 10 µL to about 1,000 µL, more preferably from about 25 µL to about 500 µL, or most preferably from about 50 µL to about 100 µL, or combinations thereof, is applied to the suitable substrate. Alternatively, an effective amount of the composition of the present invention is from about 1 µL, 10 µL, 25 µL or 50 µL to about 100 µL, 500 µL, 1,000 µL or 10,000 µL. The composition may be applied by hand or applied utilizing a delivery apparatus such as, for example, vaporizer or atomizer. Preferably, the composition is allowed to dry after its application to the substrate. The scope of the present invention should be considered to cover one or more distinct applications of the composition or the continuous release of a composition via a vaporizer or other type of atomizer.

The present invention provides a method of modifying or enhancing the odour properties of a body surface, preferably hair or skin, comprising contacting or treating the body surface with a composition of the present invention.

The present invention also relates to compositions of the present invention that may be used as consumer products or articles selected from the group consisting of a fabric care product, an air care product, or a home care product. Therefore, according to this embodiment, the present invention provides a method of modifying or enhancing the odour properties of a substrate, preferably fabric, furnishings, dishes, hard surfaces and related materials, comprising contacting or treating the substrate with a composition of the present invention.

In another aspect, the present invention is directed to a method of enhancing the fragrance profile of a composition, preferably by improving the longevity of a character of the composition. The method comprises bringing into contact or mixing at least one substantially non-odorous fragrance modulator with at least one low volatile fragrance material according to the composition of the present invention. Preferably, the character is derived from the volatile fragrance materials in the composition and is characterized by a floral character or aromatic/spicy character. Non-limiting examples of floral character include: lavender-type note, a rose-type note, a lily of the valley-type note, a muguet-type note, a jasmine-type note, a magnolia-type note, a cyclamen-type note, a hyacinth-type note, a lilac-type note, an orange blossom-type note, a cherry blossom-type note, a peony-type note, a lotus-type note, a linden blossom-type note, an osmanthus-type note, a heliotrope-type note, a violet-type note, an orris-type note, a tiare-type, a patchouli-type note and the like.

Non-limiting examples of aromatic (or haerbaceous) and spicy character include: cinnamon, cloves, coriander, ginger, saffron, peppers of various kinds (e.g.: black pepper, pink pepper), caraway, cardamom, anise, tea, coffee, cumin, nutmeg, coumarin, basil, rosemary, thyme, mint, tarragon, marjoram, fennel, sage, and juniper.

Preferably, the fragrance profile or character of the composition of the present invention is detectable by a consumer at later time points such as, for example, 2 hours, 3 hours, 4 hours, 5 hours, 6 hours, 7 hours, 8 hours, 10 hours, and possibly all the way up to 24 hours after application of the composition to a substrate as compared to controls.

In another aspect, the present invention is also directed to a method of producing a consumer product comprising bringing into contact or mixing into the product an organoleptically active quantity of a composition of the present invention. Preferably, the present invention is also directed to a perfuming consumer product or article comprising a composition according to the present invention, wherein the perfuming consumer product is selected from the group consisting of a fabric care product, an air care product or a home care product.

Fragrance Materials

In order that the compositions can be developed with the appropriate fragrance profile for the present invention, the "fragrance materials" have been classified as low volatile fragrance materials or volatile fragrance materials by their vapor pressure. This method of classifying fragrance materials by their vapor pressure avoids the problem of different classifications for the same fragrance material according to the traditional approach that relies on their subjective character. For the purpose of clarity, when the fragrance materials refer to a single individual compound, its vapor pressure should be determined according to the reference program cited above. In the case that the fragrance materials are a natural oil, extract or absolute, which comprises a mixture of several compounds, the vapor pressure of the complete oil should be treated a mixture of the individual perfume raw material components using the reference program cited above. The individual components and their level, in any given natural oil or extract, can be determined by direct injection of the oil into a GC-MS column for analysis as known by one skilled in the art. In the scenario that the fragrance materials are a proprietary specialty accord, so called 'bases', the vapor pressure, using the reference program cited above, should preferably be obtained from the supplier. However, it is understood by one skilled in the art that they can physically analyze the composition of a full fragrance oil available commercially to identity the fragrance raw materials and their levels using standard GC-MS techniques. This would be irrespective of whether they had been added to the fragrance oil as individual chemicals, as components of naturals or from proprietary bases. Although proprietary bases and naturals are included in our examples, when analyzing a commercially available fragrance via GC-MS one could simply identify the components of the base or natural oil as part of the overall fragrance mixture and their levels, without being able to identify which proprietary base or natural oil the fragrance had come from.

The nature and type of fragrance materials in the compositions according to the present invention can be selected by the skilled person, on the basis of its general knowledge together with the teachings contained herein, with reference to the intended use or application of the composition and the desired fragrance profile effect. Examples of suitable fragrance materials are disclosed in U.S. Pat. Nos. 4,145,184, 4,209,417, 4,515,705, and 4,152,272, provided that the composition comprises low volatile fragrance materials at levels in an amount of from about 10 wt % to about 30 wt %, preferably less than about 30 wt %, preferably less than about 28 wt %, or preferably less than 25 wt %, or combinations thereof, relative to the total weight of the fragrance component.

(i) Low Volatile Fragrance Materials

Preferable examples of fragrance materials having a vapor pressure less than 0.001 Torr (0.000133 kPa) at 25° C. (according to the reference program Advanced Chemistry Development (ACD/Labs) Software Version 14.02) to form the at most about 30 wt % of the low volatile fragrance materials are listed in Table 1 hereinafter. Preferably, the low volatile fragrance material is selected from at least 1 material, or at least 2 materials, or at least 3 materials, or at least 5 materials, or at least 7 materials as disclosed in Table 1.

TABLE 1

Low Volatile Fragrance Materials

| No. | CAS Number | IUPAC Name | Common Name** | Vapor Pressure (Torr at 25° C.)* |
|---|---|---|---|---|
| 1. | 1211-29-6 | Cyclopentaneacetic acid, 3-oxo-2-(2Z)-2-penten-1-yl-, methyl ester, (1R,2R)- | Methyl jasmonate | 0.00096500 |
| 2. | 28219-60-5 | 2-Buten-1-ol, 2-methyl-4-(2,2,3-trimethyl-3-cyclopenten-1-yl)- | Hindinol | 0.00096100 |
| 3. | 93-08-3 | Ethanone, 1-(2-naphthalenyl)- | Methyl beta-naphthyl ketone | 0.00095700 |
| 4. | 67633-95-8 | 3-Decanone, 1-hydroxy- | Methyl Lavender Ketone | 0.00095100 |
| 5. | 198404-98-7 | Cyclopropanemethanol, 1-methyl-2-[(1,2,2-trimethylbicyclo[3.1.0]hex-3-yl)methyl]- | Javanol ® | 0.00090200 |
| 6. | 121-32-4 | Benzaldehyde, 3-ethoxy-4-hydroxy- | Ethyl vanillin | 0.00088400 |
| 7. | 72403-67-9 | 3-Cyclohexene-1-methanol, 4-(4-methyl-3-penten-1-yl)-, 1-acetate | Myraldylacetate | 0.00087900 |
| 8. | 28940-11-6 | 2H-1,5-Benzodioxepin-3(4H)-one, 7-methyl- | Calone | 0.00083100 |
| 9. | 139504-68-0 | 2-Butanol, 1-[[2-(1,1-dimethylethyl)cyclohexyl]oxy]- | Amber core | 0.00080300 |
| 10. | 502847-01-0 | Spiro[5.5]undec-8-en-1-one, 2,2,7,9-tetramethyl- | Spiro[5.5]undec-8-en-1-one, 2,2,7,9-tetramethyl- | 0.00073100 |
| 11. | 2570-03-8 | Cyclopentaneacetic acid, 3-oxo-2-pentyl-, methyl ester, (1R,2R)-rel- | trans-Hedione | 0.00071000 |
| 12. | 24851-98-7 (or 128087-96-7) | Cyclopentaneacetic acid, 3-oxo-2-pentyl-, methyl ester | Methyl dihydrojasmonate or alternatives [1] | 0.00071000 |
| 13. | 101-86-0 | Octanal, 2-(phenylmethylene)- | Hexyl cinnamic aldehyde | 0.00069700 |
| 14. | 365411-50-3 | Indeno[4,5-d]-1,3-dioxin, 4,4a,5,6,7,8,9,9b-octahydro-7,7,8,9,9-pentamethyl- | Nebulone | 0.00069200 |
| 15. | 37172-53-5 | Cyclopentanecarboxylic acid, 2-hexyl-3-oxo-, methyl ester | Dihydro Iso Jasmonate | 0.00067500 |

TABLE 1-continued

Low Volatile Fragrance Materials

| No. | CAS Number | IUPAC Name | Common Name** | Vapor Pressure (Torr at 25° C.)* |
|---|---|---|---|---|
| 16. | 65113-99-7 | 3-Cyclopentene-1-butanol, α,β,2,2,3-pentamethyl- | Sandalore ® | 0.00062500 |
| 17. | 68133-79-9 | Cyclopentanone, 2-(3,7-dimethyl-2,6-octadien-1-yl)- | Apritone | 0.00062000 |
| 18. | 7212-44-4 | 1,6,10-Dodecatrien-3-ol, 3,7,11-trimethyl- | Nerolidol | 0.00061600 |
| 19. | 53243-59-7 | 2-Pentenenitrile, 3-methyl-5-phenyl-, (2Z)- | Citronitril | 0.00061500 |
| 20. | 134123-93-6 | Benzenepropanenitrile, 4-ethyl-α,α-dimethyl- | Fleuranil | 0.00057600 |
| 21. | 77-53-2 | 1H-3a,7-Methanoazulen-6-ol, octahydro-3,6,8,8-tetramethyl-, (3R,3aS,6R,7R,8aS)- | Cedrol Crude | 0.00056900 |
| 22. | 68155-66-8 | Ethanone, 1-(1,2,3,5,6,7,8,8a-octahydro-2,3,8,8-tetramethyl-2-naphthalenyl)- | Iso Gamma Super | 0.00056500 |
| 23. | 54464-57-2 | Ethanone, 1-(1,2,3,4,5,6,7,8-octahydro-2,3,8,8-tetramethyl-2-naphthalenyl)- | Iso-E Super ® | 0.00053800 |
| 24. | 774-55-0 | Ethanone, 1-(5,6,7,8-tetrahydro-2-naphthalenyl)- | Florantone | 0.00053000 |
| 25. | 141-92-4 | 2-Octanol, 8,8-dimethoxy-2,6-dimethyl- | Hydroxycitronellal Dimethyl Acetal | 0.00052000 |
| 26. | 20665-85-4 | Propanoic acid, 2-methyl-, 4-formyl-2-methoxyphenyl ester | Vanillin isobutyrate | 0.00051200 |
| 27. | 79-78-7 | 1,6-Heptadien-3-one, 1-(2,6,6-trimethyl-2-cyclohexen-1-yl)- | Hexalon | 0.00049800 |
| 28. | 6259-76-3 | Benzoic acid, 2-hydroxy-, hexyl ester | Hexyl Salicylate | 0.00049100 |
| 29. | 93-99-2 | Benzoic acid, phenyl ester | Phenyl Benzoate | 0.00047900 |
| 30. | 153859-23-5 | Cyclohexanepropanol, 2,2,6-trimethyl-α-propyl-, (1R,6S)- | Norlimbanol | 0.00046900 |
| 31. | 70788-30-6 | Cyclohexanepropanol, 2,2,6-trimethyl-α-propyl- | Timberol | 0.00046900 |
| 32. | 68555-58-8 | Benzoic acid, 2-hydroxy-, 3-methyl-2-buten-1-yl ester | Prenyl Salicylate | 0.00045700 |
| 33. | 950919-28-5 | 2H-1,5-Benzodioxepin-3(4H)-one, 7-(1-methylethyl)- | Cascalone | 0.00045500 |
| 34. | 30168-23-1 | Butanal, 4-(octahydro-4,7-methano-5H-inden-5-ylidene)- | Dupical | 0.00044100 |
| 35. | 1222-05-5 | Cyclopenta[g]-2-benzopyran, 1,3,4,6,7,8-hexahydro-4,6,6,7,8,8-hexamethyl- | Galaxolide ® | 0.00041400 |
| 36. | 4602-84-0 | 2,6,10-Dodecatrien-1-ol, 3,7,11-trimethyl- | Farnesol | 0.00037000 |
| 37. | 95962-14-4 | Cyclopentanone, 2-[2-(4-methyl-3-cyclohexen-1-yl)propyl]- | Nectaryl | 0.00036700 |
| 38. | 4674-50-4 | 2(3H)-Naphthalenone, 4,4a,5,6,7,8-hexahydro-4,4a-dimethyl-6-(1-methylethenyl)-, (4R,4aS,6R)- | Nootkatone | 0.00035800 |
| 39. | 3487-99-8 | 2-Propenoic acid, 3-phenyl-, pentyl ester | Amyl Cinnamate | 0.00035200 |
| 40. | 10522-41-5 | 2-hydroxy-2-phenylethy acetate | hydroxyphenethyl acetate | 0.00033900 |
| 41. | 118-71-8 | 4H-Pyran-4-one, 3-hydroxy-2-methyl- | Maltol | 0.00033700 |
| 42. | 128119-70-0 | 1-Propanol, 2-methyl-3-[(1,7,7-trimethylbicyclo[2.2.1]hept-2-yl)oxy]- | Bornafix | 0.00033400 |
| 43. | 103614-86-4 | 1-Naphthalenol, 1,2,3,4,4a,5,8,8a-octahydro-2,2,6,8-tetramethyl- | Octalynol | 0.00033200 |
| 44. | 7785-33-3 | 2-Butenoic acid, 2-methyl-, (2E)-3,7-dimethyl-2,6-octadien-1-yl ester, (2E)- | Geranyl Tiglate | 0.00033200 |
| 45. | 117933-89-8 | 1,3-Dioxane, 2-(2,4-dimethyl-3-cyclohexen-1-yl)-5-methyl-5-(1-methylpropyl)- | Karanal | 0.00033100 |
| 46. | 629-92-5 | Nonadecane | Nonadecane | 0.00032500 |
| 47. | 67801-20-1 | 4-Penten-2-ol, 3-methyl-5-(2,2,3-trimethyl-3-cyclopenten-1-yl)- | Ebanol | 0.00028100 |
| 48. | 65416-14-0 | Propanoic acid, 2-methyl-, 2-methyl-4-oxo-4H-pyran-3-yl ester | Maltol Isobutyrate | 0.00028000 |

TABLE 1-continued

Low Volatile Fragrance Materials

| No. | CAS Number | IUPAC Name | Common Name** | Vapor Pressure (Torr at 25° C.)* |
|---|---|---|---|---|
| 49. | 28219-61-6 | 2-Buten-1-ol, 2-ethyl-4-(2,2,3-trimethyl-3-cyclopenten-1-yl)- | Laevo Trisandol | 0.00028000 |
| 50. | 5986-55-0 | 1,6-Methanonaphthalen-1(2H)-ol, octahydro-4,8a,9,9-tetramethyl-, (1R,4S,4aS,6R,8aS)- | Healingwood | 0.00027800 |
| 51. | 195251-91-3 | 2H-1,5-Benzodioxepin-3(4H)-one, 7-(1,1-dimethylethyl)- | Transluzone | 0.00026500 |
| 52. | 3100-36-5 | 8-Cyclohexadecen-1-one | Cyclohexadecenone | 0.00025300 |
| 53. | 65405-77-8 | Benzoic acid, 2-hydroxy-, (3Z)-3-hexen-1-yl ester | cis-3-Hexenyl salicylate | 0.00024600 |
| 54. | 4940-11-8 | 4H-Pyran-4-one, 2-ethyl-3-hydroxy- | Ethyl Maltol | 0.00022800 |
| 55. | 541-91-3 | Cyclopentadecanone, 3-methyl- | Muskone | 0.00017600 |
| 56. | 118-58-1 | Benzoic acid, 2-hydroxy-, phenylmethyl ester | Benzyl salicylate | 0.00017500 |
| 57. | 81783-01-9 | 6,8-Nonadien-3-one, 2,4,4,7-tetramethyl-, oxime | Labienoxime | 0.00017300 |
| 58. | 25485-88-5 | Benzoic acid, 2-hydroxy-, cyclohexyl ester | Cyclohexyl Salicylate | 0.00017300 |
| 59. | 91-87-2 | Benzene, [2-(dimethoxymethyl)-1-hepten-1-yl]- | Amyl Cinnamic Aldehyde Dimethyl Acetal | 0.00016300 |
| 60. | 104864-90-6 | 3-Cyclopentene-1-butanol, β,2,2,3-tetramethyl-δ-methylene- | Firsantol | 0.00016000 |
| 61. | 224031-70-3 | 4-Penten-1-one, 1-spiro[4.5]dec-7-en-7-yl- | Spirogalbanone | 0.00015300 |
| 62. | 134-28-1 | 5-Azulenemethanol, 1,2,3,4,5,6,7,8-octahydro-α,α,3,8-tetramethyl-, 5-acetate, (3S,5R,8S)- | Guaiyl Acetate | 0.00013400 |
| 63. | 236391-76-7 | Acetic acid, 2-(1-oxopropoxy)-, 1-(3,3-dimethylcyclohexyl)ethyl ester | Romandolide ® | 0.00012400 |
| 64. | 115-71-9 | 2-Penten-1-ol, 5-[(1R,3R,6S)-2,3-dimethyltricyclo[2.2.1.02,6]hept-3-yl]-2-methyl-, (2Z)- | cis-alpha-Santalol | 0.00011800 |
| 65. | 107898-54-4 | 4-Penten-2-ol, 3,3-dimethyl-5-(2,2,3-trimethyl-3-cyclopenten-1-yl)- | Polysantol ® | 0.00011700 |
| 66. | 69486-14-2 | 5,8-Methano-2H-1-benzopyran-2-one, 6-ethylideneoctahydro- | Florex ® | 0.00011000 |
| 67. | 84697-09-6 | Heptanal, 2-[(4-methylphenyl)methylene]- | Acalea | 0.00010100 |
| 68. | 14595-54-1 | 4-Cyclopentadecen-1-one, (Z)- | Exaltenone | 0.00009640 |
| 69. | 32388-55-9 | Ethanone, 1-[(3R,3aR,7R,8aS)-2,3,4,7,8,8a-hexahydro-3,6,8,8-tetramethyl-1H-3a,7-methanoazulen-5-yl]- | Vertofix ® | 0.00008490 |
| 70. | 131812-67-4 | 1,3-Dioxolane, 2,4-dimethyl-2-(5,6,7,8-tetrahydro-5,5,8,8-tetramethyl-2-naphthalenyl)- | Okoumal ® | 0.00007600 |
| 71. | 106-02-5 | Oxacyclohexadecan-2-one | Exaltolide ® | 0.00006430 |
| 72. | 141773-73-1 | 1-Propanol, 2-[1-(3,3-dimethylcyclohexyl)ethoxy]-2-methyl-, 1-propanoate | Helvetolide ® | 0.00005790 |
| 73. | 63314-79-4 | 5-Cyclopentadecen-1-one, 3-methyl- | Delta Muscenone | 0.00005650 |
| 74. | 77-42-9 | 2-Penten-1-ol, 2-methyl-5-[(1S,2R,4R)-2-methyl-3-methylenebicyclo[2.2.1]hept-2-yl]-, (2Z)- | cis-beta-Santalol | 0.00004810 |
| 75. | 362467-67-2 | 2H-1,5-Benzodioxepin-3(4H)-one, 7-(3-methylbutyl)- | Azurone | 0.00004770 |
| 76. | 28371-99-5 | Ethanone, 1-(2,6,10-trimethyl-2,5,9-cyclododecatrien-1-yl)- | Trimofix O | 0.00004580 |
| 77. | 16223-63-5 | 1H-3a,6-Methanoazulene-3-methanol, octahydro-7,7-dimethyl-8-methylene-, (35,3aR,6R,8aS)- | Khusimol | 0.00004400 |
| 78. | 10461-98-0 | Benzeneacetonitrile, α-cyclohexylidene- | Peonile | 0.00004290 |
| 79. | 50607-64-2 | Benzoic acid, 2-[(2-methylpentylidene)amino]-, methyl ester | Mevantraal | 0.00004070 |

TABLE 1-continued

Low Volatile Fragrance Materials

| No. | CAS Number | IUPAC Name | Common Name** | Vapor Pressure (Torr at 25° C.)* |
|---|---|---|---|---|
| 80. | 29895-73-6 | 5-Hydroxy-2-benzyl-1,3-dioxane | Acetal CD | 0.00004050 |
| 81. | 94-47-3 | Benzoic acid, 2-phenylethyl ester | Phenyl Ethyl Benzoate | 0.00003480 |
| 82. | 3100-36-5 | Cyclohexadec-8-en-1-one | Globanone ® | 0.00003310 |
| 83. | 37609-25-9 | 5-Cyclohexadecen-1-One | Ambretone | 0.00003310 |
| 84. | 66072-32-0 | Cyclohexanol, 4-(1,7,7-trimethylbicyclo[2.2.1]hept-2-yl)- | Iso Bornyl Cyclohexanol | 0.00003010 |
| 85. | 31906-04-4 | 3-Cyclohexene-1-carboxaldehyde, 4-(4-hydroxy-4-methylpentyl)- | Lyral ® | 0.00002940 |
| 86. | 21145-77-7 | Ethanone, 1-(5,6,7,8-tetrahydro-3,5,5,6,8,8-hexamethyl-2-naphthalenyl)- | Musk Plus | 0.00002860 |
| 87. | 21145-77-7 | Ethanone, 1-(5,6,7,8-tetrahydro-3,5,5,6,8,8-hexamethyl-2-naphthalenyl)- | Fixolide | 0.00002860 |
| 88. | 22442-01-9 | 2-Cyclopentadecen-1-one, 3-methyl- | Muscenone | 0.00002770 |
| 89. | 109-29-5 | Oxacycloheptadecan-2-one | Silvanone Ci | 0.00002600 |
| 90. | 101-94-0 | Benzeneacetic acid, 4-methylphenyl ester | Para Cresyl Phenyl Acetate | 0.00002330 |
| 91. | 102-20-5 | Benzeneacetic acid, 2-phenylethyl ester | Phenyl Ethyl Phenyl Acetate | 0.00002300 |
| 92. | 118562-73-5 | Cyclododecaneethanol, β-methyl- | Hydroxyambran | 0.00001800 |
| 93. | 103-41-3 | 2-Propenoic acid, 3-phenyl-, phenylmethyl ester | Benzyl Cinnamate | 0.00001050 |
| 94. | 4707-47-5 | Benzoic acid, 2,4-dihydroxy-3,6-dimethyl-, methyl ester | Veramoss | 0.00001050 |
| 95. | 183551-83-9 | Naphtho[2,1-b]furan-6(7H)-one, 8,9-dihydro-1,5,8-trimethyl-, (8R)- | Myrrhone | 0.00000977 |
| 96. | 102-17-0 | Benzeneacetic acid, (4-methoxyphenyl)methyl ester | Para Anisyl Phenyl Acetate | 0.00000813 |
| 97. | 120-11-6 | Benzene, 2-methoxy-1-(phenylmethoxy)-4-(1-propen-1-yl)- | Benzyl Iso Eugenol | 0.00000676 |
| 98. | 102-22-7 | Benzeneacetic acid, (2E)-3,7-dimethyl-2,6-octadien-1-yl ester | Geranyl Phenylacetate | 0.00000645 |
| 99. | 111879-80-2 | Oxacyclohexadec-12-en-2-one, (12E)- | Habanolide 100% | 0.00000431 |
| 100. | 87-22-9 | Benzoic acid, 2-hydroxy-, 2-phenylethyl ester | Phenyl Ethyl Salicylate | 0.00000299 |
| 101. | 78-37-5 | 2-Propenoic acid, 3-phenyl-, 1-ethenyl-1,5-dimethyl-4-hexen-1-yl ester | Linalyl Cinnamate | 0.00000174 |
| 102. | 28645-51-4 | Oxacycloheptadec-10-en-2-one | Ambrettolide | 0.00000139 |
| 103. | 123-69-3 | Oxacycloheptadec-8-en-2-one, (8Z)- | Ambrettolide | 0.00000136 |
| 104. | 3391-83-1 | 1,7-Dioxacycloheptadecan-8-one | Musk RI | 0.00000057 |
| 105. | 68527-79-7 | 7-Octen-2-ol, 8-(1H-indol-1-yl)-2,6-dimethyl- | Indolene | 0.000000445 |
| 106. | 89-43-0 | Methyl 2-[(7-hydroxy-3,7-dimethyloctylidene)amino]benzoate | Aurantinol | 0.0000000100 |
| 107. | 54982-83-1 | 1,4-Dioxocyclohexadecane-5,16-dione | Zenolide | 0.00000000834 |
| 108. | 105-95-3 | 1,4-Dioxacycloheptadecane-5,17-dione | Ethylene Brassylate | 0.00000000313 |
| 109. | 3681-73-0 | Hexadecanoic acid, (2E)-3,7-dimethyl-2,6-octadien-1-yl ester | Hexarose | 0.00000000300 |
| 110. | 4159-29-9 | Phenol, 4-[3-(benzoyloxy)-1-propen-1-yl]-2-methoxy- | Coniferyl benzoate | 0.00000000170 |
| 111. | 144761-91-1 | Benzoic acid, 2-[(1-hydroxy-3-phenylbutyl)amino]-, methyl ester | Trifone DIPG | 0.00000000093 |

[1] Non-limiting examples of alternative qualities from various suppliers can be purchased under the following tradenames: Kharismal ® Super (IFF), Kharismal ® (IFF), Hedione ® (Firmenich), HedioneHC ® (Firmenich), Paradisone (Firmenich), Cepionate (Zenon), Super cepionate (Zenon), Claigeon ® (Zenon).
*Vapor Pressures are acquired as described in the Test Methods Section.
**Origin: The low volatile fragrance materials may be obtained from one or more of the following companies: Firmenich (Geneva, Switzerland), Symrise AG (Holzminden, Germany), Givaudan (Argenteuil, France), IFF (Hazlet, New Jersey), Bedoukian (Danbury, Connecticut), Sigma Aldrich (St. Louis, Missouri), Millennium Speciality Chemicals (Olympia Fields, Illinois), Polarone International (Jersey City, New Jersey), and Aroma & Flavor Specialities (Danbury, Connecticut).

Preferably, the compositions of the present invention, wherein the low volatile fragrance material is selected from the group consisting of Table 1 Perfume Raw Materials 1, 4-6, 8, 12-16, 18, 22-28, 31, 34-37, 41, 45, 47, 52-55, 57, 60, 61, 63, 65, 68, 69-73, 75, 78, 80, 83-84, 89, 94, 99, 102, 104, 106-108, and mixtures thereof. Preferably, the compositions of the present invention, the low volatile fragrance material is selected from the group (as described herein above), and wherein this group of low volatile fragrance material has at least about 20 wt %, at least about 30 wt %, at least about 40 wt %, at least about 50 wt %, at least about 60 wt %, or at least about 70 wt %, relative to the total weight of the low volatile fragrance material.

Preferably, the compositions of the present invention are those wherein the low volatile fragrance materials comprise at most about 30 wt %, or preferably at most about 28 wt %, or preferably at most about 25 wt %, or alternatively combinations thereof, relative to the total weight of the fragrance component. Exemplary low volatile fragrance materials selected from the group consisting of Table 1 Low Volatile Fragrance Materials are preferred. However, it is understood by one skilled in the art that other low volatile fragrance materials, not recited in Table 1, would also fall within the scope of the present invention, so long as they have a vapor pressure less than 0.001 Torr (0.000133 kPa) at 25° C.

(ii) Volatile Fragrance Materials

Preferable examples of fragrance materials having a vapor pressure greater than or equal to 0.001 Torr (0.000133 kPa) at 25° C. (according to the reference program Advanced Chemistry Development (ACD/Labs) Software Version 14.02) are provided in Table 2 hereinafter. Preferably, the volatile fragrance material is selected from at least 1 material, or at least 2 materials, or at least 3 materials, or at least 5 materials, or at least 7 materials as disclosed in Table 2.

TABLE 2

Volatile Fragrance Materials

| No. | CAS Number | IUPAC Name | Common Name** | Vapor Pressure (Torr at 25° C.)* |
|---|---|---|---|---|
| 1. | 107-31-3 | Formic acid, methyl ester | Methyl Formate | 732.00000000 |
| 2. | 75-18-3 | Methane, 1,1'-thiobis- | Dimethyl Sulfide 1.0% In DEP | 647.00000000 |
| 3. | 141-78-6 | Acetic acid ethyl ester | Ethyl Acetate | 112.00000000 |
| 4. | 105-37-3 | Propanoic acid, ethyl ester | Ethyl Propionate | 44.50000000 |
| 5. | 110-19-0 | Acetic acid, 2-methylpropyl ester | Isobutyl Acetate | 18.00000000 |
| 6. | 105-54-4 | Butanoic acid, ethyl ester | Ethyl Butyrate | 13.90000000 |
| 7. | 14765-30-1 | 1-Butanol | Butyl Alcohol | 8.52000000 |
| 8. | 7452-79-1 | Butanoic acid, 2-methyl-, ethyl ester | Ethyl-2-Methyl Butyrate | 7.85000000 |
| 9. | 123-92-2 | 1-Butanol, 3-methyl-, 1-acetate | Iso Amyl Acetate | 5.68000000 |
| 10. | 66576-71-4 | Butanoic acid, 2-methyl-, 1-methylethyl ester | Iso Propyl 2-Methylbutyrate | 5.10000000 |
| 11. | 110-43-0 | 2-Heptanone | Methyl Amyl Ketone | 4.73000000 |
| 12. | 6728-26-3 | 2-Hexenal, (2E) | Trans-2 Hexenal | 4.62000000 |
| 13. | 123-51-3 | 1-Butanol, 3-methyl- | Isoamyl Alcohol | 4.16000000 |
| 14. | 1191-16-8 | 2-Buten-1-ol, 3-methyl-, 1-acetate | Prenyl acetate | 3.99000000 |
| 15. | 57366-77-5 | 1,3-Dioxolane-2-methanamine, N-methyl- | Methyl Dioxolan | 3.88000000 |
| 16. | 7785-70-8 | Bicyclo[3.1.1]hept-2-ene, 2,6,6-trimethyl-, (1R,5R)- | Alpha Pinene | 3.49000000 |
| 17. | 79-92-5 | Bicyclo[2.2.1]heptane, 2,2-dimethyl-3-methylene- | Camphene | 3.38000000 |
| 18. | 94087-83-9 | 2-Butanethiol, 4-methoxy-2-methyl- | 4-Methoxy-2-Methyl-2-Butanenthiol | 3.31000000 |
| 19. | 39255-32-8 | Pentanoic acid, 2-methyl-, ethyl ester | Manzanate | 2.91000000 |
| 20. | 3387-41-5 | Bicyclo[3.1.0]hexane, 4-methylene-1-(1-methylethyl)- | Sabinene | 2.63000000 |
| 21. | 127-91-3 | Bicyclo[3.1.1]heptane, 6,6-dimethyl-2-methylene- | Beta Pinene | 2.40000000 |
| 22. | 105-68-0 | 1-Butanol, 3-methyl-, 1-propanoate | Amyl Propionate | 2.36000000 |
| 23. | 123-35-3 | 1,6-Octadiene, 7-methyl-3-methylene- | Myrcene | 2.29000000 |
| 24. | 124-13-0 | Octanal | Octyl Aldehyde | 2.07000000 |
| 25. | 7392-19-0 | 2H-Pyran, 2-ethenyltetrahydro-2,6,6-trimethyl- | Limetol | 1.90000000 |
| 26. | 111-13-7 | 2-Octanone | Methyl Hexyl Ketone | 1.72000000 |
| 27. | 123-66-0 | Hexanoic acid, ethyl ester | Ethyl Caproate | 1.66000000 |
| 28. | 470-82-6 | 2-Oxabicyclo[2.2.2]octane, 1,3,3-trimethyl- | Eucalyptol | 1.65000000 |
| 29. | 99-87-6 | Benzene, 1-methyl-4-(1-methylethyl)- | Para Cymene | 1.65000000 |
| 30. | 104-93-8 | Benzene, 1-methoxy-4-methyl- | Para Cresyl Methyl Ether | 1.65000000 |
| 31. | 13877-91-3 | 1,3,6-Octatriene, 3,7-dimethyl- | Ocimene | 1.56000000 |
| 32. | 138-86-3 | Cyclohexene, 1-methyl-4-(1-methylethenyl)- | dl-Limonene | 1.54000000 |

TABLE 2-continued

Volatile Fragrance Materials

| No. | CAS Number | IUPAC Name | Common Name** | Vapor Pressure (Torr at 25° C.)* |
|---|---|---|---|---|
| 33. | 5989-27-5 | Cyclohexene, 1-methyl-4-(1-methylethenyl)-, (4R)- | d-limonene | 1.54000000 |
| 34. | 106-68-3 | 3-Octanone | Ethyl Amyl Ketone | 1.50000000 |
| 35. | 110-41-8 | Undecanal, 2-methyl- | Methyl Nonyl Acetaldehyde | 1.43000000 |
| 36. | 142-92-7 | Acetic acid, hexyl ester | Hexyl acetate | 1.39000000 |
| 37. | 110-93-0 | 5-Hepten-2-one, 6-methyl- | Methyl Heptenone | 1.28000000 |
| 38. | 81925-81-7 | 2-Hepten-4-one, 5-methyl- | Filbertone 1% in TEC | 1.25000000 |
| 39. | 3681-71-8 | 3-Hexen-1-ol, 1-acetate, (3Z)- | cis-3-Hexenyl acetate | 1.22000000 |
| 40. | 97-64-3 | Propanoic acid, 2-hydroxy-, ethyl ester | Ethyl Lactate | 1.16000000 |
| 41. | 586-62-9 | Cyclohexene, 1-methyl-4-(1-methylethylidene)- | Terpineolene | 1.13000000 |
| 42. | 51115-64-1 | Butanoic acid, 2-methylbutyl ester | Amyl butyrate | 1.09000000 |
| 43. | 106-27-4 | Butanoic acid, 3-methylbutyl ester | Amyl Butyrate | 1.09000000 |
| 44. | 99-85-4 | 1,4-Cyclohexadiene, 1-methyl-4-(1-methylethyl)- | Gamma Terpinene | 1.08000000 |
| 45. | 18640-74-9 | Thiazole, 2-(2-methylpropyl)- | 2-Isobutylthiazole | 1.07000000 |
| 46. | 928-96-1 | 3-Hexen-1-ol, (3Z)- | cis-3-Hexenol | 1.04000000 |
| 47. | 100-52-7 | Benzaldehyde | Benzaldehyde | 0.97400000 |
| 48. | 141-97-9 | Butanoic acid, 3-oxo-, ethyl ester | Ethyl Acetoacetate | 0.89000000 |
| 49. | 928-95-0 | 2-Hexen-1-ol, (2E)- | Trans-2-Hexenol | 0.87300000 |
| 50. | 928-94-9 | 2-Hexen-1-ol, (2Z)- | Beta Gamma Hexenol | 0.87300000 |
| 51. | 24691-15-4 | Cyclohexane, 3-ethoxy-1,1,5-trimethyl-, cis- (9CI) | Herbavert | 0.85200000 |
| 52. | 19872-52-7 | 2-Pentanone, 4-mercapto-4-methyl- | 4-Methyl-4-Mercaptopentan-2-one 1 ppm TEC | 0.84300000 |
| 53. | 3016-19-1 | 2,4,6-Octatriene, 2,6-dimethyl-, (4E,6E)- | Allo-Ocimene | 0.81600000 |
| 54. | 69103-20-4 | Oxirane, 2,2-dimethyl-3-(3-methyl-2,4-pentadien-1-yl)- | Myroxide | 0.80600000 |
| 55. | 189440-77-5 | 4,7-Octadienoic acid, methyl ester, (4E)- | Anapear | 0.77700000 |
| 56. | 67633-96-9 | Carbonic acid, (3Z)-3-hexen-1-yl methyl ester | Liffarome ™ | 0.72100000 |
| 57. | 123-68-2 | Hexanoic acid, 2-propen-1-yl ester | Allyl Caproate | 0.67800000 |
| 58. | 106-72-9 | 5-Heptenal, 2,6-dimethyl- | Melonal | 0.62200000 |
| 59. | 106-30-9 | Heptanoic acid, ethyl ester | Ethyl Oenanthate | 0.60200000 |
| 60. | 68039-49-6 | 3-Cyclohexene-1-carboxaldehyde, 2,4-dimethyl- | Ligustral or Triplal | 0.57800000 |
| 61. | 101-48-4 | Benzene, (2,2-dimethoxyethyl)- | Phenyl Acetaldehyde Dimethyl Acetal | 0.55600000 |
| 62. | 16409-43-1 | 2H-Pyran, tetrahydro-4-methyl-2-(2-methyl-1-propen-1-yl)- | Rose Oxide | 0.55100000 |
| 63. | 925-78-0 | 3-Nonanone | Ethyl Hexyl Ketone | 0.55100000 |
| 64. | 100-47-0 | Benzonitrile | Benzyl Nitrile | 0.52400000 |
| 65. | 589-98-0 | 3-Octanol | Octanol-3 | 0.51200000 |
| 66. | 58430-94-7 | 1-Hexanol, 3,5,5-trimethyl-, 1-acetate | Iso Nonyl Acetate | 0.47000000 |
| 67. | 10250-45-0 | 4-Heptanol, 2,6-dimethyl-, 4-acetate | Alicate | 0.45400000 |
| 68. | 105-79-3 | Hexanoic acid, 2-methylpropyl ester | Iso Butyl Caproate | 0.41300000 |
| 69. | 2349-07-7 | Propanoic acid, 2-methyl-, hexyl ester | Hexyl isobutyrate | 0.41300000 |
| 70. | 23250-42-2 | Cyclohexanecarboxylic acid, 1,4-dimethyl-, methyl ester, trans- | Cyprissate | 0.40500000 |
| 71. | 122-78-1 | Benzeneacetaldehyde | Phenyl acetaldehyde | 0.36800000 |
| 72. | 5405-41-4 | Butanoic acid, 3-hydroxy-, ethyl ester | Ethyl-3-Hydroxy Butyrate | 0.36200000 |
| 73. | 105-53-3 | Propanedioic acid, 1,3-diethyl ester | Diethyl Malonate | 0.34400000 |

TABLE 2-continued

Volatile Fragrance Materials

| No. | CAS Number | IUPAC Name | Common Name** | Vapor Pressure (Torr at 25° C.)* |
|---|---|---|---|---|
| 74. | 93-58-3 | Benzoic acid, methyl ester | Methyl Benzoate | 0.34000000 |
| 75. | 16356-11-9 | 1,3,5-Undecatriene | Undecatriene | 0.33600000 |
| 76. | 65405-70-1 | 4-Decenal, (4E) | Decenal (Trans-4) | 0.33100000 |
| 77. | 54546-26-8 | 1,3-Dioxane, 2-butyl-4,4,6-trimethyl- | Herboxane | 0.33000000 |
| 78. | 13254-34-7 | 2-Heptanol, 2,6-dimethyl- | Dimethyl-2 6-Heptan-2-ol | 0.33000000 |
| 79. | 98-86-2 | Ethanone, 1-phenyl- | Acetophenone | 0.29900000 |
| 80. | 93-53-8 | Benzeneacetaldehyde, α-methyl- | Hydratropic aldehyde | 0.29400000 |
| 81. | 80118-06-5 | Propanoic acid, 2-methyl-, 1,3-dimethyl-3-buten-1-yl ester | Iso Pentyrate | 0.28500000 |
| 82. | 557-48-2 | 2,6-Nonadienal, (2E,6Z)- | E Z-2,6-Nonadien-1-al | 0.28000000 |
| 83. | 24683-00-9 | Pyrazine, 2-methoxy-3-(2-methylpropyl)- | 2-Methoxy-3-Isobutyl Pyrazine | 0.27300000 |
| 84. | 104-57-4 | Formic acid, phenylmethyl ester | Benzyl Formate | 0.27300000 |
| 85. | 104-45-0 | Benzene, 1-methoxy-4-propyl- | Dihydroanethole | 0.26600000 |
| 86. | 491-07-6 | Cyclohexanone, 5-methyl-2-(1-methylethyl)-, (2R,5R)-rel- | Iso Menthone | 0.25600000 |
| 87. | 89-80-5 | Cyclohexanone, 5-methyl-2-(1-methylethyl)-, (2R,5S)-rel- | Menthone Racemic | 0.25600000 |
| 88. | 2463-53-8 | 2-Nonenal | 2 Nonen-1-al | 0.25600000 |
| 89. | 55739-89-4 | Cyclohexanone, 2-ethyl-4,4-dimethyl- | Thuyacetone | 0.25000000 |
| 90. | 150-78-7 | Benzene, 1,4-dimethoxy- | Hydroquinone Dimethyl Ether | 0.25000000 |
| 91. | 64988-06-3 | Benzene, 1-(ethoxymethyl)-2-methoxy- | Rosacene | 0.24600000 |
| 92. | 76-22-2 | Bicyclo[2.2.1]heptan-2-one, 1,7,7-trimethyl- | Camphor gum | 0.22500000 |
| 93. | 67674-46-8 | 2-Hexene, 6,6-dimethoxy-2,5,5-trimethyl- | Methyl Pamplemousse | 0.21400000 |
| 94. | 112-31-2 | Decanal | Decyl Aldehyde | 0.20700000 |
| 95. | 16251-77-7 | Benzenepropanal, β-methyl- | Trifernal | 0.20600000 |
| 96. | 93-92-5 | Benzenemethanol, α-methyl-, 1-acetate | Methylphenylcarbinol Acetate | 0.20300000 |
| 97. | 143-13-5 | Acetic acid, nonyl ester | Nonyl Acetate | 0.19700000 |
| 98. | 122-00-9 | Ethanone, 1-(4-methylphenyl)- | Para Methyl Acetophenone | 0.18700000 |
| 99. | 24237-00-1 | 2H-Pyran, 6-butyl-3,6-dihydro-2,4-dimethyl- | Gyrane | 0.18600000 |
| 100. | 41519-23-7 | Propanoic acid, 2-methyl-, (3Z)-3-hexen-1-yl ester | Hexenyl Isobutyrate | 0.18200000 |
| 101. | 93-89-0 | Benzoic acid, ethyl ester | Ethyl Benzoate | 0.18000000 |
| 102. | 20780-48-7 | 3-Octanol, 3,7-dimethyl-, 3-acetate | Tetrahydro Linalyl Acetate | 0.18000000 |
| 103. | 101-41-7 | Methyl 2-phenylacetate | Methylphenyl acetate | 0.17600000 |
| 104. | 40853-55-2 | 1-Hexanol, 5-methyl-2-(1-methylethyl)-, 1-acetate | Tetrahydro Lavandulyl Acetate | 0.17300000 |
| 105. | 933-48-2 | Cyclohexanol, 3,3,5-trimethyl-, (1R,5R)-rel- | Trimethylcyclohexanol | 0.17300000 |
| 106. | 35158-25-9 | 2-Hexenal, 5-methyl-2-(1-methylethyl)- | Lactone of Cis Jasmone | 0.17200000 |
| 107. | 18479-58-8 | 7-Octen-2-ol, 2,6-dimethyl- | Dihydromyrcenol | 0.16600000 |
| 108. | 140-11-4 | Acetic acid, phenylmethyl ester | Benzyl acetate | 0.16400000 |
| 109. | 14765-30-1 | Cyclohexanone, 2-(1-methylpropyl)- | 2-sec-Butyl Cyclo Hexanone | 0.16300000 |
| 110. | 20125-84-2 | 3-Octen-1-ol, (3Z)- | Octenol | 0.16000000 |
| 111. | 142-19-8 | Heptanoic acid, 2-propen-1-yl ester | Allyl Heptoate | 0.16000000 |
| 112. | 100-51-6 | Benzenemethanol | Benzyl Alcohol | 0.15800000 |
| 113. | 10032-15-2 | Butanoic acid, 2-methyl-, hexyl ester | Hexyl-2-Methyl Butyrate | 0.15800000 |
| 114. | 695-06-7 | 2(3H)-Furanone, 5-ethyldihydro- | Gamma Hexalactone | 0.15200000 |

TABLE 2-continued

Volatile Fragrance Materials

| No. | CAS Number | IUPAC Name | Common Name** | Vapor Pressure (Torr at 25° C.)* |
|---|---|---|---|---|
| 115. | 21722-83-8 | Cyclohexaneethanol, 1-acetate | Cyclohexyl Ethyl Acetate | 0.15200000 |
| 116. | 111-79-5 | 2-Nonenoic acid, methyl ester | Methyl-2-Nonenoate | 0.14600000 |
| 117. | 16491-36-4 | Butanoic acid, (3Z)-3-hexen-1-yl ester | Cis 3 Hexenyl Butyrate | 0.13500000 |
| 118. | 111-12-6 | 2-Octynoic acid, methyl ester | Methyl Heptine Carbonate | 0.12500000 |
| 119. | 59323-76-1 | 1,3-Oxathiane, 2-methyl-4-propyl-, (2R,4S)-rel- | Oxane | 0.12300000 |
| 120. | 62439-41-2 | Heptanal, 6-methoxy-2,6-dimethyl- | Methoxy Melonal | 0.11900000 |
| 121. | 13851-11-1 | Bicyclo[2.2.1]heptan-2-ol, 1,3,3-trimethyl-, 2-acetate | Fenchyl Acetate | 0.11700000 |
| 122. | 115-95-7 | 1,6-Octadien-3-ol, 3,7-dimethyl-, 3-acetate | Linalyl acetate | 0.11600000 |
| 123. | 18479-57-7 | 2-Octanol, 2,6-dimethyl- | Tetra-Hydro Myrcenol | 0.11500000 |
| 124. | 78-69-3 | 3,7-dimethyloctan-3-ol | Tetra-Hydro Linalool | 0.11500000 |
| 125. | 111-87-5 | 1-Octanol | Octyl Alcohol | 0.11400000 |
| 126. | 71159-90-5 | 3-Cyclohexene-1-methanethiol, α,α,4-trimethyl- | Grapefruit mercaptan | 0.10500000 |
| 127. | 80-25-1 | Cyclohexanemethanol, α,α,4-trimethyl-, 1-acetate | Menthanyl Acetate | 0.10300000 |
| 128. | 88-41-5 | Cyclohexanol, 2-(1,1-dimethylethyl)-, 1-acetate | Verdox ™ | 0.10300000 |
| 129. | 32210-23-4 | Cyclohexanol, 4-(1,1-dimethylethyl)-, 1-acetate | Vertenex | 0.10300000 |
| 130. | 112-44-7 | Undecanal | n-Undecanal | 0.10200000 |
| 131. | 24168-70-5 | Pyrazine, 2-methoxy-3-(1-methylpropyl)- | Methoxyisobutylpyrazine | 0.09950000 |
| 132. | 89-79-2 | Cyclohexanol, 5-methyl-2-(1-methylethenyl)-, (1R,2S,5R)- | Iso-Pulegol | 0.09930000 |
| 133. | 112-12-9 | 2-Undecanone | Methyl Nonyl Ketone | 0.09780000 |
| 134. | 103-05-9 | Benzenepropanol, α,α-dimethyl- | Phenyl Ethyl Dimethyl Carbinol | 0.09770000 |
| 135. | 125-12-2 | Bicyclo[2.2.1]heptan-2-ol, 1,7,7-trimethyl-, 2-acetate, (1R,2R,4R)-rel- | Iso Bornyl Acetate | 0.09590000 |
| 136. | 78-70-6 | 1,6-Octadien-3-ol, 3,7-dimethyl- | Linalool | 0.09050000 |
| 137. | 101-97-3 | Benzeneacetic acid, ethyl ester | Ethyl Phenyl Acetate | 0.08970000 |
| 138. | 100-86-7 | Benzeneethanol, α,α-dimethyl- | Dimethyl Benzyl Carbinol | 0.08880000 |
| 139. | 188570-78-7 | Cyclopropanecarboxylic acid, (3Z)-3-hexen-1-yl ester | Montaverdi | 0.08640000 |
| 140. | 67634-25-7 | 3-Cyclohexene-1-methanol, 3,5-dimethyl-, 1-acetate | Floralate | 0.08500000 |
| 141. | 112-44-7 | Undecanal | Undecyl Aldehyde | 0.08320000 |
| 142. | 32669-00-4 | Ethanone, 1-(3-cycloocten-1-yl)- | Tanaisone ® | 0.08150000 |
| 143. | 98-53-3 | Cyclohexanone, 4-(1,1-dimethylethyl)- | Patchi | 0.07780000 |
| 144. | 35854-86-5 | 6-Nonen-1-ol, (6Z)- | cis-6-None-1-ol | 0.07770000 |
| 145. | 5331-14-6 | Benzene, (2-butoxyethyl)- | Butyl phenethyl ether | 0.07760000 |
| 146. | 80-57-9 | Bicyclo[3.1.1]hept-3-en-2-one, 4,6,6-trimethyl- | Verbenone | 0.07730000 |
| 147. | 22471-55-2 | Cyclohexanecarboxylic acid, 2,2,6-trimethyl-, ethyl ester, (1R,6S)-rel- | Thesaron | 0.07670000 |
| 148. | 60-12-8 | 2-phenyl ethanol | Phenethyl alcohol or Phenylethyl alcohol | 0.07410000 |
| 149. | 106-26-3 | 2,6-Octadienal, 3,7-dimethyl-, (2Z)- | Neral | 0.07120000 |
| 150. | 5392-40-5 | 2,6-Octadienal, 3,7-dimethyl- | Citral | 0.07120000 |
| 151. | 89-48-5 | Cyclohexanol, 5-methyl-2-(1-methylethyl)-, 1-acetate, (1R,2S,5R)-rel- | Menthyl Acetate | 0.07070000 |

TABLE 2-continued

Volatile Fragrance Materials

| No. | CAS Number | IUPAC Name | Common Name** | Vapor Pressure (Torr at 25° C.)* |
|---|---|---|---|---|
| 152. | 119-36-8 | Benzoic acid, 2-hydroxy-, methyl ester | Methyl salicylate | 0.07000000 |
| 153. | 4180-23-8 | Benzene, 1-methoxy-4-(1E)-1-propen-1-yl- | Anethol | 0.06870000 |
| 154. | 7549-37-3 | 2,6-Octadiene, 1,1-dimethoxy-3,7-dimethyl- | Citral Dimethyl Acetal | 0.06780000 |
| 155. | 25225-08-5 | Cyclohexanemethanol, α,3,3-trimethyl-, 1-formate | Aphermate | 0.06780000 |
| 156. | 3913-81-3 | 2-Decenal, (2E)- | 2-Decene-1-al | 0.06740000 |
| 157. | 15373-31-6 | 3-Cyclopentene-1-acetonitrile, 2,2,3-trimethyl- | Cantryl ® | 0.06700000 |
| 158. | 6485-40-1 | 2-Cyclohexen-1-one, 2-methyl-5-(1-methylethenyl)-, (5R)- | Laevo carvone | 0.06560000 |
| 159. | 16587-71-6 | Cyclohexanone, 4-(1,1-dimethylpropyl)- | Orivone | 0.06490000 |
| 160. | 62406-73-9 | 6,10-Dioxaspiro[4.5]decane, 8,8-dimethyl-7-(1-methylethyl)- | Opalal CI | 0.06290000 |
| 161. | 3720-16-9 | 2-Cyclohexen-1-one, 3-methyl-5-propyl- | Livescone | 0.06270000 |
| 162. | 13816-33-6 | Benzonitrile, 4-(1-methylethyl)- | Cumin Nitrile | 0.06230000 |
| 163. | 67019-89-0 | 2,6-Nonadienenitrile | Violet Nitrile | 0.06200000 |
| 164. | 53398-85-9 | Butanoic acid, 2-methyl-, (3Z)-3-hexen-1-yl ester | cis-3-Hexenyl Alpha Methyl Butyrate | 0.06130000 |
| 165. | 208041-98-9 | Heptanenitrile, 2-propyl- | Jasmonitrile | 0.05920000 |
| 166. | 16510-27-3 | Benzene, 1-(cyclopropylmethyl)-4-methoxy- | Toscanol | 0.05870000 |
| 167. | 111-80-8 | 2-Nonynoic acid, methyl ester | Methyl Octine Carbonate | 0.05680000 |
| 168. | 103-45-7 | Acetic acid, 2-phenylethyl ester | Phenyl Ethyl Acetate | 0.05640000 |
| 169. | 2550-26-7 | 2-Butanone, 4-phenyl- | Benzyl Acetone | 0.05570000 |
| 170. | 13491-79-7 | Cyclohexanol, 2-(1,1-dimethylethyl)- | Verdol | 0.05430000 |
| 171. | 7786-44-9 | 2,6-Nonadien-1-ol | 2,6-Nonadien-1-ol | 0.05370000 |
| 172. | 103-28-6 | Propanoic acid, 2-methyl-, phenylmethyl ester | Benzyl Iso Butyrate | 0.05130000 |
| 173. | 104-62-1 | Formic acid, 2-phenylethyl ester | Phenyl Ethyl Formate | 0.05050000 |
| 174. | 28462-85-3 | Bicyclo[2.2.1]heptan-2-ol, 1,2,3,3-tetramethyl-, (1R,2R,4S)-rel- | Humus Ether | 0.04870000 |
| 175. | 122-03-2 | Benzaldehyde, 4-(1-methylethyl)- | Cuminic Aldehyde | 0.04820000 |
| 176. | 358331-95-0 | 2,5-Octadien-4-one, 5,6,7-trimethyl-, (2E)- | Pomarose | 0.04810000 |
| 177. | 562-74-3 | 3-Cyclohexen-1-ol, 4-methyl-1-(1-methylethyl)- | Terpinenol-4 | 0.04780000 |
| 178. | 68527-77-5 | 3-Cyclohexene-1-methanol, 2,4,6-trimethyl- | Isocyclogeraniol | 0.04640000 |
| 179. | 35852-46-1 | Pentanoic acid, (3Z)-3-hexen-1-yl ester | Cis-3-Hexenyl Valerate | 0.04580000 |
| 180. | 2756-56-1 | Bicyclo[2.2.1]heptan-2-ol, 1,7,7-trimethyl-, 2-propanoate, (1R,2R,4R)-rel- | Iso Bornyl Propionate | 0.04540000 |
| 181. | 14374-92-6 | Benzene, 1-methyl-4-(1-methylethyl)-2-(1-propen-1-yl)- | Verdoracine | 0.04460000 |
| 182. | 6784-13-0 | 3-Cyclohexene-1-propanal, β,4-dimethyl- | Limonenal | 0.04380000 |
| 183. | 8000-41-7 | 2-(4-methyl-1-cyclohex-3-enyl)propan-2-ol | Alpha Terpineol | 0.04320000 |
| 184. | 41884-28-0 | 1-Hexanol, 5-methyl-2-(1-methylethyl)-, (2R)- | Tetrahydro Lavandulol | 0.04230000 |
| 185. | 22457-23-4 | 3-Heptanone, 5-methyl-, oxime | Stemone ® | 0.04140000 |

TABLE 2-continued

Volatile Fragrance Materials

| No. | CAS Number | IUPAC Name | Common Name** | Vapor Pressure (Torr at 25° C.)* |
|---|---|---|---|---|
| 186. | 104-50-7 | 2(3H)-Furanone, 5-butyldihydro- | Gamma Octalactone | 0.04080000 |
| 187. | 143-08-8 | 1-Nonanol | Nonyl Alcohol | 0.04070000 |
| 188. | 3613-30-7 | Octanal, 7-methoxy-3,7-dimethyl- | Methoxycitronellal | 0.04020000 |
| 189. | 67634-00-8 | Acetic acid, 2-(3-methylbutoxy)-, 2-propen-1-yl ester | Allyl Amyl Glycolate | 0.04000000 |
| 190. | 464-45-9 | Bicyclo[2.2.1]heptan-2-ol, 1,7,7-trimethyl-, (1S,2R,4S)- | l-Borneol | 0.03980000 |
| 191. | 124-76-5 | Bicyclo[2.2.1]heptan-2-ol, 1,7,7-trimethyl-, (1R,2R,4R)-rel- | 1.7.7-Trimethyl-Bicyclo-1.2.2-Heptanol-2 | 0.03980000 |
| 192. | 67874-72-0 | Cyclohexanol, 2-(1,1 dimethylpropyl)-, 1-acetate | Coniferan | 0.03980000 |
| 193. | 80-26-2 | 3-Cyclohexene-1-methanol, α,α,4-trimethyl-, 1-acetate | Terpinyl Acetate | 0.03920000 |
| 194. | 498-81-7 | Cyclohexanemethanol, α,α,4-trimethyl- | Dihydro Terpineol | 0.03920000 |
| 195. | 112-45-8 | 10-Undecenal | Undecylenic aldehyde | 0.03900000 |
| 196. | 35044-57-6 | 2,4-Cyclohexadiene-1-carboxylic acid, 2,6,6-trimethyl-, ethyl ester | Ethyl Safranate | 0.03880000 |
| 197. | 106-21-8 | 1-Octanol, 3,7-dimethyl- | Dimethyl Octanol | 0.03860000 |
| 198. | 84560-00-9 | Cyclopentanol, 2-pentyl- | Cyclopentol | 0.03790000 |
| 199. | 82461-14-1 | Furan, tetrahydro-2,4-dimethyl-4-phenyl- | Rhubafuran ® | 0.03780000 |
| 200. | 56011-02-0 | Benzene, [2-(3-methylbutoxy)ethyl]- | Phenyl Ethyl Isoamyl Ether | 0.03690000 |
| 201. | 103-37-7 | Butanoic acid, phenylmethyl ester | Benzyl Butyrate | 0.03660000 |
| 202. | 6378-65-0 | Hexyl hexanoate | Hexyl hexanoate | 0.03490000 |
| 203. | 118-61-6 | Benzoic acid, 2-hydroxy-, ethyl ester | Ethyl salicylate | 0.03480000 |
| 204. | 98-52-2 | Cyclohexanol, 4-(1,1-dimethylethyl)- | Patchon | 0.03480000 |
| 205. | 115-99-1 | 1,6-Octadien-3-ol, 3,7-dimethyl-, 3-formate | Linalyl Formate | 0.03440000 |
| 206. | 112-54-9 | Dodecanal | Lauric Aldehyde | 0.03440000 |
| 207. | 53046-97-2 | 3,6-Nonadien-1-ol, (3Z,6Z)- | 3,6 Nonadien-1-ol | 0.03360000 |
| 208. | 76649-25-7 | 3,6-Nonadien-1-ol | 3,6-Nonadien-1-ol | 0.03360000 |
| 209. | 141-25-3 | 3,7-Dimethyloct-6-en-1-ol | Rhodinol | 0.03290000 |
| 210. | 1975-78-6 | Decanenitrile | Decanonitrile | 0.03250000 |
| 211. | 2216-51-5 | Cyclohexanol, 5-methyl-2-(1-methylethyl)-, (1R,2S,5R)- | L-Menthol | 0.03230000 |
| 212. | 3658-77-3 | 4-hydroxy-2,5-dimethylfuran-3-one | Pineapple Ketone | 0.03200000 |
| 213. | 103-93-5 | Propanoic acid, 2-methyl-, 4-methylphenyl ester | Para Cresyl iso-Butyrate | 0.03120000 |
| 214. | 24717-86-0 | Propanoic acid, 2-methyl-, (1R,2S,4R)-1,7,7-trimethylbicyclo[2.2.1]hept-2-yl ester, rel- | Abierate | 0.03110000 |
| 215. | 67845-46-9 | Acetaldehyde, 2-(4-methylphenoxy)- | Aldehyde XI | 0.03090000 |
| 216. | 67883-79-8 | 2-Butenoic acid, 2-methyl-, (3Z)-3-hexen-1-yl ester, (2E)- | Cis-3-Hexenyl Tiglate | 0.03060000 |
| 217. | 33885-51-7 | Bicyclo[3.1.1]hept-2-ene-2-propanal, 6,6-dimethyl- | Pino Acetaldehyde | 0.03040000 |
| 218. | 105-85-1 | 6-Octen-1-ol, 3,7-dimethyl-, 1-formate | Citronellyl Formate | 0.03000000 |
| 219. | 70214-77-6 | 2-Nonanol, 6,8-dimethyl- | Nonadyl | 0.03010000 |
| 220. | 215231-33-7 | Cyclohexanol, 1-methyl-3-(2-methylpropyl)- | Rossitol | 0.02990000 |
| 221. | 120-72-9 | 1H-Indole | Indole | 0.02980000 |
| 222. | 2463-77-6 | 2-Undecenal | 2-Undecene-1-al | 0.02970000 |
| 223. | 675-09-2 | 2H-Pyran-2-one, 4,6-dimethyl- | Levistamel | 0.02940000 |
| 224. | 98-55-5 | 3-Cyclohexene-1-methanol, α,α,4-trimethyl- | Alpha-Terpineol | 0.02830000 |

TABLE 2-continued

Volatile Fragrance Materials

| No. | CAS Number | IUPAC Name | Common Name** | Vapor Pressure (Torr at 25° C.)* |
|---|---|---|---|---|
| 225. | 81786-73-4 | 3-Hepten-2-one, 3,4,5,6,6-pentamethyl-, (3Z)- | Koavone | 0.02750000 |
| 226. | 122-97-4 | Benzenepropanol | Phenyl Propyl Alcohol | 0.02710000 |
| 227. | 39212-23-2 | 2(3H)-Furanone, 5-butyldihydro-4-methyl- | Methyl Octalactone | 0.02700000 |
| 228. | 53767-93-4 | 7-Octen-2-ol, 2,6-dimethyl-, 2-acetate | Dihydro Terpinyl Acetate | 0.02690000 |
| 229. | 35044-59-8 | 1,3-Cyclohexadiene-1-carboxylic acid, 2,6,6-trimethyl-, ethyl ester | Ethyl Safranate | 0.02660000 |
| 230. | 104-55-2 | 2-Propenal, 3-phenyl- | Cinnamic Aldehyde | 0.02650000 |
| 231. | 144-39-8 | 1,6-Octadien-3-ol, 3,7-dimethyl-, 3-propanoate | Linalyl Propionate | 0.02630000 |
| 232. | 61931-80-4 | 1,6-Nonadien-3-ol, 3,7-dimethyl-, 3-acetate | 3,7-Dimethyl-1,6-nonadien-3-yl acetate | 0.02630000 |
| 233. | 102-13-6 | Benzeneacetic acid, 2-methylpropyl ester | Iso Butyl Phenylacetate | 0.02630000 |
| 234. | 65443-14-3 | Cyclopentanone, 2,2,5-trimethyl-5-pentyl- | Veloutone | 0.02610000 |
| 235. | 141-12-8 | 2,6-Octadien-1-ol, 3,7-dimethyl-, 1-acetate, (2Z)- | Neryl Acetate | 0.02560000 |
| 236. | 105-87-3 | 2,6-Octadien-1-ol, 3,7-dimethyl-, 1-acetate, (2E)- | Geranyl acetate | 0.02560000 |
| 237. | 68141-17-3 | Undecane, 1,1-dimethoxy-2-methyl- | Methyl Nonyl Acetaldehyde Dimethyl Acetal | 0.02550000 |
| 238. | 2206-94-2 | Benzenemethanol, α-methylene-, 1-acetate | Indocolore | 0.02550000 |
| 239. | 10528-67-3 | Cyclohexanepropanol, α-methyl- | Cyclohexylmagnol | 0.02550000 |
| 240. | 123-11-5 | Benzaldehyde, 4-methoxy- | Anisic Aldehyde | 0.02490000 |
| 241. | 57576-09-7 | Cyclohexanol, 5-methyl-2-(1-methylethenyl)-, 1-acetate, (1R,2S,5R)- | Iso Pulegol Acetate | 0.02480000 |
| 242. | 51566-62-2 | 6-Octenenitrile, 3,7-dimethyl- | Citronellyl Nitrile | 0.02470000 |
| 243. | 60335-71-9 | 2H-Pyran, 3,6-dihydro-4-methyl-2-phenyl- | Rosyrane Super | 0.02470000 |
| 244. | 30385-25-2 | 6-Octen-2-ol, 2,6-dimethyl- | Dihydromyrcenol | 0.02440000 |
| 245. | 101-84-8 | Benzene, 1,1'-oxybis- | Diphenyl Oxide | 0.02230000 |
| 246. | 136-60-7 | Benzoic acid, butyl ester | Butyl Benzoate | 0.02170000 |
| 247. | 93939-86-7 | 5,8-Methano-2H-1-benzopyran, 6-ethylideneoctahydro- | Rhuboflor | 0.02120000 |
| 248. | 83926-73-2 | Cyclohexanepropanol, α,α-dimethyl- | Coranol | 0.02100000 |
| 249. | 125109-85-5 | Benzenepropanal, β-methyl-3-(1-methylethyl)- | Florhydral | 0.02070000 |
| 250. | 104-21-2 | Benzenemethanol, 4-methoxy-, 1-acetate | Anisyl Acetate | 0.02050000 |
| 251. | 1365-19-1 | 2-Furanmethanol, 5-ethenyltetrahydro-α,α,5-trimethyl- | Linalool Oxide | 0.02050000 |
| 252. | 137-03-1 | Cyclopentanone, 2-heptyl- | Frutalone | 0.02040000 |
| 253. | 2563-07-7 | Phenol, 2-ethoxy-4-methyl- | Ultravanil | 0.02030000 |
| 254. | 1128-08-1 | 2-Cyclopenten-1-one, 3-methyl-2-pentyl- | Dihydrojasmone | 0.02020000 |
| 255. | 7493-57-4 | Benzene, [2-(1-propoxyethoxy)ethyl]- | Acetaldehyde | 0.01990000 |
| 256. | 141-25-3 | 7-Octen-1-ol, 3,7-dimethyl- | Rhodinol | 0.01970000 |
| 257. | 216970-21-7 | Bicyclo[4.3.1]decane, 3-methoxy-7,7-dimethyl-10-methylene- | 3-Methoxy-7,7-dimethyl-10-methylene-bicyclo[4.3.1]decane | 0.01960000 |
| 258. | 319002-92-1 | Propanoic acid, 2-(1,1-dimethylpropoxy)-, propyl ester, (2S)- | Sclareolate ® | 0.01960000 |
| 259. | 85-91-6 | Benzoic acid, 2-(methylamino)-, methyl ester | Dimethyl anthranilate | 0.01930000 |

TABLE 2-continued

Volatile Fragrance Materials

| No. | CAS Number | IUPAC Name | Common Name** | Vapor Pressure (Torr at 25° C.)* |
|---|---|---|---|---|
| 260. | 13828-37-0 | Cyclohexanemethanol, 4-(1-methylethyl)-, cis- | Mayol | 0.01920000 |
| 261. | 26330-65-4 | (E)-6-ethyl-3-methyloct-6-en-1-ol | Super Muguet | 0.01850000 |
| 262. | 7540-51-4 | 6-Octen-1-ol, 3,7-dimethyl-, (3S)- | L-Citronellol | 0.01830000 |
| 263. | 106-22-9 | 6-Octen-1-ol, 3,7-dimethyl- | Citronellol | 0.01830000 |
| 264. | 543-39-5 | 7-Octen-2-ol, 2-methyl-6-methylene- | Myrcenol | 0.01820000 |
| 265. | 7775-00-0 | Benzenepropanal, 4-(1-methylethyl)- | Cyclemax | 0.01820000 |
| 266. | 18479-54-4 | 4,6-Octadien-3-ol, 3,7-dimethyl- | Muguol | 0.01800000 |
| 267. | 29214-60-6 | Octanoic acid, 2-acetyl-, ethyl ester | Gelsone | 0.01790000 |
| 268. | 1209-61-6 | 5-Oxatricyclo[8.2.0.04,6]dodecane, 4,9,12,12-tetramethyl- | Tobacarol | 0.01730000 |
| 269. | 57934-97-1 | 2-Cyclohexene-1-carboxylic acid, 2-ethyl-6,6-dimethyl-, ethyl ester | Givescone | 0.01710000 |
| 270. | 14901-07-6 | 3-Buten-2-one, 4-(2,6,6-trimethyl-1-cyclohexen-1-yl)-, (3E)- | Beta-Ionone | 0.01690000 |
| 271. | 64001-15-6 | 4,7-Methano-1H-inden-5-ol, octahydro-, 5-acetate | Dihydro Cyclacet | 0.01630000 |
| 272. | 95-41-0 | 2-Cyclopenten-1-one, 2-hexyl- | Iso Jasmone T | 0.01600000 |
| 273. | 134-20-3 | Benzoic acid, 2-amino-, methyl ester | Methyl Anthranilate | 0.01580000 |
| 274. | 100-06-1 | Ethanone, 1-(4-methoxyphenyl)- | Para Methoxy Acetophenone | 0.01550000 |
| 275. | 105-86-2 | 2,6-Octadien-1-ol, 3,7-dimethyl-, 1-formate, (2E) | Geranyl Formate | 0.01540000 |
| 276. | 154171-77-4 | Spiro [1,3-dioxolane-2,8'(5'H)-[2H-2,4a]methanonaphthalene], hexahydro-1',1',5',5'-tetramethyl-, (2'S,4'aS,8'aS)- (9CI) | Ysamber K ® | 0.01470000 |
| 277. | 154171-76-3 | Spiro [1,3-dioxolane-2,8'(5'H)-[2H-2,4a]methanonaphthalene], hexahydro-1',1',5',5'-tetramethyl- | Ysamber | 0.01470000 |
| 278. | 127-41-3 | 3-Buten-2-one, 4-(2,6,6-trimethyl-2-cyclohexen-1-yl)-, (3E)- | Alpha-Ionone | 0.01440000 |
| 279. | 151-05-3 | Benzeneethanol, α,α-dimethyl-, 1-acetate | Dimethyl Benzyl Carbinyl Acetate | 0.01390000 |
| 280. | 2500-83-6 | 4,7-Methano-1H-inden-5-ol, 3a,4,5,6,7,7a-hexahydro-, 5-acetate | Flor Acetate | 0.01370000 |
| 281. | 150-84-5 | 6-Octen-1-ol, 3,7-dimethyl-, 1-acetate | Citronellyl acetate | 0.01370000 |
| 282. | 30310-41-9 | 2H-Pyran, tetrahydro-2-methyl-4-methylene-6-phenyl- | Pelargene | 0.01350000 |
| 283. | 68845-00-1 | Bicyclo[3.3.1]nonane, 2-ethoxy-2,6,6-trimethyl-9-methylene- | Boisiris | 0.01350000 |
| 284. | 106-24-1 | 2,6-Octadien-1-ol, 3,7-dimethyl-, (2E)- | Geraniol | 0.01330000 |
| 285. | 106-25-2 | 2,6-Octadien-1-ol, 3,7-dimethyl-, (2Z)- | Nerol | 0.01330000 |
| 286. | 75975-83-6 | Bicyclo[7.2.0]undec-4-ene, 4,11,11-trimethyl-8-methylene-, (1R,4E,9S)- | Vetyvenal | 0.01280000 |
| 287. | 19870-74-7 | 1H-3a,7-Methanoazulene, octahydro-6-methoxy-3,6,8,8-tetramethyl-, (3R,3aS,6S,7R,8aS)- | Cedryl methyl ether | 0.01280000 |

TABLE 2-continued

Volatile Fragrance Materials

| No. | CAS Number | IUPAC Name | Common Name** | Vapor Pressure (Torr at 25° C.)* |
|---|---|---|---|---|
| 288. | 87-44-5 | Bicyclo[7.2.0]undec-4-ene, 4,11,11-trimethyl-8-methylene-, (1R,4E,9S)- | Caryophyllene Extra | 0.01280000 |
| 289. | 54440-17-4 | 1H-Inden-1-one, 2,3-dihydro-2,3,3-trimethyl- | Safraleine | 0.01260000 |
| 290. | 110-98-5 | 2-Propanol, 1,1'-oxybis- | Dipropylene Glycol | 0.01250000 |
| 291. | 41890-92-0 | 2-Octanol, 7-methoxy-3,7-dimethyl- | Osyrol ® | 0.01250000 |
| 292. | 71077-31-1 | 4,9-Decadienal, 4,8-dimethyl- | Floral Super | 0.01230000 |
| 293. | 65-85-0 | Benzoic Acid | Benzoic Acid | 0.01220000 |
| 294. | 61444-38-0 | 3-Hexenoic acid, (3Z)-3-hexen-1-yl ester, (3Z)- | cis-3-hexenyl-cis-3-hexenoate | 0.01220000 |
| 295. | 116044-44-1 | Bicyclo[2.2.1]hept-5-ene-2-carboxylic acid, 3-(1-methylethyl)-, ethyl ester, (1R,2S,3S,4S)-rel- | Herbanate | 0.01210000 |
| 296. | 104-54-1 | 2-Propen-1-ol, 3-phenyl- | Cinnamic Alcohol | 0.01170000 |
| 297. | 78-35-3 | Propanoic acid, 2-methyl-, 1-ethenyl-1,5-dimethyl-4-hexen-1-yl ester | Linalyl Isobutyrate | 0.01170000 |
| 298. | 23495-12-7 | Ethanol, 2-phenoxy-, 1-propanoate | Phenoxy Ethyl Propionate | 0.01130000 |
| 299. | 103-26-4 | 2-Propenoic acid, 3-phenyl-, methyl ester | Methyl Cinnamate | 0.01120000 |
| 300. | 67634-14-4 | Benzenepropanal, 2-ethyl-α,α-dimethyl- | Florazon (ortho-isomer) | 0.01110000 |
| 301. | 5454-19-3 | Propanoic acid, decyl ester | N-Decyl Propionate | 0.01100000 |
| 302. | 93-16-3 | Benzene, 1,2-dimethoxy-4-(1-propen-1-yl)- | Methyl Iso Eugenol | 0.01100000 |
| 303. | 81782-77-6 | 3-Decen-5-ol, 4-methyl- | 4-Methyl-3-decen-5-ol | 0.01070000 |
| 304. | 67845-30-1 | Bicyclo[2.2.2]oct-5-ene-2-carboxaldehyde, 6-methyl-8-(1-methylethyl)- | Maceal | 0.01060000 |
| 305. | 97-53-0 | Phenol, 2-methoxy-4-(2-propen-1-yl)- | Eugenol | 0.01040000 |
| 306. | 120-57-0 | 1,3-Benzodioxole-5-carboxaldehyde | Heliotropin | 0.01040000 |
| 307. | 93-04-9 | Naphthalene, 2-methoxy- | Beta Naphthyl Methyl Ether Extra 99 | 0.01040000 |
| 308. | 4826-62-4 | 2-Dodecenal | 2 Dodecene-1-al | 0.01020000 |
| 309. | 20407-84-5 | 2-Dodecenal, (2E)- | Aldehyde Mandarin | 0.01020000 |
| 310. | 5462-06-6 | Benzenepropanal, 4-methoxy-α-methyl- | Canthoxal | 0.01020000 |
| 311. | 94-60-0 | 1,4-Cyclohexanedicarboxylic acid, 1,4-dimethyl ester | Dimethyl 1,4-cyclohexanedicarboxylate | 0.01020000 |
| 312. | 57378-68-4 | 2-Buten-1-one, 1-(2,6,6-trimethyl-3-cyclohexen-1-yl)- | delta-Damascone | 0.01020000 |
| 313. | 17283-81-7 | 2-Butanone, 4-(2,6,6-trimethyl-1-cyclohexen-1-yl)- | Dihydro Beta Ionone | 0.01020000 |
| 314. | 1885-38-7 | 2-Propenenitrile, 3-phenyl-, (2E)- | Cinnamalva | 0.01010000 |
| 315. | 103-48-0 | Propanoic acid, 2-methyl-, 2-phenylethyl ester | Phenyl Ethyl Iso Butyrate | 0.00994000 |
| 316. | 488-10-8 | 2-Cyclopenten-1-one, 3-methyl-2-(2Z)-2-penten-1-yl- | Cis Jasmone | 0.00982000 |
| 317. | 7492-67-3 | Acetaldehyde, 2-[(3,7-dimethyl-6-octen-1-yl)oxy]- | Citronellyloxyacetaldehyde | 0.00967000 |
| 318. | 68683-20-5 | 1-Cyclohexene-1-ethanol, 4-(1-methylethyl)-, 1-formate | Iso Bergamate | 0.00965000 |
| 319. | 3025-30-7 | 2,4-Decadienoic acid, ethyl ester, (2E,4Z)- | Ethyl 2,4-Decadienoate | 0.00954000 |
| 320. | 103-54-8 | 2-Propen-1-ol, 3-phenyl-, 1-acetate | Cinnamyl Acetate | 0.00940000 |
| 321. | 18127-01-0 | Benzenepropanal, 4-(1,1-dimethylethyl)- | Bourgeonal | 0.00934000 |

TABLE 2-continued

Volatile Fragrance Materials

| No. | CAS Number | IUPAC Name | Common Name** | Vapor Pressure (Torr at 25° C.)* |
|---|---|---|---|---|
| 322. | 3738-00-9 | Naphtho[2,1-b]furan, dodecahydro-3a,6,6,9a-tetramethyl- | Ambrox ® or Cetalox ® or Synambran | 0.00934000 |
| 323. | 51519-65-4 | 1,4-Methanonaphthalen-5(1H)-one, 4,4a,6,7,8,8a-hexahydro- | Tamisone | 0.00932000 |
| 324. | 148-05-1 | Dodecanoic acid, 12-hydroxy-, λ-lactone (6CI,7CI); 1,12- | Dodecalactone | 0.00931000 |
| 325. | 6790-58-5 | (3aR,5aS,9aS,9bR)-3a,6,6,9a-tetramethyl-2,4,5,5a,7,8,9,9b-octahydro-1H-benzo[e][1]benzofuran | Ambronat ® or Ambroxan ® | 0.00930000 |
| 326. | 86-26-0 | 1,1'-Biphenyl, 2-methoxy- | Methyl Diphenyl Ether | 0.00928000 |
| 327. | 68738-94-3 | 2-Naphthalenecarboxaldehyde, octahydro-8,8-dimethyl | Cyclomyral ® | 0.00920000 |
| 328. | 2705-87-5 | Cyclohexanepropanoic acid, 2-propen-1-yl ester | Allyl Cyclohexane Propionate | 0.00925000 |
| 329. | 7011-83-8 | 2(3H)-Furanone, 5-hexyldihydro-5-methyl- | Lactojasmone ® | 0.00885000 |
| 330. | 61792-11-8 | 2,6-Nonadienenitrile, 3,7-dimethyl- | Lemonile ® | 0.00884000 |
| 331. | 692-86-4 | 10-Undecenoic acid, ethyl ester | Ethyl Undecylenate | 0.00882000 |
| 332. | 103-95-7 | Benzenepropanal, α-methyl-4-(1-methylethyl)- | Cymal | 0.00881000 |
| 333. | 13019-22-2 | 9-Decen-1-ol | Rosalva | 0.00879000 |
| 334. | 94201-19-1 | 1-Oxaspiro[4.5]decan-2-one, 8-methyl- | Methyl Laitone 10% TEC | 0.00872000 |
| 335. | 104-61-0 | 2(3H)-Furanone, dihydro-5-pentyl- | γ-Nonalactone | 0.00858000 |
| 336. | 706-14-9 | 2(3H)-Furanone, 5-hexyldihydro- | γ-Decalactone | 0.00852000 |
| 337. | 24720-09-0 | 2-Buten-1-one, 1-(2,6,6-trimethyl-2-cyclohexen-1-yl)-, (2E)- | α-Damascone | 0.00830000 |
| 338. | 39872-57-6 | 2-Buten-1-one, 1-(2,4,4-trimethyl-2-cyclohexen-1-yl)-, (2E)- | Isodamascone | 0.00830000 |
| 339. | 705-86-2 | 2H-Pyran-2-one, tetrahydro-6-pentyl- | Decalactone | 0.00825000 |
| 340. | 67634-15-5 | Benzenepropanal, 4-ethyl-α,α-dimethyl- | Floralozone | 0.00808000 |
| 341. | 40527-42-2 | 1,3-Benzodioxole, 5-(diethoxymethyl)- | Heliotropin Diethyl Acetal | 0.00796000 |
| 342. | 56973-85-4 | 4-Penten-1-one, 1-(5,5-dimethyl-1-cyclohexen-1-yl)- | Neobutenone α | 0.00763000 |
| 343. | 128-51-8 | Bicyclo[3.1.1]hept-2-ene-2-ethanol, 6,6-dimethyl-, 2-acetate | Nopyl Acetate | 0.00751000 |
| 344. | 103-36-6 | 2-Propenoic acid, 3-phenyl-, ethyl ester | Ethyl Cinnamate | 0.00729000 |
| 345. | 5182-36-5 | 1,3-Dioxane, 2,4,6-trimethyl-4-phenyl- | Floropal ® | 0.00709000 |
| 346. | 42604-12-6 | Cyclododecane, (methoxymethoxy)- | Boisambrene | 0.00686000 |
| 347. | 33885-52-8 | Bicyclo[3.1.1]hept-2-ene-2-propanal, α,α,6,6-tetramethyl- | Pinyl Iso Butyrate Alpha | 0.00685000 |
| 348. | 92015-65-1 | 2(3H)-Benzofuranone, hexahydro-3,6-dimethyl- | Natactone | 0.00680000 |
| 349. | 63767-86-2 | Cyclohexanemethanol, α-methyl-4-(1-methylethyl)- | Mugetanol | 0.00678000 |
| 350. | 3288-99-1 | Benzeneacetonitrile, 4-(1,1-dimethylethyl)- | Marenil CI | 0.00665000 |
| 351. | 35044-68-9 | 2-Buten-1-one, 1-(2,6,6-trimethyl-1-cyclohexen-1-yl)- | beta-Damascone | 0.00655000 |

TABLE 2-continued

Volatile Fragrance Materials

| No. | CAS Number | IUPAC Name | Common Name** | Vapor Pressure (Torr at 25° C.)* |
|---|---|---|---|---|
| 352. | 41724-19-0 | 1,4-Methanonaphthalen-6(2H)-one, octahydro-7-methyl- | Plicatone | 0.00652000 |
| 353. | 75147-23-8 | Bicyclo[3.2.1]octan-8-one, 1,5-dimethyl-, oxime | Buccoxime ® | 0.00647000 |
| 354. | 25634-93-9 | 2-Methyl-5-phenylpentan-1-ol | Rosaphen ® 600064 | 0.00637000 |
| 355. | 55066-48-3 | 3-Methyl-5-phenylpentanol | Phenyl Hexanol | 0.00637000 |
| 356. | 495-62-5 | Cyclohexene, 4-(1,5-dimethyl-4-hexen-1-ylidene)-1-methyl- | Bisabolene | 0.00630000 |
| 357. | 2785-87-7 | Phenol, 2-methoxy-4-propyl- | Dihydro Eugenol | 0.00624000 |
| 358. | 87-19-4 | Benzoic acid, 2-hydroxy-, 2-methylpropyl ester | Iso Butyl Salicylate | 0.00613000 |
| 359. | 4430-31-3 | 2H-1-Benzopyran-2-one, octahydro- | Octahydro Coumarin | 0.00586000 |
| 360. | 38462-22-5 | Cyclohexanone, 2-(1-mercapto-1-methylethyl)-5-methyl- | Ringonol 50 TEC | 0.00585000 |
| 361. | 77-83-8 | 2-Oxiranecarboxylic acid, 3-methyl-3-phenyl-, ethyl ester | Ethyl Methyl Phenyl Glycidate | 0.00571000 |
| 362. | 37677-14-8 | 3-Cyclohexene-1-carboxaldehyde, 4-(4-methyl-3-penten-1-yl)- | Iso Hexenyl Cyclohexenyl Carboxaldehyde | 0.00565000 |
| 363. | 103-60-6 | Propanoic acid, 2-methyl-, 2-phenoxyethyl ester | Phenoxy Ethyl iso-Butyrate | 0.00562000 |
| 364. | 18096-62-3 | Indeno [1,2-d]-1,3-dioxin, 4,4a,5,9b-tetrahydro- | Indoflor ® | 0.00557000 |
| 365. | 63500-71-0 | 2H-Pyran-4-ol, tetrahydro-4-methyl-2-(2-methylpropyl)- | Florosa Q/Florol | 0.00557000 |
| 366. | 65405-84-7 | Cyclohexanebutanal, α,2,6,6-tetramethyl- | Cetonal ® | 0.00533000 |
| 367. | 171102-41-3 | 4,7-Methano-1H-inden-6-ol, 3a,4,5,6,7,7a-hexahydro-8,8-dimethyl-, 6-acetate | Flor Acetate | 0.00530000 |
| 368. | 10339-55-6 | 1,6-Nonadien-3-ol, 3,7-dimethyl- | Ethyl linalool | 0.00520000 |
| 369. | 23267-57-4 | 3-Buten-2-one, 4-(2,2,6-trimethyl-7-oxabicyclo[4.1.0]hept-1-yl)- | Ionone Epoxide Beta | 0.00520000 |
| 370. | 97-54-1 | Phenol, 2-methoxy-4-(1-propen-1-yl)- | Isoeugenol | 0.00519000 |
| 371. | 67663-01-8 | 2(3H)-Furanone, 5-hexyldihydro-4-methyl- | Peacholide | 0.00512000 |
| 372. | 33885-52-8 | Bicyclo[3.1.1]hept-2-ene-2-propanal, α,α,6,6-tetramethyl- | Pinyl Iso Butyrate Alpha | 0.00512000 |
| 373. | 23696-85-7 | 2-Buten-1-one, 1-(2,6,6-trimethyl-1,3-cyclohexadien-1-yl)- | Damascenone | 0.00503000 |
| 374. | 80-71-7 | 2-Cyclopenten-1-one, 2-hydroxy-3-methyl- | Maple Lactone | 0.00484000 |
| 375. | 67662-96-8 | Propanoic acid, 2,2-dimethyl-, 2-phenylethyl ester | Pivarose Q | 0.00484000 |
| 376. | 2437-25-4 | Dodecanenitrile | Clonal | 0.00480000 |
| 377. | 141-14-0 | 6-Octen-1-ol, 3,7-dimethyl-, 1-propanoate | Citronellyl Propionate | 0.00469000 |
| 378. | 54992-90-4 | 3-Buten-2-one, 4-(2,2,3,6-tetramethylcyclohexyl)- | Myrrhone | 0.00460000 |
| 379. | 55066-49-4 | Benzenepentanal, β-methyl- | Mefranal | 0.00455000 |
| 380. | 7493-74-5 | Acetic acid, 2-phenoxy-, 2-propen-1-yl ester | Allyl Phenoxy Acetate | 0.00454000 |
| 381. | 80-54-6 | 4-(1,1-dimethylethyl)-α-methylbenzenepropanal | Lilial ® | 0.00444000 |

TABLE 2-continued

Volatile Fragrance Materials

| No. | CAS Number | IUPAC Name | Common Name** | Vapor Pressure (Torr at 25° C.)* |
|---|---|---|---|---|
| 382. | 86803-90-9 | 4,7-Methano-1H-indene-2-carboxaldehyde, octahydro-5-methoxy- | Scentenal ® | 0.00439000 |
| 383. | 68991-97-9 | 2-Naphthalenecarboxaldehyde, 1,2,3,4,5,6,7,8-octahydro-8,8-dimethyl- | Melafleur | 0.00436000 |
| 384. | 18871-14-2 | Pentitol, 1,5-anhydro-2,4-dideoxy-2-pentyl-, 3-acetate | Jasmal | 0.00434000 |
| 385. | 58567-11-6 | Cyclododecane, (ethoxymethoxy)- | Boisambren Forte | 0.00433000 |
| 386. | 94400-98-3 | Naphth[2,3-b]oxirene, 1a,2,3,4,5,6,7,7a-octahydro-1a,3,3,4,6,6-hexamethyl-, (1aR,4S,7aS)-rel- | Molaxone | 0.00425000 |
| 387. | 79-69-6 | 3-Buten-2-one, 4-(2,5,6,6-tetramethyl-2-cyclohexen-1-yl)- | alpha-Irone | 0.00419000 |
| 388. | 65442-31-1 | Quinoline, 6-(1-methylpropyl)- | Iso Butyl Quinoline | 0.00408000 |
| 389. | 87731-18-8 | Carbonic acid, 4-cycloocten-1-yl methyl ester | Violiff | 0.00401000 |
| 390. | 173445-65-3 | 1H-Indene-5-propanal, 2,3-dihydro-3,3-dimethyl- | Hivernal (A-isomer) | 0.00392000 |
| 391. | 23911-56-0 | Ethanone, 1-(3-methyl-2-benzofuranyl)- | Nerolione | 0.00383000 |
| 392. | 52474-60-9 | 3-Cyclohexene-1-carboxaldehyde, 1-methyl-3-(4-methyl-3-penten-1-yl)- | Precyclemone B | 0.00381000 |
| 393. | 139539-66-5 | 6-Oxabicyclo[3.2.1]octane, 5-methyl-1-(2,2,3-trimethyl-3-cyclopenten-1-yl)- | Cassifix | 0.00381000 |
| 394. | 80858-47-5 | Benzene, [2-(cyclohexyloxy)ethyl]- | Phenafleur | 0.00380000 |
| 395. | 32764-98-0 | 2H-Pyran-2-one, tetrahydro-6-(3-penten-1-yl)- | Jasmolactone | 0.00355000 |
| 396. | 78417-28-4 | 2,4,7-Decatrienoic acid, ethyl ester | Ethyl 2,4,7-decatrienoate | 0.00353000 |
| 397. | 140-26-1 | Butanoic acid, 3-methyl-, 2-phenylethyl ester | Beta Phenyl Ethyl Isovalerate | 0.00347000 |
| 398. | 105-90-8 | 2,6-Octadien-1-ol, 3,7-dimethyl-, 1-propanoate, (2E)- | Geranyl Propionate | 0.003360000 |
| 399. | 41816-03-9 | Spiro[1,4-methanonaphthalene-2(1H),2'-oxirane], 3,4,4a,5,8,8a-hexahydro-3',7-dimethyl- | Rhubofix ® | 0.00332000 |
| 400. | 7070-15-7 | Ethanol, 2-[[(1R,2R,4R)-1,7,7-trimethylbicyclo[2.2.1]hept-2-yl]oxy]-, rel- | Arbanol | 0.00326000 |
| 401. | 93-29-8 | Phenol, 2-methoxy-4-(1-propen-1-yl)-, 1-acetate | Iso Eugenol Acetate | 0.00324000 |
| 402. | 476332-65-7 | 2H-Indeno[4,5-b]furan, decahydro-2,2,6,6,7,8,8-heptamethyl- | Amber Xtreme Compound 1 | 0.00323000 |
| 403. | 68901-15-5 | Acetic acid, 2-(cyclohexyloxy)-, 2-propen-1-yl ester | Cyclogalbanate | 0.00323000 |
| 404. | 107-75-5 | Octanal, 7-hydroxy-3,7-dimethyl- | Hydroxycitronellal | 0.00318000 |
| 405. | 68611-23-4 | Naphtho[2,1-b]furan, 9b-ethyldodecahydro-3a,7,7-trimethyl- | Grisalva | 0.00305000 |
| 406. | 313973-37-4 | 1,6-Heptadien-3-one, 2-cyclohexyl- | Pharaone | 0.00298000 |
| 407. | 137-00-8 | 5-Thiazoleethanol, 4-methyl- | Sulfurol | 0.00297000 |
| 408. | 7779-30-8 | 1-Penten-3-one, 1-(2,6,6-trimethyl-2-cyclohexen-1-yl)- | Methyl Ionone | 0.00286000 |

TABLE 2-continued

Volatile Fragrance Materials

| No. | CAS Number | IUPAC Name | Common Name** | Vapor Pressure (Torr at 25° C.)* |
|---|---|---|---|---|
| 409. | 127-51-5 | 3-Buten-2-one, 3-methyl-4-(2,6,6-trimethyl-2-cyclohexen-1-yl)- | Isoraldeine Pure | 0.00282000 |
| 410. | 72903-27-6 | 1,4-Cyclohexanedicarboxylic acid, 1,4-diethyl ester | Fructalate ™ | 0.00274000 |
| 411. | 7388-22-9 | 3-Buten-2-one, 4-(2,2-dimethyl-6-methylenecyclohexyl)-3-methyl- | Ionone Gamma Methyl | 0.00272000 |
| 412. | 104-67-6 | 2(3H)-Furanone, 5-heptyldihydro- | gamma-Undecalactone (racemic) | 0.00271000 |
| 413. | 1205-17-0 | 1,3-Benzodioxole-5-propanal, α-methyl- | Helional | 0.00270000 |
| 414. | 33704-61-9 | 4H-Inden-4-one, 1,2,3,5,6,7-hexahydro-1,1,2,3,3-pentamethyl- | Cashmeran | 0.00269000 |
| 415. | 36306-87-3 | Cyclohexanone, 4-(1-ethoxyethenyl)-3,3,5,5-tetramethyl- | Kephalis | 0.00269000 |
| 416. | 97384-48-0 | Benzenepropanenitrile, α-ethenyl-α-methyl- | Citrowanil ® B | 0.00265000 |
| 417. | 141-13-9 | 9-Undecenal, 2,6,10-trimethyl- | Adoxal | 0.00257000 |
| 418. | 2110-18-1 | Pyridine, 2-(3-phenylpropyl)- | Corps Racine VS | 0.00257000 |
| 419. | 27606-09-3 | Indeno[1,2-d]-1,3-dioxin, 4,4a,5,9b-tetrahydro-2,4-dimethyl- | Magnolan | 0.00251000 |
| 420. | 67634-20-2 | Propanoic acid, 2-methyl-, 3a,4,5,6,7,7a-hexahydro-4,7-methano-1H-inden-5-yl ester | Cyclabute | 0.00244000 |
| 421. | 65405-72-3 | 1-Naphthalenol, 1,2,3,4,4a,7,8,8a-octahydro-2,4a,5,8a-tetramethyl-, 1-formate | Oxyoctaline Formate | 0.00236000 |
| 422. | 122-40-7 | Heptanal, 2-(phenylmethylene)- | Amyl Cinnamic Aldehyde | 0.00233000 |
| 423. | 103694-68-4 | Benzenepropanol, β,β,3-trimethyl- | Majantol ® | 0.00224000 |
| 424. | 13215-88-8 | 2-Cyclohexen-1-one, 4-(2-buten-1-ylidene)-3,5,5-trimethyl- | Tabanone Coeur | 0.00223000 |
| 425. | 25152-85-6 | 3-Hexen-1-ol, 1-benzoate, (3Z)- | Cis-3-Hexenyl Benzoate | 0.00203000 |
| 426. | 406488-30-0 | 2-Ethyl-N-methyl-N-(m-tolyl)butanamide | Paradisamide | 0.00200000 |
| 427. | 121-33-5 | Benzaldehyde, 4-hydroxy-3-methoxy- | Vanillin | 0.00194000 |
| 428. | 77-54-3 | 1H-3a,7-Methanoazulen-6-ol, octahydro-3,6,8,8-tetramethyl-, 6-acetate, (3R,3aS,6R,7R,8aS)- | Cedac | 0.00192000 |
| 429. | 76842-49-4 | 4,7-Methano-1H-inden-6-ol, 3a,4,5,6,7,7a-hexahydro-8,8-dimethyl-, 6-propanoate | Frutene | 0.00184000 |
| 430. | 121-39-1 | 2-Oxiranecarboxylic acid, 3-phenyl-, ethyl ester | Ethyl Phenyl Glycidate | 0.00184000 |
| 431. | 211299-54-6 | 4H-4a,9-Methanoazuleno[5,6-d]-1,3-dioxole, octahydro-2,2,5,8,8,9a-hexamethyl-, (4aR,5R,7aS,9R)- | Ambrocenide ® | 0.00182000 |
| 432. | 285977-85-7 | (2,5-Dimethyl-1,3-dihydroinden-2-yl)methanol | Lilyflore | 0.00180000 |
| 433. | 10094-34-5 | Butanoic acid, 1,1-dimethyl-2-phenylethyl ester | Dimethyl Benzyl Carbinyl Butyrate | 0.00168000 |
| 434. | 40785-62-4 | Cyclododeca[c]furan, 1,3,3a,4,5,6,7,8,9,10,11,13a-dodecahydro- | Muscogene | 0.00163000 |
| 435. | 75490-39-0 | Benzenebutanenitrile, α,α,γ-trimethyl- | Khusinil | 0.00162000 |
| 436. | 55418-52-5 | 2-Butanone, 4-(1,3-benzodioxol-5-yl)- | Dulcinyl | 0.00161000 |
| 437. | 3943-74-6 | Benzoic acid, 4-hydroxy-3-methoxy-, methyl ester | Carnaline | 0.00157000 |

TABLE 2-continued

Volatile Fragrance Materials

| No. | CAS Number | IUPAC Name | Common Name** | Vapor Pressure (Torr at 25° C.)* |
|---|---|---|---|---|
| 438. | 72089-08-8 | 3-Cyclopentene-1-butanol, β,2,2,3-tetramethyl- 2-Methyl-4-(2,2,3-trimethyl-3-cyclopenten-1-yl)butanol | Brahmanol ® | 0.00154000 |
| 439. | 3155-71-3 | 2-Butenal, 2-methyl-4-(2,6,6-trimethyl-1-cyclohexen-1-yl)- | Boronal | 0.00147000 |
| 440. | 2050-08-0 | Benzoic acid, 2-hydroxy-, pentyl ester | Amyl Salicylate | 0.00144000 |
| 441. | 41199-20-6 | 2-Naphthalenol, decahydro-2,5,5-trimethyl- | Ambrinol | 0.00140000 |
| 442. | 12262-03-2 | ndecanoic acid, 3-methylbutyl ester | Iso Amyl Undecylenate | 0.00140000 |
| 443. | 107-74-4 | 1,7-Octanediol, 3,7-dimethyl- | Hydroxyol | 0.00139000 |
| 444. | 91-64-5 | 2H-1-Benzopyran-2-one | Coumarin | 0.00130000 |
| 445. | 68901-32-6 | 1,3-Dioxolane, 2-[6-methyl-8-(1-methylethyl) bicyclo[2.2.2]oct-5-en-2-yl]- | Glycolierral | 0.00121000 |
| 446. | 68039-44-1 | Propanoic acid, 2,2-dimethyl-, 3a,4,5,6,7,7a-hexahydro-4,7-methano-1H-inden-6-yl ester | Pivacyclene | 0.00119000 |
| 447. | 106-29-6 | Butanoic acid, (2E)-3,7-dimethyl-2,6-octadien-1-yl ester | Geranyl Butyrate | 0.00116000 |
| 448. | 5471-51-2 | 2-Butanone, 4-(4-hydroxyphenyl)- | Raspberry ketone | 0.00106000 |
| 449. | 109-42-2 | 10-Undecenoic acid, butyl ester | Butyl Undecylenate | 0.00104000 |

*Vapor Pressures are acquired as described in the Test Methods Section.
**Origin: Same as for Table 1 hereinabove.

Preferably, the compositions of the present invention are those where the volatile fragrance material is selected from the group consisting of Table 2 Volatile Fragrance Materials 4, 6, 18, 54, 60, 77, 92, 105, 107, 119, 122, 134, 138, 141, 144, 148, 152, 155, 158, 167, 173, 175, 176, 182, 186, 189, 193, 195, 196, 202, 205, 206, 207, 210, 212, 225, 235, 238, 243, 245, 257, 271, 273, 274, 279-280, 282, 285, 289, 293, 297, 302, 305-306, 314, 315, 318, 354-355, 410, 416, and mixtures thereof.

Modulators

In one aspect, compositions of the present invention comprise at least one substantially non-odorous modulator selected from the group consisting of (a) sucrose laurate, sucrose dilaurate, sucrose myristate, sucrose palmitate, sucrose stearate, sucrose distearate, sucrose tristearate, and mixtures thereof;

(b) trimethylcyclohexane derivatives having the formula (I):

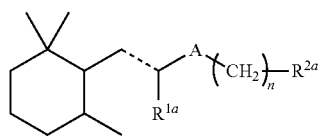

(I)

wherein:

n is 0, 1 or 2;

A is —C(O)— or —CH(OH)—;

$R^{1a}$ is hydrogen or methyl;

$R^{2a}$ is a $C_2$-$C_{10}$ hydrocarbon group; and

------ is a saturated or unsaturated carbon-carbon bond;

(c) L-menthoxy ether derivatives having the formula (II):

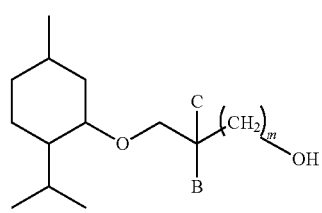

(II)

wherein:

m is 0, 1 or 2;

B is hydrogen or —OH; and

C is hydrogen or methyl;

(d) tetra-hydronaphthalene derivatives having the formula (III):

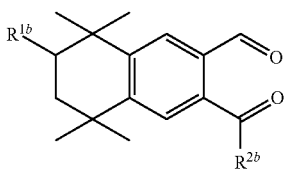

(III)

wherein:
R$^{1b}$ is hydrogen or methyl; and
R$^{2b}$ is alkyl;
(e) hyaluronic acid disaccharide sodium salt, sodium hyaluronate and their mixtures;
(f) Ether derivatives having the formula (IV) or formula (V):

  (IV)

wherein:
C$_5$H$_l$O$_m$ is a pentose residue, wherein l is an integer from 6 to 9, and m is an integer from 1 to 4;
n is an integer from 1 to 4; and
R$^{1c}$ is C$_4$-C$_{20}$ hydrocarbon group; and

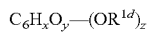  (V)

wherein:
C$_6$H$_x$O$_y$ is a hexose residue, wherein x is an integer from 7 to 11, and y is an integer from 1 to 5;
z is an integer from 1 to 5; and
R$^{1d}$ is C$_4$-C$_{20}$ hydrocarbon group; and (g) Diethylene Glycol Ether derivatives having the formula (VI) or formula (VII):

  (VI)

wherein:
C$_5$H$_c$O$_d$ is a pentose residue, wherein c is an integer from 6 to 8, and d is an integer from 1 to 3;
e is an integer from 2 to 4; and
R$^{1e}$ is C$_1$-C$_6$ alkyl group;

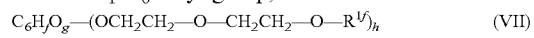  (VII)

wherein:
C$_6$H$_f$O$_g$ is a hexose residue, wherein f is an integer from 7 to 10, and g is an integer from 1 to 4;
h is an integer from 2 to 5; and
R$^{1f}$ is C$_1$-C$_6$ alkyl group;

(h) Hydroquinone Glycoside derivatives having the formula (VIII):

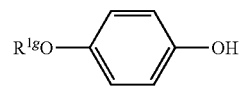  (VIII)

wherein:
R$^{1g}$ is selected from the group consisting of: (i) pentose residue, hexose residue, aminosaccharide residue, uronic acid residue and their mixtures; (ii) methylated versions of group (i); and (iii) mixtures of groups (i) and (ii).
(i) mixtures thereof.

Preferably the substantially non-odorous fragrance modulator is selected from the group consisting of materials disclosed in Table 3.

TABLE 3

Substantially Non-Odorous Fragrance Modulators

| No. | Group | IUPAC or INCI name | CAS Number | Supplier |
|---|---|---|---|---|
| 1. | (a) | Sucrose laurate | 25339-99-5 | Alfa Chemicals Ltd. (UK) |
| 2. | | Sucrose dilaurate | 25915-57-5 | Alfa Chemicals Ltd. (UK) |
| 3. | | Sucrose myristate | 27216-47-3 | Mitsubishi Chemicals |
| 4. | | Sucrose palmitate | 26446-38-8 | Alfa Chemicals |
| 5. | | Sucrose stearate | 25168-73-4 | Ltd. (UK) |
| 6. | | Sucrose Distearate | 27195-16-0 | Mitsubishi Chemicals (JP) |
| 7. | | Sucrose Tristearate | 27923-63-3 | Mitsubishi Chemicals (JP) |
| 8. | (b) | (E)-1-(2,2,6-trimethylcyclohexyl)oct-1-en-3-one [1] | — | Takasago (Japan) |
| 9. | (c) | 2-(l-menthoxy)ethane-1-ol [2] | — | Takasago (Japan) |
| 10. | | 1-(l-menthoxy)propane-2-ol [2] | — | |
| 11. | | 3-(l-menthoxy)propane-1-ol [2] | — | |
| 12. | | 3-(l-menthoxy)propane-1,2-diol [2] | — | |
| 13. | | 2-methyl-3-(1-menthoxy)propane-1,2-diol [2] | — | |
| 14. | | 4-(1-menthoxy) butane-1-ol [2] | — | |
| 15. | (d) | 1,1,4,4-tetramethyl-6-acetyl-7-formyl-1,2,3,4-tetrahydronaphthalene [3] | — | Givaudan (Switzerland) |
| 16. | | 1,1,2,4,4-pentamethyl-6-acetyl-7-formyl-1,2,3,4-tetrahydronaphthalene [3] | — | |
| 17. | (e) | Hyaluronic acid disaccharide sodium salt [4] | 9004-61-9 | Sigma Aldrich (USA) |
| 18. | | Sodium Hyaluronate [4] | 9067-32-7 | Soliance (France) |
| 19. | (f) | Mono-o-(linalyl)-glucopyranose [5] | — | Kanebo (Japan) |
| 20. | | Di-o-(linalyl)-glucopyranose [5] | — | |
| 21. | | Tri-o-(linalyl)-glucopyranose [5] | — | |
| 22. | | Tetra-o-(linalyl)-glucopyranose [5] | — | |

TABLE 3-continued

Substantially Non-Odorous Fragrance Modulators

| No. | Group | IUPAC or INCI name | CAS Number | Supplier |
|---|---|---|---|---|
| 23. | | Penta-o-(linalyl)-glucopyranose [5] | — | |
| 24. | | Mono-o-(cis-3-hexenyl)-glactopyranose [5] | — | |
| 25. | | Di-o-(cis-3-hexenyl)-glactopyranose [5] | — | |
| 26. | | Tri-o-(cis-3-hexenyl)-glactopyranose [5] | — | |
| 27. | | Tetra-o-(cis-3-hexenyl)-glactopyranose [5] | — | |
| 28. | | Penta-o-(cis-3-hexenyl)-glactopyranose [5] | — | |
| 29. | (g) | Bis-O-(3,6-dioxadecanyl)-glucopyranose [6] | — | Kanebo (Japan) |
| 30. | | Tris-O-(3,6-dioxadecanyl)-glucopyranose [6] | — | |
| 31. | | Tetrakis-O-(3,6-dioxadecanyl)-glucopyranose [6] | — | |
| 32. | | Pentakis-O-(3,6-dioxadecanyl)-glucopyranose [6] | — | |
| 33. | | Bis-O-(3,6-dioxaoctanyl)-galactopyranose [6] | — | |
| 34. | | Tris-O-(3,6-dioxaoctanyl)-galactopyranose [6] | — | |
| 35. | | Tetrakis-O-(3,6-dioxaoctanyl)-galactopyranose [6] | — | |
| 36. | | Pentakis-O-(3,6-dioxaoctanyl)-galactopyranose [6] | — | |
| 37. | | Bis-O-(3,6-dioxaheptanyl)-xylopyranose [6] | — | |
| 38. | | Tris-O-(3,6-dioxaheptanyl)-xylopyranose [6] | — | |
| 39. | | Tetrakis-O-(3,6-dioxaheptanyl)-xylopyranose [6] | — | |
| 40. | | Bis-O-(3,6-dioxadodecanyl)-glucopyranose [6] | — | |
| 41. | | Tris-O-(3,6-dioxadodecanyl)-glucopyranose [6] | — | |
| 42. | | Tetrakis-O-(3,6-dioxadodecanyl)-glucopyranose [6] | — | |
| 43. | | Pentakis-O-(3,6-dioxadodecanyl)-glucopyranose [6] | — | |
| 44. | (h) | Hydroquinone beta-D-glycoside [7] | 497-76-7 | Sigma Aldrich |

[1] U.S. Pat. No. 6,440,400B1 (Takasago Int. Corp.), column 5, compound 1'i.
[2] U.S. Pat. No. 7,538,081B2 (Takasago Int. Corp.), column 7, lines 50-53.
[3] U.S. Pat. No. 6,147,049 (Givaudan Roure), column 5, line 24, to column 6, line 17.
[4] PCT Publication No. WO85/04803 (Diagnostica), pg. 2, line 1 to pg. 4, line 2.
[5] JP Patent No. 61-083114 (Kanebo).
[6] JP Patent No. 61-063612 (Kanebo).
[7] JP Patent No. 62-084010 (Shiseido).

The compounds, as described above in Table 3 and mixtures thereof, act as a substantially non-odorous fragrance modulator of the perceived intensity and/or longevity of the fragrance profile of the composition of the present invention when low levels of the low volatile fragrance materials are used. For example, the substantially non-odorous fragrance modulators, with a fragrance component having low levels of the low volatile fragrance materials, act to prolong the duration during which the fragrance profile, preferably the characters attributable from the volatile fragrance materials, can be perceived as compared to a control composition in the absence of the modulators or having the traditional high levels of the low volatile fragrance materials. As another example, the substantially non-odorous fragrance modulators with a fragrance component having low levels of the low volatile fragrance materials, can improve the fidelity of the fragrance profile, preferably the fragrance component derived from the volatile fragrance materials, such that it remains significantly the same from initial impression to the end as compared to a control composition in the absence of the substantially non-odorous fragrance modulators or having the traditional high levels of the low volatile fragrance materials. While not wishing to be bound by theory, it is believed that the substantially non-odorous fragrance modulators associate to the fragrance materials and retard evaporation. This may be due to a combination of both the functionality and the structure of the modulators and the perfume materials.

In another aspect, the present invention is directed to a modulator for fragrance materials comprising sucrose laurate, sucrose myristate, sucrose palmitate, sucrose stearate and mixtures thereof. Preferably, the fragrance material is a volatile fragrance material having a vapor pressure greater than or equal to 0.001 Torr (0.000133 kPa) at 25° C. In yet another aspect, the present invention is directed to a composition comprising a fragrance component and a modulator, wherein the modulator is sucrose laurate, sucrose myristate, sucrose palmitate, sucrose stearate and mixtures thereof.

Test Methods

The following assays set forth must be used in order that the invention described and claimed herein may be more fully understood.

Test Method 1: Determining Vapor Pressure

In order to determine the vapor pressure for the fragrance materials, follow these SciFinder steps to acquire the vapor pressure.

1. Input the CAS registry number for the particular fragrance material.
2. Select the vapor pressure from the search results.
3. Record the vapor pressure (given in Torr at 25° C.).

SciFinder uses Advanced Chemistry Development ((ACD/Labs) Software Version 14.02). If the CAS number for the particular fragrance material is unknown or does not exist, you can utilize the ACD/Labs reference program to directly determine the vapor pressure. Vapor Pressure is expressed in 1 Torr, which is equal to 0.133 kilopascal (kPa).

Test Method 2: Olfactory Tests

In order to show the effect of the substantially non-odorous fragrance modulators and low levels of the low volatile fragrance materials on the perception of fragrance profile in a composition of the present invention, test compositions are made, as described in the Example section, and given to panelists to evaluate.

At the testing facility, 50 µL samples of the compositions and the controls are applied to glass slides and placed on a hot plate at 32° C. to represent skin temperature for varying durations. It is important that glass slides of samples that are to be later compared are prepared at the same time. The panelists are asked to evaluate the perceived fragrance profile (intensity and/or character) of each glass slide sample at a given time point. Slides are presented coded so that their identity is not known by the panelists. Within a given time point panelists evaluate the slides in a random order and are able to revisit their assessment as they work through the slides at that time point. Their assessments are recorded. In the subsequent analysis, the data for strength and character comparisons are drawn from the independent assessments carried out at a given time point. Only when using the character difference scale below are any 2 products physically directly compared to each other. Panelists are selected from individuals who are either trained to evaluate fragrances according to the scales below or who have experience with fragrance evaluation in the industry. Typically, around 6 to 10 panellists are used to evaluate a given product and its control.

(a) Fragrance Intensity:

The panelists are asked to give a score on a scale of 0 to 5 for perceived fragrance intensity according to the odour intensity scale set out in Table 4 herein below.

TABLE 4

Odour Intensity Scale

| Score | Fragrance Intensity |
|---|---|
| 0 | None |
| 1 | Very Weak |
| 2 | Weak |
| 3 | Moderate |
| 4 | Strong |
| 5 | Very Strong |

(b) Fragrance Character:

The panelists are asked to assess the fragrance character in one of 2 ways:
i) a score on a scale of 0 to 3 for the dominance of particular characters that are relevant to that particular fragrance, e.g.: fresh, green, watery, floral, rose, muguet, fruity, apple, berry, citrus, creamy, woody, balsamic, amber, musk just to name a few, according to the odour grading scale set out in Table 5(i) herein below;
ii) a score on a scale of 1 to 5 for changes in the perceived fragrance profile change for the test compositions versus the controls according to the odour grading scale set out in Table 5(ii) herein below.

TABLE 5(i)

Character Dominance Odour Grading Scale

| Score | Fragrance Character Dominance |
|---|---|
| 0 | Not noticeable |
| 1 | Slight presence of the character |
| 2 | Moderate presence of the character |
| 3 | Dominance of the character |

TABLE 5(ii)

Character Difference Odour Grading Scale

| Score | Fragrance Character Change |
|---|---|
| 1 | Perfume character is unchanged, i.e., no difference between the sample vs. the control. |
| 2 | Slight perfume character change when compared directly with the control. |
| 3 | Moderate perfume change but similar character to the control, |
| 4 | Large difference in perfume character from the control. |
| 5 | Total difference in the perfume character from the control. |

The results of the panelists are averaged and then analysed using Analysis of Variance methods. The model treats the subject as a random effect and looks at the impact of product, time and the interaction between product and time. From the analysis the least square means for the product and time interaction are obtained. These means (as well as their confidence intervals) are then plotted to enable comparisons between products at each time point. It should be noted that the confidence levels plotted are intended as a guide, and not as a statistical comparison, as they do not take into account that multiple testing has been performed. As well as a graphical assessment, statistical comparisons between the two products at each of the time points are performed with a Tukey correction for multiple comparisons. The p-values for the product differences were obtained, with p-values<0.05 indicating a statistical difference between the two products at 5% significance (or 95% confidence).

Test Method 3: Analytical Evaporation Tests

The following test is carried out to demonstrate the improved or enhanced longevity of a fragrance profile of a composition of the present invention vs. a control. In particular, the test measures the effect of a substantially non-odorous fragrance modulator on the evaporation rate of one or more fragrance materials (e.g., 10 PRMs) formulated in a composition. The evaporation response of the fragrance materials to the modulator, as a function of time, is measured through the use of gas chromatography ("GC").

1. A test composition may comprise a substantially non-odorous fragrance modulator (as disclosed in Table 3) with either: (i) a volatile fragrance material (any one of the fragrance materials as disclosed in Table 2), or (ii) a blend of volatile fragrance materials from Table 2 (as disclosed as Fragrance Example 6 in Table 11). The test compositions may also contain high purity ethanol, such as Hayman 100% EP/BP grade, and deionized water. Samples test compositions are provided in Tables 18(b) and 18(c). All of the ingredients are admixed until evenly distributed in the test compositions.

2. A control composition to the test composition described in 1 above, without the substantially non-odorous fragrance modulator, is made in a similar manner to Step 1, except that the missing substantially non-odorous modulator is replaced by deionized water. Sample control compositions are provided in Tables 18(b) and 18(c).

3. An internal standard is needed to correct for variations of the amount of composition dispensed in the evaporation test as well as loss during the GC analysis. The internal standard has a vapor pressure of less than 0.001 Torr (0.000133 kPa) at 25° C. and is soluble in the composition and fragrance material. A suitable non-limiting example of an internal standard is triethyl citrate. The internal standard and fragrance material are admixed until evenly distributed at a level of 90 to 95 parts by weight of fragrance material and the required amount of internal standard to reach 100 parts. This mixture is then use to prepare the sample compositions in Step 1 and 2. Alternatively, the internal standard and test or control composition are admixed until evenly distributed at a level of 99 to 99.75 parts by weight of composition and the required amount of internal standard to reach 100 parts. This resultant solution is used in subsequent steps.

4. A hotplate is set to a temperature of 32° C. An aluminum container, such as TA Instruments T-Zero™ pan, is placed on the hotplate. 20 µL of the test or control composition is introduced in the aluminum container using a micropipette. Alternatively, the aluminum container may be filled with the test or control composition to its full capacity. The time at which this takes place is determined to be time zero (i.e., T=0). Multiple aluminum containers are prepared and left at the set temperature for pre-determined periods of time, such as for example 30 mins, 1 hr, 2 hrs, 3 hrs, 4 hrs, 5 hrs, 6 hrs, 8 hrs and up to 12 hrs.

5. The aluminum container is removed from the hotplate at the end of the pre-determined time period and transferred by being inserted into a 4 mL glass vial already containing at least 2 mL of highly volatile solvent, such as high purity ethanol or hexane.

6. The glass vial is mixed using a Heidolph multi REAX shaker, or equivalent, for 5 to 10 mins to extract the fragrance materials into the solvent phase. 1.5 mL of the resultant solution is transferred to a 2 mL GC vial.

7. The GC vial is analysed on an Agilent GC system 6890 equipped with an autosampler, or equivalent. A GC column such as a DB-5MS, Rxi-5 SilMS model or equivalent phase, with a length of 30 m, an inner diameter of 0.25 mm and a film thickness of 1 µm is used. The GC parameters are set to the values indicated as follows:

TABLE 5(iii)

| GC Parameters | |
|---|---|
| Injector temperature: | 270° C. |
| Initial gas velocity: | 25 to 40 cm/sec (for Helium as the carrier gas) |
| Initial oven temperature: | 50° C. |
| Temperature ramp: | 8° C./min |
| Final oven temperature: | 310° C. |

Gas chromatography with flame ionization detection ("FID") or with mass spectrometry ("MS") can be used for the identification and quantification of fragrance material in the compositions. Either detection system can be used in conjunction with GC. The column dimensions as well as GC settings described in this method, such as injector temperature, carrier gas velocity, temperature ramp and final oven temperature can be adjusted to optimize the response of the fragrance material and internal standard being monitored. The detection system settings, such as FID gas flows and temperature or MS parameters, should be optimized by a trained analyst to enable the precise detection and quantification of the analytes of interest.

8. The peak area of the fragrance material and internal standard are recorded. The peak area ratio of the fragrance material and the internal standard is calculated at each time point for each sample composition. The % of non-evaporated fragrance material remaining from T=0 is calculated at each time point for each sample composition. The % fragrance material remaining in each composition is plotted to give an evaporation profile over time. This is done for both the test and control compositions.

Significance is determined by comparison of the evaporation profile for the same fragrance material or same fragrance mixture in the test and control compositions.

Test Method 4: Analytical Headspace Tests

The following test is carried out to demonstrate the character retention over time of a fragrance composition of the present invention vs. a control. It is necessary for the test and control samples to be run at approximately the same time to ensure that ambient conditions are the same. The test measures the presence of one or more fragrance materials in the headspace formed in a sealed vial by the test composition, after set evaporation times. The fragrance profile in the headspace is measured at specific time points through the use of headspace ("HS") gas chromatography ("GC").

1. The test and control compositions as described in the Example section are used for the evaluation.
2. Capillaries of about 2 cm to 3.5 cm, with one sealed end are cut from a Sigma Aldrich "Stuart™ melting point tube" product code Z673269, or equivalent. A suitable fixed volume chosen between 50 and 200 µL of the composition is pipetted into the well of a VWR Tissue Culture 96 F well plate, or equivalent. The sealed end of the glass capillary is dipped into the filled well and left for at least 15 secs to wet the surface of the glass. Care must be taken not to contact the glass capillary with the sides of the well by maintaining it straight and approximately in the center of the well.
3. The glass capillary is then removed from the well and inverted or transferred onto a stable surface or into a holder and allowed to evaporate at ambient conditions for a set period of time. A windshield may be used to reduce high air turbulence.
4. The glass capillary is then introduced into an empty 20 mL HS vial, which is immediately closed with a PTFE cap. The time at which this takes place is determined to be time T=initial (i.e., T=10 mins).
5. Multiple glass capillaries are prepared in the same way and left to evaporate at ambient temperature for pre-determined periods of time, such as for example 10, 15, 30 mins, 1 hr, 2 hrs, 3 hrs, 4 hrs, 5 hrs, and up to 6 hrs, before being introduced to the headspace vial and sealed.
6. The HS vial is then analysed on an Agilent GC system 6890 equipped with a Gerstel MPS 2 autosampler, or equivalent, capable of performing SPME injections. A SPME fiber assembly DVB/CAR/PDMS (50/30 µm, 1 cm length) is required. A GC column such as a DB-5MS, ZB-5MSi models, or equivalent phase, with a length of 30 m, an inner diameter of 0.25 mm and a film thickness of 1 µm is used.

7. The SPME HS parameters are set to the values indicated as follows:

TABLE 5(iv)

| SPME Parameters | |
|---|---|
| Incubation chamber temperature: | 40° C. |
| Incubation time: | 20 mins |
| Agitation of sample | 250 RPM |
| Extraction time | 5 mins |
| Desorption time | 2 mins |

8. The GC parameters are set to the values indicated as follows:

TABLE 5(v)

| GC Parameters | |
|---|---|
| Injector temperature: | 270° C. |
| Initial gas velocity: | 20 to 40 cm/sec (for Helium as the carrier gas) |
| Initial oven temperature: | 45° C. with 2 mins Hold Time |
| Temperature ramp 1: | 30° C./min |
| Temperature 1: | 80° C. |
| Temperature ramp 2: | 8° C./min |
| Final temperature: | 300° C. |

Gas chromatography with flame ionization detection ("FID") or with mass spectrometry ("MS") can be used for the identification and quantification of fragrance material in the compositions. Either detection system can be used in conjunction with GC. The column dimensions as well as GC settings described in this method, such as injector temperature, carrier gas velocity, temperature ramp and final oven temperature can be adjusted to optimize the response of the fragrance material being monitored. The detection system settings, such as FID gas flows and temperature or MS parameters, should be optimized by a trained analyst to enable the precise detection and identification of the analytes of interest.

9. A qualitative assessment of the chromatograms obtained is performed by comparing the peak height of the fragrance materials and overall chromatogram at time T=10 mins to other time points. A dotted line is drawn around an estimated retention time where fragrance materials with a vapour pressure of 0.001 Torr or less (0.000133 kPa or less) elute during the analysis. The difference between the peaks present at each measured time point for the test and control compositions provides evidence of the retention of the character of the fragrance over time.

10. This test set-up is designed to enable the collection of the headspace in a manner that does not saturate the SPME fiber. If the fiber is saturated it does not provide an accurate analysis of the headspace composition. Therefore the quantity of liquid and the evaporation surface area are very different from those in the olfactive evaluation of the same samples. For this reason it is not possible to compare directly the evaporation time frames used in the 2 experiments. It is expected that the evaporation profile is much faster in this headspace experiments compared to the olfactive evaluations.

EXAMPLES

The following examples are provided to further illustrate the present invention and are not to be construed as limitations of the present invention, as many variations of the present invention are possible without departing from its spirit or scope.

Example 1—Fragrance Oils

Fragrance examples 1, 2, 3, 4b and 5b are provided below in Tables 6, 7, 8, 9 and 10, respectively, as non-limiting examples of formulations of fragrance materials intended to form the fragrance component of the compositions of the present invention. The exemplary formulations of the fragrance materials span the range from "simple accords" (less than 10 fragrance materials) to "complex fragrances" (greater than 30 fragrance materials). Typically, full bodied fragrance compositions do not comprise less than about 30 fragrance materials.

Fragrance examples 4a and 5a provided in Table 9 and 10, respectively, below are examples of traditional formulations of fragrance materials that fall outside the scope of the present invention.

Fragrance example 6 provided in Table 11 below as an example of a formulation of 10 volatile fragrance materials.

Fragrance examples 7 and 8 are provided in Tables 12 and 13 below as examples of a formulation of fragrance materials intended to form the fragrance component that fall outside the scope of the present invention.

Fragrance examples 9 to 16 are provided in Tables 14 and 15 below as examples of formulations of fragrance materials containing higher than 30 wt % of the low volatile fragrance materials.

Fragrance examples 17 and 18 are provided in Tables 16 and 17 below as comparative samples of formulations of fragrance materials intended to form the fragrance component.

The following fragrance formulations are made by mixing the listed ingredients in the listed proportions (wt %) at room temperature, wherein the wt % is relative to the total weight of the fragrance component.

TABLE 6

Fragrance Example 1 (Fresh Floral Accord - 10 wt % of Low Volatile Fragrance Materials)

| Ingredients | CAS Number | Vapor Pressure (Torr at 25° C.) | Parts (wt %) |
|---|---|---|---|
| Benzyl acetate | 140-11-4 | 0.1640 | 10.8 |
| Linalool | 78-70-6 | 0.0905 | 9.8 |
| Phenethyl alcohol | 60-12-8 | 0.0741 | 15.7 |
| Indole | 120-72-9 | 0.0298 | 1.0 |
| α-Terpineol | 98-55-5 | 0.0283 | 2.9 |
| Geranyl acetate | 105-87-3 | 0.0256 | 4.9 |
| Cymal | 103-95-7 | 0.00881 | 5.9 |
| Hydroxycitronellal | 107-75-5 | 0.00318 | 22.4 |
| Majantol ® | 103694-68-4 | 0.00224 | 16.6 |
| Hexyl cinnamic aldehyde | 101-86-0 | 0.000697 | 10.0 |
| | | Total | 100.00 |

TABLE 7

Fragrance Example 2 (Fresh Male Accord - 13.51 wt % of Low Volatile Fragrance Materials)

| Ingredients | CAS Number | Vapor Pressure (Torr at 25° C.) | Parts (wt %) |
|---|---|---|---|
| d-Limonene | 5989-27-5 | 1.540000 | 10.0 |
| Dihydromyrcenol | 18479-58-8 | 0.166000 | 10.0 |
| Boisiris | 68845-00-1 | 0.013500 | 6.5 |
| Canthoxal | 5462-06-6 | 0.010200 | 8.0 |
| Helional | 1205-17-0 | 0.002700 | 10.0 |
| Kephalis | 36306-87-3 | 0.002690 | 20.0 |
| Majantol ® | 103694-68-4 | 0.002240 | 15.5 |
| Javanol ® | 198404-98-7 | 0.000902 | 5.0 |
| Galaxolide ®* | 1222-05-5 | 0.000414 | 7.5 |
| Isopropyl Myristate | 110-27-0 | — | 7.5 |
| | | Total | 100.00 |

*Supplied at 50% in Isopropyl myristate.

TABLE 8

Fragrance Example 3 (Sweet Dream 18 Fragrance - 11.15 wt % of Low Volatile Fragrance Materials)

| Ingredients | CAS Number | Vapor Pressure (Torr at 25° C.) | Parts (wt %) |
|---|---|---|---|
| Prenyl acetate | 1191-16-8 | 3.99000000 | 0.100 |
| Manzanate | 39255-32-8 | 2.91000000 | 0.200 |
| Hexyl acetate | 142-92-7 | 1.39000000 | 0.700 |
| cis-3-Hexenyl acetate | 3681-71-8 | 1.22000000 | 0.200 |
| Benzaldehyde | 100-52-7 | 0.97400000 | 0.200 |
| Liffarome | 67633-96-9 | 0.72100000 | 0.150 |
| Hexyl isobutyrate | 2349-07-7 | 0.41300000 | 0.055 |
| Dihydromyrcenol | 18479-58-8 | 0.16600000 | 2.500 |
| Benzyl acetate | 140-11-4 | 0.16400000 | 0.700 |
| Linalyl acetate | 115-95-7 | 0.11600000 | 2.500 |
| Verdox | 88-41-5 | 0.10300000 | 4.000 |
| Phenethyl alcohol | 60-12-8 | 0.07410000 | 8.000 |
| Rossitol | 215231-33-7 | 0.02990000 | 1.500 |
| alpha-Terpineol | 98-55-5 | 0.02830000 | 1.500 |
| Geranyl acetate | 105-87-3 | 0.02560000 | 1.500 |
| Rhodinol | 141-25-3 | 0.01970000 | 0.700 |
| Givescone | 57934-97-1 | 0.01710000 | 0.700 |
| Methyl anthranilate | 134-20-3 | 0.01580000 | 0.050 |
| Ysamber K | 154171-77-4 | 0.01470000 | 1.000 |
| alpha-Ionone | 127-41-3 | 0.01440000 | 3.000 |
| Citronellyl acetate | 150-84-5 | 0.01370000 | 0.500 |
| cis-3-hexenyl-cis-3-hexenoate | 61444-38-0 | 0.01220000 | 0.200 |
| Cinnamic alcohol | 104-54-1 | 0.01170000 | 0.100 |
| delta-damascone | 57378-68-4 | 0.01020000 | 0.200 |
| Citronellyl-oxyacetaldehyde | 7492-67-3 | 0.00967000 | 0.100 |
| Cymal | 103-95-7 | 0.00881000 | 0.500 |
| Floralozone | 67634-15-5 | 0.00808000 | 0.100 |
| Ethylmethyl-phenylglycidate | 77-83-8 | 0.00571000 | 0.200 |
| Florosa Q | 63500-71-0 | 0.00557000 | 3.000 |
| Ethyl linalool | 10339-55-6 | 0.00520000 | 6.400 |
| Pivarose | 67662-96-8 | 0.00484000 | 2.500 |
| Hydroxycitronellal | 107-75-5 | 0.00318000 | 7.500 |
| Methyl Ionone | 7779-30-8 | 0.00286000 | 4.000 |
| gamma-Undecalactone | 104-67-6 | 0.00271000 | 0.500 |
| Kephalis | 36306-87-3 | 0.00269000 | 5.000 |
| Cashmeran | 33704-61-9 | 0.00269000 | 1.000 |
| Magnolan | 27606-09-3 | 0.00251000 | 3.000 |
| Majantol ® | 103694-68-4 | 0.00224000 | 6.900 |
| Brahmanol | 72089-08-8 | 0.00154000 | 3.000 |
| Coumarin | 91-64-5 | 0.00130000 | 0.500 |
| Glycolierral | 68901-32-6 | 0.00121000 | 0.100 |
| Raspberry ketone | 5471-51-2 | 0.00106000 | 0.100 |
| Top Mango base [3] | — | — | 0.500 |
| Cherry base [3] | — | — | 0.200 |
| Cassis base [3] | — | — | 0.300 |
| Bergamot Oil [4] | — | — | 6.000 |
| *Prunella* base [3] | — | — | 0.500 |
| Hexyl cinnamic aldehyde | 101-86-0 | 0.00069700 | 1.500 |
| Sandalore | 65113-99-7 | 0.00062500 | 3.000 |
| Dupical | 30168-23-1 | 0.00044100 | 0.005 |
| Galaxolide ® [1] | 1222-05-5 | 0.00041400 | 1.500 |
| Ebanol | 67801-20-1 | 0.00028100 | 2.000 |
| Helvetolide | 141773-73-1 | 0.00005790 | 2.000 |
| Warm Milk base [5] | — | — | 0.200 |
| Vanilla Absolute [2,6] | — | — | 0.100 |
| Isopropyl Myristate | — | — | 1.500 |
| Dipropylene Glycol | — | — | 6.040 |
| | | Total | 100.00 |

[1] Supplied at 50% in IPM.
[2] Supplied at 50% in DiPG.
[3] Proprietary bases that contain a mixture of perfume raw materials, judged to be of high volatility for the purposes of calculating % of low volatility PRMs.
[4] Natural oils or extracts that contain a mixture of perfume raw materials, judged to be of high volatility for the purposes of calculating % of low volatility PRMs.
[5] Proprietary bases that contain a mixture of perfume raw materials, judged to be of low volatility for the purposes of calculating % of low volatility PRMs.
[6] Natural oils or extracts that contain a mixture of perfume raw materials, judged to be of low volatility for the purposes of calculating % of low volatility PRMs.

TABLE 9

Fragrance Examples 4a and 4b ("Traditional Floral *Magnifica*" Example 4a - 37 wt % of Low Volatile Fragrance Materials and "Reduced Low Volatiles Floral *Magnifica*" Example 4b - 13 wt % of Low Volatile Fragrance Materials)

| | | | Parts (wt %) | |
|---|---|---|---|---|
| Ingredients | CAS Number | Vapor Pressure (Torr at 25° C.) | Example 4a (Traditional) | Example 4b (Reduced Low Volatiles) |
| Beta Gamma Hexenol | 928-96-1 | 2.126000 | 0.20 | 0.20 |
| Cis 3 Hexenyl Acetate | 3681-71-8 | 1.219000 | 0.30 | 0.30 |
| Benzyl Acetate | 140-11-4 | 0.16400000 | 3.01 | 3.01 |
| Liffarome | 67633-96-9 | 0.721000 | 0.20 | 0.20 |
| Ligustral Or Triplal | 68039-49-6 | 0.578000 | 0.10 | 0.10 |
| Methyl Pamplemousse | 67674-46-8 | 0.214000 | 0.40 | 0.40 |
| d-Limonene | 5989-27-5 | 1.54000000 | 3.01 | 3.01 |
| Phenyl Acetaldehyde [1] | 122-78-1 | 0.368000 | 0.0002 | 0.0002 |
| Precyclemone B | 52475-86-2 | 0.003810 | 0.20 | 0.20 |
| Ethyl 2 4-Decadienoate | 3025-30-7 | 0.009540 | 0.20 | 0.20 |
| Ambronat | 6790-58-5 | 0.009340 | 2.00 | 2.01 |
| Alpha Damascone | 24720-09-0 | 0.008300 | 0.04 | 0.06 |
| Citronellol | 106-22-9 | 0.032900 | 4.01 | 4.01 |
| Cyclemax | 7775-00-0 | 0.018200 | 0.40 | 0.40 |
| Cyclo Galbanate | 68901-15-5 | 0.003230 | 0.10 | 0.10 |
| Cymal | 103-95-7 | 0.008810 | 0.90 | 1.51 |
| Dimethyl Benzyl Carbinyl Butyrate | 10094-34-5 | 0.001680 | 0.50 | 0.50 |
| Ethyl Linalool | 10339-55-6 | 0.005200 | 7.23 | 12.04 |

TABLE 9-continued

Fragrance Examples 4a and 4b ("Traditional Floral *Magnifica*" Example 4a - 37 wt % of Low Volatile Fragrance Materials and "Reduced Low Volatiles Floral *Magnifica*" Example 4b - 13 wt % of Low Volatile Fragrance Materials)

| Ingredients | CAS Number | Vapor Pressure (Torr at 25° C.) | Example 4a (Traditional) Parts (wt %) | Example 4b (Reduced Low Volatiles) Parts (wt %) |
|---|---|---|---|---|
| Florosa Q | 63500-71-0 | 0.005570 | 6.43 | 10.71 |
| Gamma Decalactone | 706-14-9 | 0.008520 | 0.20 | 0.20 |
| Geraniol | 106-24-1 | 0.013300 | 3.01 | 5.02 |
| Geranyl Acetate | 105-87-3 | 0.009760 | 2.01 | 2.01 |
| Helional | 1205-17-0 | 0.002700 | 2.41 | 4.01 |
| Heliotropin | 120-57-0 | 0.010400 | 0.20 | 0.20 |
| Hivernal | 173445-65-3 | 0.00392000 | 0.20 | 0.20 |
| Hydroxy-citronellal | 107-75-5 | 0.003180 | 2.41 | 4.01 |
| Ionone Beta | 14901-07-6 | 0.003080 | 0.24 | 0.40 |
| Ionone Gamma Methyl | 127-51-5 | 0.002820 | 1.81 | 3.01 |
| Jasmal | 18871-14-2 | 0.004340 | 5.02 | 5.02 |
| Jasmolactone | 32764-98-0 | 0.003550 | 0.20 | 0.20 |
| Linalyl Propionate | 144-39-8 | 0.026300 | 1.20 | 1.20 |
| Magnolan 690304 | 27606-09-3 | 0.002510 | 3.01 | 5.02 |
| Majantol ® | 103694-68-4 | 0.002240 | 2.41 | 4.01 |
| Phenyl Ethyl Alcohol | 60-12-8 | 0.074100 | 3.01 | 5.02 |
| Phenyl Hexanol | 55066-48-3 | 0.006370 | 3.61 | 6.02 |
| Undecavertol | 81782-77-6 | 0.010700 | 2.01 | 2.01 |
| Vanillin | 121-33-5 | 0.001940 | 0.10 | 0.10 |
| cis-3-Hexenyl cis-3-Hexenoate | 61444-38-0 | 0.012200 | 0.10 | 0.10 |
| Phenoxy Ethyl Iso Butyrate | 103-60-6 | 0.005620 | 0.50 | 0.50 |
| 5-Cyclohexadecen-1-One | 37609-25-9 | 0.000033 | 1.00 | 1.00 |
| Ambrettolide | 28645-51-4 | 0.000001 | 1.00 | 1.00 |
| Cis-3-Hexenyl Salicylate | 65405-77-8 | 0.000246 | 1.51 | 0.50 |
| Delta Muscenone 962191 | 63314-79-4 | 0.000165 | 1.00 | 1.00 |
| Hedione ® HC | 24851-98-7 | 0.000710 | 10.54 | 3.51 |
| Iso-E Super ® | 54464-57-2 | 0.000538 | 10.54 | 3.51 |
| Para Hydroxy Phenyl Butanone | 5471-51-2 | 0.001060 | 0.20 | 0.20 |
| Polysantol | 107898-54-4 | 0.000117 | 0.50 | 0.50 |
| | | Total | 100 | 100 |

[1] supplied as 1% in DPG.

TABLE 10

Fragrance Examples 5a and 5b ("Traditional Muguesia *Magnifica*" Example 5a - 37 wt % of Low Volatile Fragrance Materials and "Reduced Low Volatiles Muguesia *Magnifica*" Example 5b - 13 wt % of Low Volatile Fragrance Materials)

| Ingredients | CAS Number | Vapor Pressure (Torr at 25° C.) | Example 5a (Traditional) Parts (wt %) | Example 5b (Reduced Low Volatiles) Parts (wt %) |
|---|---|---|---|---|
| Benzyl Alcohol | 100-51-6 | 0.158000 | 0.10 | 0.10 |
| Methyl Phenyl Carbinyl Acetate | 93-92-5 | 0.203000 | 0.32 | 0.40 |
| d-limonene | 5989-27-5 | 1.54000000 | 1.00 | 1.00 |
| Benzyl Acetate | 140-11-4 | 0.16400000 | 5.86 | 7.32 |
| Beta Gamma Hexenol | 928-96-1 | 2.126000 | 0.40 | 0.40 |
| Cis 3 Hexenyl Acetate | 3681-71-8 | 1.219000 | 0.20 | 0.20 |
| Linalyl Acetate | 115-95-7 | 0.077400 | 1.00 | 1.00 |
| Jasmal | 18871-14-2 | 0.004340 | 3.21 | 4.01 |
| Indol | 120-72-9 | 0.029800 | 0.10 | 0.10 |
| Hydroxy-citronellal | 107-75-5 | 0.003180 | 3.21 | 4.01 |
| Helional | 1205-17-0 | 0.002700 | 4.01 | 5.02 |
| Geranyl Acetate | 105-87-3 | 0.009760 | 3.21 | 4.01 |
| Geraniol | 106-24-1 | 0.013300 | 4.01 | 5.02 |
| Florosa Q | 63500-71-0 | 0.005570 | 0 | 9.03 |
| Cinnamic Alcohol | 104-54-1 | 0.005720 | 0.20 | 0.20 |
| Cinnamic Aldehyde | 104-55-2 | 0.02650000 | 0.06 | 0.06 |
| Cis Jasmone | 488-10-8 | 0.020100 | 0.50 | 0.50 |
| Citronellol | 106-22-9 | 0.032900 | 4.01 | 5.01 |
| Citronellyl Acetate | 150-84-5 | 0.013700 | 3.21 | 4.01 |
| Citronellyl Oxyacetaldehyde | 7492-67-3 | 0.009670 | 0.10 | 0.10 |
| Cyclemax | 7775-00-0 | 0.018200 | 0.32 | 0.40 |
| Cyclo Galbanate | 68901-15-5 | 0.003230 | 0.20 | 0.20 |
| Cymal | 103-95-7 | 0.008810 | 1.61 | 2.01 |
| Ethyl Linalool | 10339-55-6 | 0.005200 | 8.04 | 10.03 |
| Florhydral | 125109-85-5 | 0.020700 | 0.16 | 0.20 |
| Majantol ® | 103694-68-4 | 0.002240 | 3.21 | 4.01 |
| Phenyl Ethyl Acetate | 103-45-7 | 0.056400 | 0.40 | 0.40 |
| Phenyl Ethyl Alcohol | 60-12-8 | 0.074100 | 14.45 | 18.06 |
| Ambrettolide | 28645-51-4 | 0.000001 | 1.00 | 1.00 |
| Cis-3-Hexenyl Salicylate | 65405-77-8 | 0.000246 | 1.00 | 0.50 |
| Benzyl Salicylate | 118-58-1 | 0.00017500 | 16.61 | 2.51 |
| Hedione ® HC | 24851-98-7 | 0.000710 | 8.03 | 4.01 |
| Iso-E Super ® | 54464-57-2 | 0.000538 | 10.03 | 5.02 |
| Phenyl Acetaldehyde Dimethyl Acetal | 101-48-4 | 0.55600000 | 0.20 | 0.10 |
| Total | | | 100 | 100 |

TABLE 11

Fragrance Example 6 (10 Volatile Fragrance Materials)

| Ingredients | CAS Number | Vapor Pressure (Torr at 25° C.) | Parts (wt %) |
|---|---|---|---|
| Tetra-Hydro Linalool | 78-69-3 | 0.115 | 9.85 |
| Terpinyl acetate | 80-26-2 | 0.0392 | 12.21 |
| Dimethyl Benzyl Carbinyl Acetate | 151-05-3 | 0.0139 | 11.96 |
| Dimethyl Benzyl Carbinol | 100-86-7 | 0.088844 | 9.35 |
| Phenyl Ethyl alcohol | 60-12-8 | 0.074100 | 7.60 |
| Laevo Carvone | 6485-40-1 | 0.0656 | 9.35 |
| Indole | 120-72-9 | 0.0298 | 7.29 |

TABLE 11-continued

Fragrance Example 6 (10 Volatile Fragrance Materials)

| Ingredients | CAS Number | Vapor Pressure (Torr at 25° C.) | Parts (wt %) |
|---|---|---|---|
| Ethyl Safranate | 35044-59-8 | 0.0266 | 12.09 |
| Indocolore | 2206-94-2 | 0.0255 | 10.09 |
| Eugenol | 97-53-0 | 0.0104 | 10.21 |
| | | Total | 100.00 |

TABLE 12

Fragrance Example 7 (Fresh Floral GF 6-7 Accord - 40.14 wt % of Low Volatile Fragrance Materials)

| Ingredients | CAS Number | Vapor Pressure (Torr at 25° C.) | Parts (wt %) |
|---|---|---|---|
| Ligustral or Triplal | 68039-49-6 | 0.578000 | 0.15 |
| Benzyl acetate | 140-11-4 | 0.164000 | 0.31 |
| Verdox | 88-41-5 | 0.103000 | 5.38 |
| Phenethyl alcohol | 60-12-8 | 0.074100 | 1.54 |
| Indole | 120-72-9 | 0.029800 | 0.02 |
| Heliotropin | 120-57-0 | 0.010400 | 1.23 |
| gamma-Decalactone | 706-14-9 | 0.008520 | 0.38 |
| Florosa Q | 63500-71-0 | 0.005570 | 15.38 |
| Ethyl linalool | 10339-55-6 | 0.005200 | 26.15 |
| Isoeugenol | 97-54-1 | 0.005190 | 0.08 |
| alpha-Irone | 79-69-6 | 0.004190 | 1.54 |
| Vanillin | 121-33-5 | 0.001940 | 6.15 |
| Dimethyl benzyl carbinyl butyrate | 10094-34-5 | 0.001680 | 1.54 |
| Methyl beta-naphthyl ketone | 93-08-3 | 0.000957 | 0.77 |
| Methyl dihydrojasmonate | 24851-98-7 | 0.000710 | 30.60 |
| Benzyl salicylate | 118-58-1 | 0.000175 | 7.69 |
| Polysantol | 107898-54-4 | 0.000117 | 0.77 |
| Lrg 201 | 4707-47-5 | 0.000029 | 0.31 |
| | | Total | 100.00 |

TABLE 13

Fragrance Example 8 (Traditional Floral Accord - 54.00 wt % of Low Volatile Fragrance Materials)

| Ingredients | CAS Number | Vapor Pressure (Torr at 25° C.) | Parts (wt %) |
|---|---|---|---|
| Benzyl acetate | 140-11-4 | 0.1640 | 5.5 |
| Linalool | 78-70-6 | 0.0905 | 5.0 |
| Phenethyl alcohol | 60-12-8 | 0.0741 | 8.0 |
| Indole | 120-72-9 | 0.0298 | 0.5 |
| α-Terpineol | 98-55-5 | 0.0283 | 1.5 |
| Geranyl acetate | 105-87-3 | 0.0256 | 2.5 |
| Cymal | 103-95-7 | 0.00881 | 3.0 |
| Hydroxycitronellal | 107-75-5 | 0.00318 | 11.5 |
| Majantol ® | 103694-68-4 | 0.00224 | 8.5 |
| Hexyl cinnamic aldehyde | 101-86-0 | 0.000697 | 4.0 |
| iso gamma super | 68155-66-8 | 0.000565 | 12.50 |
| Sandalore | 65113-99-7 | 0.000625 | 18.75 |
| Habanolide | 111879-80-2 | 0.00000431 | 18.75 |
| | | Total | 100.00 |

TABLE 14

Fragrance Examples 9, 10, 11 and 12 (Traditional Flora *Magnifica* - Greater than 30 wt % of Low Volatile Fragrance Materials)

| Ingredients | Fragrance Example 9 Weight % | Fragrance Example 10 Weight % | Fragrance Example 11 Weight % | Fragrance Example 12 Weight % |
|---|---|---|---|---|
| Flora Magnifica [1] | 86.96 | 83.33 | 74.07 | 68.97 |
| Ethylene Brassylate | 4.35 | 4.167 | 3.704 | 6.90 |
| Methyl Dihydro Jasmonate | 4.35 | 8.33 | 14.82 | 13.79 |
| Iso-E Super ® | 4.35 | 4.167 | 7.407 | 10.35 |
| Total | 100 | 100 | 100 | 100 |
| Wt % Low Volatile Fragrance Materials | 45 | 47 | 53 | 56 |

[1] Fragrance Example 4a.

TABLE 15

Fragrance Examples 13, 14, 15 and 16 (Traditional Muguesia *Magnifica* - Greater than 30 wt % of Low Volatile Fragrance Materials)

| Ingredients | Fragrance Example 13 Weight % | Fragrance Example 14 Weight % | Fragrance Example 15 Weight % | Fragrance Example 16 Weight % |
|---|---|---|---|---|
| Muguesia Magnifica [1] | 86.96 | 83.33 | 74.07 | 68.97 |
| Ethylene Brassylate | 4.35 | 4.17 | 3.70 | 6.90 |
| Methyl Dihydro Jasmonate | 4.35 | 8.33 | 14.82 | 13.79 |
| Iso-E Super ® | 4.35 | 4.17 | 7.41 | 10.35 |
| Total | 100 | 100 | 100 | 100 |
| Wt % Low Volatile Fragrance Materials | 45 | 47 | 53 | 56 |

[1] Fragrance Example 5a.

Fragrance example 17 (as disclosed in Table 16) is composed of 68.51 wt % volatile fragrance materials and 31.49 wt % of low volatile fragrance materials, wherein the wt % is relative to the total weight of the fragrance component.

TABLE 16

Fragrance Example 17 (Comparative Fragrance 1 - 31.49 wt % of Low Volatile Fragance Materials)

| Ingredients | CAS Number | Vapor Pressure (Torr at 25° C.) | Amount Parts by Weight | Parts (wt %) |
|---|---|---|---|---|
| Limonene | 5989-27-5 | 1.541 | 2576 | 30.04 |
| Cis-3-Hexenol | 928-96-1 | 1.039 | 21 | 0.24 |
| Zestover [6] | 78-70-6 | 0.578 | 1 | 0.01 |
| Linalol | 78-70-6 | 0.0905 | 553 | 6.45 |
| Aphermate [4] (10% DIPG) [7] | 25225-08-5 | 0.0678 | 7 | 0.08 |
| Cyclosal | 535-86-4 | 0.0311 | 35 | 0.41 |
| Coranol | 83926-73-2 | 0.0210 | 371 | 4.33 |
| Sclareolate ®* [1] | 319002-92-1 | 0.0196 | 630 | 7.35 |
| 3-Methoxy-7,7-dimethyl-10-methylene-bicyclo[4.3.1]decane | 216970-21-7 | 0.0196 | 371 | 4.33 |
| Cedramber [2] | 19870-74-8 | 0.0128 | 1050 | 12.24 |
| Ambrox ®* | 3738-00-9 | 0.00934 | 1 | 0.01 |
| Decal | 706-14-9 | 0.00852 | 21 | 0.24 |
| Damascone Alpha* (10% DIPG) [7] | 24720-09-0 | 0.00830 | 9.1 | 0.11 |
| (Methoxymethoxy)Cyclododecane | 42604-12-6 | 0.00686 | 182 | 2.12 |
| Lilial ® | 80-54-6 | 0.00444 | 26 | 0.30 |
| γ-Undecalactone* | 104-67-6 | 0.00271 | 21 | 0.24 |
| Calone ®* [3] | 28940-11-6 | 0.000831 | 50 | 0.58 |
| Paradisone ®[5]* | 24851-98-7 | 0.000710 | 1000 | 11.66 |
| Galaxolide ® (70% MIP Extra) [7] | 1222-05-5 | 0.000414 | 700 | 8.16 |
| Exaltenone | 14595-54-1 | 0.0000964 | 950 | 11.08 |
| | | Total | 8575.10 | 100 wt % |

*origin: Firmenich SA (Geneva, Switzerland).
[1] Propyl (5)-2-(1,1-dimethylpropxy)propanoate.
[2] 8-Methoxy-2,6,6,8-tetramethyl-tricyclo[5.3.1.0(1,5)]undecane.
[3] 7-Methyl-2H,4H-1,5-benzodioxepin-3-one.
[4] 1-(3,3-dimethyl-1-cyclohexyl)ethyl formate; origin: International Flavors & Fragrances.
[5] Methyl dihydrojasmonate.
[6] Linalool.
[7] Fragrance materials added as dilutions in a non-volatile solvent. For the purposes of calculating the fragrance oil composition actual fragrance materials levels added are used.

Fragrance example 18 (as disclosed in Table 17) is composed of 90.63 wt % of volatile fragrance materials and 9.37 wt % of low volatile fragrance materials, wherein the wt % is relative to the total weight of the fragrance component.

TABLE 17

Fragrance Example 18 (Comparative Fragrance 2 - 9.37 wt % of Low Volatile Fragance Materials)

| Ingredients | CAS Number | Vapor Pressure (Torr at 25° C.) | Amount Parts by Weight | Parts (wt %) |
|---|---|---|---|---|
| D-Limonene | 5989-27-5 | 1.540 | 50.00 | 5.21 |
| cis-3-Hexenol (10% in DPG) [4] | 928-96-1 | 1.040 | 0.5 | 0.05 |
| Acetophenone (10% in DPG) [4] | 98-86-2 | 0.299 | 1.00 | 0.10 |
| Methylphenyl Acetate | 101-41-7 | 0.176 | 10.00 | 1.04 |
| Dihydromyrcenol | 18479-58-8 | 0.166 | 50.00 | 5.21 |
| Benzyl acetate | 140-11-4 | 0.164 | 60.00 | 6.25 |
| Tetra-Hydro Linalool | n/a | 0.115 | 50.00 | 5.21 |
| n-Undecanal | n/a | 0.102 | 5.00 | 0.52 |
| Linalool | 78-70-6 | 0.0905 | 40.00 | 4.17 |
| Phenylethyl Alcohol | 60-12-8 | 0.0741 | 245.00 | 25.53 |
| Allyl amyl glycolate (10% in DPG) [4] | 67634-00-8 | 0.04000 | 2.00 | 0.21 |
| Indole (10% in DPG) [4] | 120-72-9 | 0.02980 | 1.00 | 0.10 |
| Alpha-Terpineol | 98-55-5 | 0.02830 | 30.00 | 3.13 |
| Diphenyl Oxide | 101-84-8 | 0.02230 | 5.00 | 0.52 |
| L-Citronellol | 7540-51-4 | 0.01830 | 80.00 | 8.34 |
| Beta-Ionone | 14901-07-6 | 0.01690 | 5.00 | 0.52 |
| Alpha-Ionone | 127-41-3 | 0.01440 | 15.00 | 1.56 |
| Dimethyl benzyl carbinyl acetate | 151-05-3 | 0.01390 | 30.00 | 3.13 |
| Geraniol | 106-24-1 | 0.01330 | 40.00 | 4.17 |
| Nerol | n/a | 0.01330 | 20.00 | 2.08 |
| Lilial ® [1] | 80-54-6 | 0.00444 | 60.00 | 6.25 |
| Gamma-Undecalactone | 104-67-6 | 0.00271 | 15.00 | 1.56 |
| Amyl salicylate | 2050-08-0 | 0.00144 | 25.00 | 2.61 |
| Galaxolide ® | 1222-05-5 | 0.000414 | 20.00 | 2.08 |
| cis-3-Hexenyl salicylate | 65405-77-8 | 0.000246 | 20.00 | 2.08 |
| Ethylene Brassylate | 105-95-3 | 0.00000000313 | 30.00 | 3.13 |
| Styrolyl Acetate [5] | — | — | 20.00 | 2.08 |
| Decenol trans-9 [3] | — | — | 15.00 | 1.56 |
| *Geranium* oil [2] | — | — | 15.00 | 1.56 |
| | | Total | 959.5 | 100 wt % |

[1] Benzenepropanal,4-(1,1-dimethylethyl)-α-methyl-.
[2] Natural oil that is judged to be volatile for the purposes of calculating levels of the volatile fragrance materials.
[3] Proprietary oil that is judged to be volatile for the purposes of calculating levels of the volatile fragrance materials.
[4] Fragrance materials added as dilutions in a non-volatilee solvent. For the purposes of calculating the fragrance oil composition actual fragrance materials levels added are used.
[5] Unknown oil that is judged to be of low volatility for the purposes of calculating levels of the volatile fragrance materials.

Example 2—Compositions Comprising Fragrance Oils and Substantially Non-Odorous Fragrance Modulators Compositions A, D, G, J and M are examples of fragrance compositions according to the present invention, made with any one of fragrance examples 1 to 3, 4b, 5b, and 18, respectively. Compositions B, E, H, K and N are compositions containing traditional or higher levels of low volatile fragrance materials, made with any of the fragrance examples 4a, 5a, and 7-17, respectively.

In parallel, control compositions C, F, I, L and O are prepared by replacing the different substantially non-odorous fragrance modulators by the same amount of deionized water. All of the compositions are prepared by admixture of the components described in Table 18(a), in the proportions indicated.

TABLE 18(a)

Fragrance Compositions

| Ingredients | Fragrance Composition (wt %) [1] | | | | | | | | | | | | | | |
|---|---|---|---|---|---|---|---|---|---|---|---|---|---|---|---|
| | A | B | C | D | E | F | G | H | I | J | K | L | M | N | O |
| Fragrance A1 [2] | 5-10 | — | — | 0.01-2 | — | — | 3-10 | — | — | 5-10 | — | — | 0.1-5 | — | — |
| Fragrance B [3] | — | 5-10 | — | — | 0.01-2 | — | — | 3-10 | — | — | 5-10 | — | — | 0.1-5 | — |
| Fragrance A1 or B | — | — | 5-10 | — | — | 0.01-2 | — | — | 3-10 | — | — | 5-10 | — | — | 0.1-5 |
| Ethanol | 60-99.99 | | | | | | | | | | | | | | |
| Butylated Hydroxy Toluene | 0-0.07 | | | | | | | | | | | | | | |
| Modulator A [4] | 2-20 | 2-20 | — | — | — | — | — | — | — | — | — | — | — | — | — |
| Modulator B [5] | — | — | — | 0.1 | 0.1 | — | — | — | — | — | — | — | — | — | — |
| Modulator C [6] | — | — | — | — | — | — | 0.1-5 | 0.1-5 | — | — | — | — | — | — | — |
| Modulator D [7] | — | — | — | — | — | — | — | — | — | 2-10 | 2-10 | — | — | — | — |
| Modulator E [8] | — | — | — | — | — | — | — | — | — | — | — | — | 0.1-3 | 0.1-3 | — |
| Deionized water | to 100.00 | | | | | | | | | | | | | | |

[1] Wt % is relative to the total weight of the composition.
[2] Can be any one of fragrance examples 1-3, 4b, 5b and 18.
[3] Can be any one of fragrance examples 4a, 5a and 7-17.
[4] Can be any one of the substantially non-odorous fragrance modulators examples: Sucrose laurate; sucrose dilaurate, sucrose myristate, sucrose palmitate, sucrose stearate; sucrose distearate; or sucrose tristearate.
[5] Substantially non-odorous fragrance modulator is (E)-1-(2,2,6-trimethylcyclohexyl)oct-1-en-3-one.
[6] Can be any one of the substantially non-odorous fragrance modulators examples: 2-(1-menthoxy) ethane-1-ol; 1-(1-menthoxy) propane-2-ol; 3-(1-menthoxy) propane-1-ol; 3-(1-menthoxy) propane-1,2-diol; 2-methyl-3-(1-menthoxy)propane-1,2-diol; or 4-(1-menthoxy) butane-1-ol.
[7] Substantially non-odorous fragrance modulator is Hydroquinone beta-D-glycoside.
[8] Substantially non-odorous fragrance modulator is Hyaluronic acid disaccharide sodium salt or Sodium Hyaluronate (20-50 kDa).

Tables 18(b) provides test compositions (MOD1 and MOD2) comprising the volatile fragrance formulation of fragrance example 6 (as disclosed in Table 11) with a substantially non-odorous fragrance modulator (as disclosed in Table 1) that are particularly suited to analytical measurements. All of the compositions are prepared by admixture of the components described in Table 18(b) in the proportions indicated.

TABLE 18(b)

Compositions comprising fragrance with 10 Volatile Fragrance Materials

| Ingredients | Test composition (wt % [1]) MOD 1 & 2 | Reference composition (wt % [1]) REF |
|---|---|---|
| Fragrance A [2] | 7.0 | 7.0 |
| Triethyl citrate | 0.25 to 1.0 | 0.25 to 1.0 |
| Ethanol | 75.0 | 75.0 |
| Modulator [3] | 15.0 | 0.0 |
| Water | qsp | qsp |
| Total | 100.0 | 100.0 |

[1] Wt % is relative to the total weight of the composition.
[2] Fragrance Example 6 (as disclosed in Table 11).
[3] Can be any one of the substantially non-odorous fragrance modulator nos. 1 and 3 as disclosed in Table 3.

Tables 18(c) provides test compositions comprising the volatile fragrance formulation of fragrance example 6 (as disclosed in Table 11) with a substantially non-odorous fragrance modulator (as disclosed in Table 1) that are particularly suited to analytical measurements. All of the compositions are prepared by admixture of the components described in Table 18(c) in the proportions indicated.

TABLE 18(c)

Compositions comprising fragrance with 10 Volatile Fragrance Materials

| Ingredients | Test composition (wt % [1]) | Reference composition (wt % [1]) |
|---|---|---|
| Fragrance A [2] | 0.4-7.0 | 0.40-07.0 |
| Triethyl citrate | 0.25 to 2.0 | 0.25 to 2.0 |
| Ethanol | 75.0 | 75.0 |
| Modulator [3] | 1-15.0 | 0.0 |
| Water | qsp | qsp |
| Total | 100.0 | 100.0 |

[1] Wt % is relative to the total weight of the composition.
[2] Fragrance Example 6 (as disclosed in Table 11).
[3] Can be any one of the substantially non-odorous fragrance modulator no. 2, and 4-44 as disclosed in Table 3.

Example 3—Single Fragrance Material Compositions Containing Substantially Non-Odorous Fragrance Modulators Compositions P, R, T, V, W, X, Z and ZZ are examples of compositions according to the present invention, made with single fragrance materials and the substantially non-odorous fragrance modulators, respectively. In parallel, control Compositions Q, S, U, Y and ZZZ are prepared without a substantially non-odorous fragrance modulator as a control. They are prepared by admixture of the components in Table 19(a), in the proportions indicated.

TABLE 19(a)

Single Fragrance Material Compositions

| Ingredients | \multicolumn{13}{c}{Single PRM Composition (wt %) [1]} |
|---|---|---|---|---|---|---|---|---|---|---|---|---|---|

| Ingredients | P | Q | R | S | T | U | V | W | X | Y | Z | ZZ | ZZZ |
|---|---|---|---|---|---|---|---|---|---|---|---|---|---|
| Dimethyl Benzyl Carbinol | 1 | 1 | — | — | — | — | — | — | — | — | — | — | — |
| Ethyl Safranate | — | — | 1 | 1 | — | — | — | — | — | — | — | — | — |
| Phenylethyl alcohol | — | — | — | — | 1 | 1 | — | — | — | — | — | — | — |
| Eugenol | — | — | — | — | — | — | — | — | — | — | — | 1 | 1 |
| Fragrance C [6] | — | — | — | — | — | — | 0.5-1 | 0.5-1 | 0.5-1 | 0.5-1 | 0.5-1 | — | — |
| Sucrose Myristate | 3.8 | 0 | 3.0 | 0 | 4.6 | 0 | — | — | — | — | — | — | — |
| Modulator A2 [2] | — | — | — | — | — | — | 1-5 | — | — | — | — | — | — |
| Modulator B [3] | — | — | — | — | — | — | — | 0.1 | — | — | — | — | — |
| Modulator C [4] | — | — | — | — | — | — | — | — | 0.1-5 | — | — | — | — |
| Modulator D [5] | — | — | — | — | — | — | — | — | — | — | — | 1.6 | 0 |
| Modulator E [7] | — | — | — | — | — | — | — | — | — | 0.1-3 | — | — | — |
| Eihanol | | | | | | | \multicolumn{5}{c}{to 100} | | | |

[1] Wt % is relative to the total weight of the composition.
[2] Can be any one of the substantially non-odorous modulators examples: sucrose laurate, sucrose dilaurate, sucrose palmitate, sucrose stearate, sucrose distearate, or sucrose tristearate.
[3] Can be any one of the substantially non-odorous modulators examples: (E)-1-(2,2,6-trimethylcyclohexyl)oct-1-en-3-one.
[4] Can be any one of the substantially non-odorous modulators examples: 2-(1-menthoxy) ethane-1-ol; 1-(1-menthoxy) propane-2-ol; 3-(1-menthoxy) propane-1-ol; 3-(1-menthoxy) propane-1,2-diol; 2-methyl-3-(1-menthoxy)propane-1,2-diol; or 4-(1-menthoxy) butane-1-ol.
[5] Substantially non-odorous fragrance modulator is Hydroquinone beta-D-glycoside (Arbutin).
[6] Dimethyl Benzyl Carbinol, Ethyl Safranate, Phenyl ethyl alcohol or Eugenol.
[7] Substantially non-odorous fragrance modulator is Hyaluronic acid disaccharide sodium sail or Sodium Hyaluronate (20-50 kDa).

Tables 19(b) provides test compositions comprising the a single volatile fragrance material (as disclosed in Table 2) with a substantially non-odorous fragrance modulator (as disclosed in Table 3) that are particularly suited to analytical measurements. All of the compositions are prepared by admixture of the components described in Table 19(b) in the proportions indicated.

TABLE 19(b)

Single Volatile Fragrance Material Compositions

| Ingredients | Test Composition (wt % [1]) | Reference Composition (wt % [1]) |
|---|---|---|
| Volatile Fragrance Material [2] | 1.0-3.0 | 1.0-3.0 |
| Triethyl citrate | 0.25 to 2.0 | 0.25 to 2.0 |
| Ethanol | 75.0 | 75.0 |
| Modulator [3] | 0.1-10.0 | 0.0 |
| Water | qsp | qsp |
| Total | 100.0 | 100.0 |

[1] Wt % is relative to the total weight of the composition.
[2] Can be any one of the volatile fragrance material as disclosed in Table 2.
[3] Can be any one of the substantially non-odorous fragrance modulator as disclosed in Table 3.

Example 4—Exemplary Product Compositions

Compositions I, II, III and IV are examples of body spray compositions according to the present invention. They are prepared by admixture of the components described in Table 20, in the proportions indicated.

TABLE 20

Body Spray Compositions

| Ingredients | CAS Number | I | II | III | IV |
|---|---|---|---|---|---|
| Denatured Ethanol | 64-17-5 | 39.70 | 59.45 | 39.70 | 39.70 |
| Water | 7732-18-5 | — | 0.75 | — | — |
| Dipropylene Glycol | 25265-71-8 | 15.00 | — | 15.00 | 15.00 |
| Isopropyl Myristate | 110-27-0 | 1.00 | — | 1.00 | 1.00 |
| Zinc Phenosulphonate | 127-82-2 | 0.50 | — | 0.50 | 0.50 |
| Cavasol ® W7 methylated Beta-cyclodextrin | 128446-36-6 | — | 1.00 | — | — |
| Fragrance [2] | — | 1.20 | 1.20 | 1.20 | 1.20 |
| Fragrance Modulator [3] | — | 2.60 | 2.60 | 2.60 | 2.60 |
| Propane | 74-98-6 | 4.86 | — | 4.86 | 4.86 |
| Isobutane | 72-28-5 | 27.14 | — | 27.14 | 27.14 |
| 1,1-Difluoroethane (HFC-152a) | 75-37-6 | 8.00 | 35.00 | 8.00 | 8.00 |
| Total | | 100.00 | 100.00 | 100.00 | 100.00 |

[1] wt % relative to the total weight of the composition.
[2] Can be any one of Fragrances Examples 1-3, 4b, 5b, or 18.
[3] Can be any one of the substantially non-odorous fragrance modulators disclosed in Table 3.

Composition V, VI and VII are examples of body lotion compositions according to the present invention. They are prepared by admixture of the components as described in Table 21, in the proportions indicated.

TABLE 21

Body Lotion Composition

| Ingredients | CAS Number | V | VI | VII |
|---|---|---|---|---|
| Water | 7732-18-5 | qsp 100% | qsp 100% | qsp 100% |
| Trilon ® B | 64-02-8 | 0.05 | 0.05 | 0.05 |

TABLE 21-continued

Body Lotion Composition

| Ingredients | CAS Number | Compositions (wt % [1]) | | |
|---|---|---|---|---|
| | | V | VI | VII |
| Carbopol ® ETD 2050 | 9003-01-4 | 0.2 | 0.2 | 0.2 |
| Pemulen ™ TR1 | 9063-87-0 | 0.2 | 0.2 | 0.2 |
| Nexbase ® 2008 | 68037-01-4 | 8 | 8 | 8 |
| Silicone V100 | 63148-62-9 | 6 | 6 | 6 |
| Fragrance Modulator [3] | — | 3 | 3 | 3 |
| Tris Amino ™ Ultra Pur | 102-71-6 | 0.4 | 0.4 | 0.4 |
| Fragrance [2] | — | 3 | 3 | 3 |
| Preservatives | — | qs | qs | qs |
| Total | | 100.00 | 100.00 | 100.00 |

[1] wt % relative to the total weight of the composition.
[2] Can be any one of the Fragrances Examples 1-3, 4b, 5b, or 18.
[3] Can be any one of the substantially non-odorous fragrance modulators disclosed in Table 3.

Example 5—Olfactive Test Results

Compositions disclosed in Tables 18(a) and 19(a)-19(b) are applied to glass slides in accordance with the protocol described in the Method Section and a panel of around 6-10 experienced panelists evaluate the perceived fragrance profile at initial time 0, then at various time points, typically 1 hour, 2 hours, 3 hours, 4 hours and 6 hours post application. Panelists are asked to score the compositions for the longevity of the fragrance profile on a scale of 0 to 5, wherein 0 represents a no fragrance is detected and 5 represents a very strong fragrance intensity is detected; and for fragrance profile fidelity on a scale of 0 to 3 wherein 0 represents not detectable and 3 represents it being the dominant character. The results of the panelists are then averaged and discussed below.

(a) Effects of the Substantially Non-Odorous Fragrance Modulators on Single Fragrance Material Compositions FIG. 1 shows the fragrance intensity profile of Composition R as evaluated by 10 panelists, which comprises the substantially non-odorous fragrance modulator sucrose myristate and the single fragrance material, ethyl safranate. Addition of the substantially non-odorous fragrance modulator maintains the intensity of the fragrance material for up to 6 hours whilst the control, Composition S, in the absence of the substantially non-odorous fragrance modulator, drops in fragrance intensity profile over the 6 hours. The substantially non-odorous fragrance modulator acts to maintain the continued evaporation over time of the fragrance material. Statistical analysis using the Tukey correction for multiple comparisons confirms the statistically significant difference at 0 hours ($p=0.0015$), 1 hour ($p=0.0033$), 3 hours ($p=0.0015$) and 6 hours (($p=0.0152$) all at 95% significance level (i.e., $p<0.05$).

FIG. 2 shows the fragrance intensity profile of Composition P as evaluated by 10 panellists, which comprises the substantially non-odorous fragrance modulator sucrose myristate and the single fragrance material, Dimethylbenzyl carbinol. Addition of the substantially non-odorous fragrance modulator maintains the intensity of the fragrance material for up to 6 hours whilst the control, Composition Q, in the absence of the substantially non-odorous fragrance modulator, drops in fragrance intensity profile over the 6 hours. The substantially non-odorous fragrance modulator acts to maintain the continued evaporation over time of the fragrance material. Statistical analysis using the Tukey correction for multiple comparisons confirms the statistically significant difference at 1 hour ($p=0.0581$) at 90% significance level (i.e., $p<0.1$), 3 hours ($p=0.0311$) at 95% significance level (i.e., $p<0.05$).

FIG. 3 shows the fragrance intensity profile of Composition T as evaluated by 10 panelists, which comprises the substantially non-odorous fragrance modulator sucrose myristate and the single fragrance material phenethyl alcohol (PEA). Addition of the substantially non-odorous fragrance modulator maintains the intensity of the fragrance material for up to 6 hours whilst the control, Composition U, in the absence of the substantially non-odorous fragrance modulator, drops in fragrance intensity profile over the 6 hours. The substantially non-odorous fragrance modulator acts to maintain the continued evaporation over time of the fragrance material. Statistical analysis using the Tukey correction for multiple comparisons confirms the statistically significant difference at 1 hour ($p<0.0001$), 3 hours ($p=0.0016$) and 6 hours ($p=0.0003$) all at 95% significance level (i.e., $p<0.05$).

FIG. 4 shows the fragrance intensity profile of Composition ZZ as evaluated by 11 panelists, which comprises the substantially non-odorous fragrance modulator hydroquinone beta-D-glycoside and the single fragrance material, eugenol. Addition of the substantially non-odorous modulator maintains the intensity of the fragrance material for up to 6 hours whilst the control, Composition ZZZ, in the absence of the substantially non-odorous fragrance modulator, drops in fragrance intensity profile over the 6 hours. The substantially non-odorous fragrance modulator acts to maintain the continued evaporation over time of the fragrance material. Statistical analysis using the Tukey correction for multiple comparisons confirms the statistically significant difference at 1 hour ($p=0.0008$) and 3 hours ($p=0.0123$) all at 95% significance level (i.e., $p<0.05$).

(b) Effects of the Substantially Non-Odorous Fragrance Modulators on the Fragrance Profile Longevity of Compositions Having Reduced Levels of Low Volatile Fragrance Materials (Between 10 to 30 wt % Relative to the Total Weight of the Fragrance Component) Vs. Compositions Having Traditional Levels of Low Volatile Fragrance Materials (Greater than 30 wt Relative to the Total Weight of the Fragrance Component) and No Substantially Non-Odorous Fragrance Modulator Panelists are asked to score the compositions for the intensity of the fragrance on a scale of 0 to 5, wherein 0 represents no fragrance intensity is detected and 5 represents a very strong fragrance intensity is detected. The results of the panel test are then averaged. The results show the effect of the substantially non-odorous fragrance modulator and reduced levels of low volatile fragrance materials for any one of the inventive Compositions A, D, G, J and M on fragrance profile longevity versus control Compositions C, F, I, L and O in the absence of a substantially non-odorous modulator. Alternatively, the results show the effect of the substantially non-odorous fragrance modulator and reduced levels of low volatile fragrance materials for any one of the inventive Compositions A, D, G, J and M on fragrance profile longevity versus traditional Compositions B, E, H, K and N in the presence of the substantially non-odorous fragrance modulator.

Fragrance profile longevity, is maintained for up to at least 6 hours in the presence of the substantially non-odorous fragrance modulator whilst it drops in the absence of the substantially non-odorous fragrance modulator (data not shown). Without wishing to be bound by theory, it is believed that the substantially non-odorous fragrance modulator acts to maintain the continued evaporation over time of the fragrance materials, particular the volatile fragrance materials. The effect of the improved fragrance profile longevity of the present invention are noticeable at 1, 3 and 6 hours.

(c) Effects of the Substantially Non-Odorous Fragrance Modulators on the Fragrance Profile Fidelity of Compositions Reduced Levels of Low Volatile Fragrance Materials (Between 10 to 30 wt % Relative to the Total Weight of the Fragrance Component) Vs. Compositions Having Traditional Levels of Low Volatile Fragrance Materials (Greater than 30 wt % Relative to the Total Weight of the Fragrance Component) and No Substantially Non-Odorous Fragrance Modulator Panelists are are also asked to score the composition for the fragrance profile fidelity. In particular, the panelists are asked to score the dominance of the floral character attributable to the volatile fragrance materials on a scale of 0 to 3 wherein 0 represents not detectable and 3 represents it being the dominant character. The results of the panel test are then averaged. The results show the effect of the substantially non-odorous fragrance modulator and reduced levels of low volatile fragrance materials for the inventive Compositions A, D, G, J and M on fragrance profile fidelity versus control Compositions C, F, I, L, and O in the absence of a substantially non-odorous modulator.

Alternatively, the results show the effect of the substantially non-odorous fragrance modulator and reduced levels of low volatile fragrance materials for any one of the inventive Compositions A, D, G, J and M on fragrance profile fidelity versus traditional Compositions B, E, H, K and N in the presence of the substantially non-odorous fragrance modulator.

Fragrance profile fidelity, particularly floral character attributable to the volatile fragrance materials are maintained by the substantially non-odorous fragrance modulator over time for up to 6 hours in the presence of the substantially non-odorous fragrance modulator whilst it drops in the absence of the substantially non-odorous fragrance modulator (data not shown).

Panelists are further asked to score the compositions on a scale of 1 to 5, wherein 1 represents the fragrance profile remains unchanged and 5 represents a total change in the fragrance profile versus a control. The results of the panel test are averaged and plotted together with the confidence intervals. The results show the effect of the substantially non-odorous fragrance modulator and reduced levels of low volatile fragrance materials for any one of the inventive Compositions A, D, G, J and M. The presence of the substantially non-odorous fragrance modulator and the reduced levels of low volatile fragrance materials result in noticeable fidelity in fragrance characters. Particularly, noticeable fidelity in the floral characters attributable to the volatile fragrance materials (data not shown).

Example 6—Analytical Evaporation Test Results

Using the analytical evaporation Test Method 3, it is possible to measure the amount of each component of a perfume mixture that remains as the fragrance mixture evaporates. Test compositions (MOD1 and MOD2) as disclosed in Table 18(b) and other compositions disclosed in Table 18(c), comprising a mixture of 10 volatile perfume materials, as disclosed in Table 11 (Fragrance Example 6), and a substantially non-odorous fragrance modulators, as disclosed in Table 3, are introduced in the aluminum containers at the set temperature for pre-determined periods of time in accordance with the protocol described in Test Method 3. Indole is one of the components of the 10 PRMs mixture of Table 11. Control compositions containing the full 10 PRMs, or one component (e.g., indole), without the substantially non-odorous fragrance modulator are run alongside the test compositions. The average profile for the control composition is plotted against the individual profile for the indole component from the test composition containing the 10 PRMs mixture of Table 11 with the substantially non-odorous fragrance modulators. The error associated with the method is determined by running replicate evaporation experiments on the control composition. An average evaporation profile of the control composition as well as the 95% confidence interval at each time point are calculated from the replicates.

It is useful to consider the difference ($\Delta$) in the % of remaining fragrance material between each of the test composition (MOD) and their respective control composition (REF) at each experimental time points (e.g., 30 mins, 60 mins and 180 mins) to determine the effect of the substantially non-odorous fragrance modulator on the volatile PRMs in a mixture. The difference ($\Delta$) in the % of remaining of a given fragrance material is calculated as follows:

$$\Delta = \% \text{ remaining of given fragrance material in test composition(MOD)} - \% \text{ remaining of same fragrance material in control composition(REF)}$$

The difference ($\Delta$) can then be plotted (data not shown) for each of the perfume materials in the mixture at each of the time points. For ease of reference, the applicant has summarize the effect of the substantially non-odorous fragrance modulator on only one volatile fragrance component (e.g., indole) of the mixture, to serve as a representative of all of the volatile fragrance materials.

(a) Effects of Sucrose Laurate on Compositions Having Volatile Fragrance Materials FIG. 5 shows the effect of the substantially non-odorous fragrance modulator sucrose laurate on the evaporation profile for a representative component (i.e., indole) of the test composition (MOD1). With reference to FIG. 5, indole has a difference ($\Delta$) of 15% after 30 mins, 25% after 60 mins, and 72% after 3 hours. Addition of the sucrose myristate in the test composition (MOD1) maintains the concentration of the volatile fragrance material indole from 0 hour up to 3 hours whilst the control composition (REF), in the absence of sucrose laurate, drops in fragrance concentration over the 3 hours. Thus, sucrose laurate acts to maintain the continued evaporation of the volatile fragrance material over time. Similar results are observed for the other volatile fragrance materials in the mixture (data not shown).

(b) Effects of Sucrose Myristate on Compositions Having Volatile Fragrance Materials FIG. 6 shows the effect of the substantially non-odorous fragrance modulator sucrose myristate on the evaporation profile for a representative component (i.e., indole) of the test composition (MOD2). With reference to FIG. 6, indole has a difference ($\Delta$) of 14% after 30 mins, 26% after 60 mins, and 72% after 3 hours. Addition of the sucrose myristate in the test composition (MOD2) maintains the concentration of the volatile fragrance material indole from 0 hour up to 3 hours whilst the control composition (REF), in the absence of sucrose myristate, drops in fragrance concentration over the 3 hours. Thus, sucrose myristate acts to maintain the slow evaporation of the volatile fragrance material over time. Similar results are observed for the other volatile perfume materials in the mixture (data not shown).

Example 7—Analytical Headspace Tests

Using the analytical headspace Test Method 4, it is possible to demonstrate the character retention over time of a perfume mixture of a fragrance composition of the present invention vs. a control. Compositions disclosed in Table 18(a) are added to sealed vials in accordance with the procotol described in the Method Section, and the fragrance profiles in the headspace are measured at specific time points through the use of headspace gas chromatography.

The test demonstrates the character retention over time of a fragrance composition. The results show the effect of the substantially non-odorous fragrance modulator and reduced levels of low volatile fragrance materials for any one of the inventive Compositions A, D, G, J, and M on fragrance profile longevity versus control Compositions C, F, I, L, and O, in the absence of the substantially non-odorous modulator. Alternatively, results show the effect of the substantially non-odorous fragrance modulator and reduced levels of low volatile fragrance materials for any one of the inventive Compositions A, D, G, J, and M on fragrance profile longevity versus traditional Compositions B, E, H, K, and N, in the presence of the substantially non-odorous fragrance modulator. Fragrance profile fidelity, particularly characters attributable to the volatile fragrance materials are maintained for up to at least 1 hour in the presence of the substantially non-odorous fragrance modulator whilst they drop in the absence of the substantially non-odorous fragrance modulator.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising:
   (i) a fragrance component present in an amount of from about 0.04 wt % to about 30 wt %, relative to the total weight of the composition, and wherein the fragrance component comprises
      (a) from about 10 wt % to about 30 wt %, relative to the total weight of the fragrance component, of a low volatile fragrance material having a vapor pressure less than 0.001 Torr at 25° C., and (b) from about 70 wt % to about 99.9 wt %, by weight of the fragrance component, of a volatile fragrance material having a vapor pressure greater than or equal to 0.001 Torr at 25° C. comprising limonene; and
   (ii) at least one substantially non-odorous fragrance modulator comprising sucrose laurate present in the amount of from about 0.1 wt % to about 20 wt %, relative to the total weight of the composition; and
   wherein the sucrose laurate and fragrance component are present in a weight ratio from about 3:1 to about 1:3.

2. The composition according to claim 1, further comprising a volatile solvent present in the amount of from about 50 wt % to about 80 wt %, and wherein the solvent is a branched or unbranched $C_1$ to $C_{10}$ alkyl, alkenyl, or alkynyl group having at least one alcohol moiety.

3. The composition according to claim 1, wherein the composition is a fine fragrance composition in the form of a perfume concentrate, a perfume, a parfum, an eau de toilette, an eau de parfum, or a cologne.

4. The composition according to claim 1, wherein the composition is in the form of a body splash or a body spray.

5. A perfuming consumer product or article comprising a composition according to claim 1, wherein the perfuming consumer product is selected from the group consisting of a fabric care product, an air care product or a home care product.

* * * * *